(12) United States Patent
Rogers et al.

(10) Patent No.: US 10,820,862 B2
(45) Date of Patent: Nov. 3, 2020

(54) ORGAN MOUNTED ELECTRONICS

(71) Applicants: THE BOARD OF TRUSTEES OF THE UNIVERSITY OF ILLINOIS, Urbana, IL (US); WASHINGTON UNIVERSITY IN ST. LOUIS, St. Louis, MO (US)

(72) Inventors: John A. Rogers, Champaign, IL (US); Igor Efimov, Wildwood, MO (US); Sarah Gutbrod, St. Louis, MO (US); Lizhi Xu, Urbana, IL (US); Andrew Bonifas, Woodbury, MN (US); Richard Chad Webb, Urbana, IL (US); Ahyeon Koh, Champaign, IL (US)

(73) Assignees: The Board of Trustees of the University of Illinois, Urbana, IL (US); Washington University, St. Louis, MO (US)

( * ) Notice: Subject to any disclaimer, the term of this patent is extended or adjusted under 35 U.S.C. 154(b) by 1183 days.

(21) Appl. No.: 14/504,736

(22) Filed: Oct. 2, 2014

(65) Prior Publication Data
US 2015/0141767 A1 May 21, 2015

Related U.S. Application Data

(60) Provisional application No. 61/885,994, filed on Oct. 2, 2013, provisional application No. 61/937,187, filed
(Continued)

(51) Int. Cl.
*A61B 5/00* (2006.01)
*A61B 5/03* (2006.01)
(Continued)

(52) U.S. Cl.
CPC ............ *A61B 5/6885* (2013.01); *A61B 5/036* (2013.01); *A61B 5/0422* (2013.01);
(Continued)

(58) Field of Classification Search
CPC ...... A61N 1/0597; A61N 1/375; A61B 18/14; A61B 2018/00351; A61B 2562/028;
(Continued)

(56) References Cited

U.S. PATENT DOCUMENTS

| | | |
|---|---|---|
| 5,231,301 A | 7/1993 | Peterson et al. |
| 5,316,017 A | 5/1994 | Edwards |

(Continued)

FOREIGN PATENT DOCUMENTS

| | | |
|---|---|---|
| WO | WO 1998/049936 | 11/1998 |
| WO | WO 2009/114689 | 9/2009 |

(Continued)

OTHER PUBLICATIONS

Ahn et al. (2006) "Heterogeneous three-dimensional electronics by use of printed semiconductor nanomaterials," *Science*. 314:1754-1757.

(Continued)

*Primary Examiner* — Eric D. Bertram
*Assistant Examiner* — Pamela M. Bays
(74) *Attorney, Agent, or Firm* — Leydig, Voit & Mayer, Ltd.

(57) ABSTRACT

Provided are devices and methods capable of interfacing with biological tissues, such as organs like the heart, in real-time and using techniques which provide the ability to monitor and control complex physical, chemical, biochemical and thermal properties of the tissues as a function of time. The described devices and methods utilize micro scale sensors and actuators to spatially monitor and control a variety of physical, chemical and biological tissue parameters, such as temperature, pH, spatial position, force, pressure, electrophysiology and to spatially provide a variety of stimuli, such as heat, light, voltage and current.

44 Claims, 41 Drawing Sheets

Related U.S. Application Data on Feb. 7, 2014, provisional application No. 62/003,786, filed on May 28, 2014.

(51) Int. Cl.

| | |
|---|---|
| *A61B 5/11* | (2006.01) |
| *A61H 23/02* | (2006.01) |
| *A61B 5/145* | (2006.01) |
| *A61B 5/0205* | (2006.01) |
| *A61B 5/042* | (2006.01) |
| *A61N 2/00* | (2006.01) |
| *A61B 5/1473* | (2006.01) |
| *A61N 1/05* | (2006.01) |
| *A61B 18/14* | (2006.01) |
| *A61N 5/06* | (2006.01) |
| *A61N 1/375* | (2006.01) |
| *A61N 1/362* | (2006.01) |
| *A61B 18/00* | (2006.01) |
| *A61B 5/01* | (2006.01) |
| *A61F 7/00* | (2006.01) |
| *A61B 5/053* | (2006.01) |

(52) U.S. Cl.
CPC ............ *A61B 5/1107* (2013.01); *A61B 5/686* (2013.01); *A61B 5/6843* (2013.01); *A61B 5/6869* (2013.01); *A61B 18/14* (2013.01); *A61N 1/0597* (2013.01); *A61B 5/0036* (2018.08); *A61B 5/0084* (2013.01); *A61B 5/01* (2013.01); *A61B 5/015* (2013.01); *A61B 5/02055* (2013.01); *A61B 5/0538* (2013.01); *A61B 5/1116* (2013.01); *A61B 5/1473* (2013.01); *A61B 5/14539* (2013.01); *A61B 5/14546* (2013.01); *A61B 5/4836* (2013.01); *A61B 2018/00351* (2013.01); *A61B 2562/028* (2013.01); *A61B 2562/0215* (2017.08); *A61B 2562/046* (2013.01); *A61B 2562/164* (2013.01); *A61F 7/007* (2013.01); *A61H 23/0245* (2013.01); *A61H 2201/10* (2013.01); *A61N 1/0563* (2013.01); *A61N 1/3621* (2013.01); *A61N 1/375* (2013.01); *A61N 1/37512* (2017.08); *A61N 2/002* (2013.01); *A61N 2/006* (2013.01); *A61N 5/0603* (2013.01); *A61N 5/0622* (2013.01)

(58) Field of Classification Search
CPC ........ A61B 2562/046; A61B 2562/164; A61B 5/01; A61B 5/1107; A61B 5/686; A61B 5/6885; A61B 5/6869; A61B 5/6843
USPC .......................................................... 607/2
See application file for complete search history.

(56) References Cited

U.S. PATENT DOCUMENTS

| | | | |
|---|---|---|---|
| 5,687,737 A | 11/1997 | Branham et al. | |
| 6,487,906 B1 | 12/2002 | Hock | |
| 6,666,821 B2 | 12/2003 | Keimel | |
| 7,195,733 B2 | 3/2007 | Rogers et al. | |
| 7,521,292 B2 | 4/2009 | Rogers et al. | |
| 7,557,367 B2 | 7/2009 | Rogers et al. | |
| 7,622,367 B1 | 11/2009 | Nuzzo et al. | |
| 7,629,691 B2 | 12/2009 | Roush et al. | |
| 7,704,684 B2 | 4/2010 | Rogers et al. | |
| 7,705,280 B2 | 4/2010 | Nuzzo et al. | |
| 7,799,699 B2 | 9/2010 | Nuzzo et al. | |
| 7,932,123 B2 | 4/2011 | Rogers et al. | |
| 7,943,491 B2 | 5/2011 | Nuzzo et al. | |
| 7,972,875 B2 | 7/2011 | Rogers et al. | |
| 7,982,296 B2 | 7/2011 | Nuzzo et al. | |
| 8,039,847 B2 | 10/2011 | Nuzzo et al. | |
| 8,198,621 B2 | 6/2012 | Rogers et al. | |
| 8,217,381 B2 | 7/2012 | Rogers et al. | |
| 8,367,035 B2 | 2/2013 | Rogers et al. | |
| 8,394,706 B2 | 3/2013 | Nuzzo et al. | |
| 8,440,546 B2 | 5/2013 | Nuzzo et al. | |
| 8,470,701 B2 | 6/2013 | Rogers et al. | |
| 8,552,299 B2 | 10/2013 | Rogers et al. | |
| 8,562,095 B2 | 10/2013 | Alleyene et al. | |
| 8,664,699 B2 | 3/2014 | Nuzzo et al. | |
| 8,666,471 B2 | 3/2014 | Rogers et al. | |
| 8,679,888 B2 | 3/2014 | Rogers et al. | |
| 8,722,458 B2 | 5/2014 | Rogers et al. | |
| 8,729,524 B2 | 5/2014 | Rogers et al. | |
| 8,754,396 B2 | 6/2014 | Rogers et al. | |
| 8,865,489 B2 | 10/2014 | Rogers et al. | |
| 8,895,406 B2 | 11/2014 | Rogers et al. | |
| 2003/0149456 A1 | 8/2003 | Rottenberg et al. | |
| 2003/0199955 A1 | 10/2003 | Struble et al. | |
| 2004/0015058 A1* | 1/2004 | Besson .............. | A61B 5/14552 600/301 |
| 2005/0006237 A1* | 1/2005 | Larkin ............... | G01N 27/3335 204/416 |
| 2005/0085869 A1* | 4/2005 | Tehrani ................ | A61N 1/3601 607/42 |
| 2006/0173364 A1 | 8/2006 | Clancy et al. | |
| 2007/0043416 A1* | 2/2007 | Callas ................. | A61N 1/0597 607/129 |
| 2007/0208395 A1* | 9/2007 | Leclerc ................ | A61N 5/0616 607/86 |
| 2007/0257821 A1 | 11/2007 | Son et al. | |
| 2008/0055581 A1 | 3/2008 | Rogers et al. | |
| 2008/0097559 A1* | 4/2008 | Eggers .............. | A61B 18/1233 607/102 |
| 2009/0012533 A1 | 1/2009 | Barbagli et al. | |
| 2009/0293664 A1 | 12/2009 | Aabloo et al. | |
| 2010/0141407 A1 | 6/2010 | Heubel et al. | |
| 2011/0034912 A1 | 2/2011 | De Graff et al. | |
| 2011/0071439 A1 | 3/2011 | Bach-y-Rita et al. | |
| 2011/0147715 A1 | 6/2011 | Rogers et al. | |
| 2011/0170225 A1 | 7/2011 | Rogers et al. | |
| 2011/0187798 A1 | 8/2011 | Rogers et al. | |
| 2011/0230747 A1 | 9/2011 | Rogers et al. | |
| 2011/0276112 A1 | 11/2011 | Simon et al. | |
| 2011/0316120 A1 | 12/2011 | Rogers et al. | |
| 2012/0157804 A1 | 6/2012 | Rogers et al. | |
| 2012/0165759 A1 | 6/2012 | Rogers et al. | |
| 2012/0261551 A1 | 10/2012 | Rogers et al. | |
| 2012/0320581 A1 | 12/2012 | Rogers et al. | |
| 2013/0036928 A1 | 2/2013 | Rogers et al. | |
| 2013/0041235 A1 | 2/2013 | Rogers et al. | |
| 2013/0072775 A1 | 3/2013 | Rogers et al. | |
| 2013/0140649 A1 | 6/2013 | Rogers et al. | |
| 2013/0333094 A1 | 12/2013 | Rogers et al. | |
| 2014/0163390 A1 | 6/2014 | Rogers et al. | |
| 2014/0191236 A1 | 7/2014 | Nuzzo et al. | |
| 2014/0216524 A1 | 8/2014 | Rogers et al. | |
| 2014/0220422 A1 | 8/2014 | Rogers et al. | |
| 2014/0323968 A1 | 10/2014 | Rogers et al. | |

FOREIGN PATENT DOCUMENTS

| | | |
|---|---|---|
| WO | WO 2010/081989 | 7/2010 |
| WO | WO 2011/084450 | 7/2011 |

OTHER PUBLICATIONS

Alanen et al. (2004) "Measurement of Hydration in the Stratum Corneum with the Moisturemeter and Comparison with the Corneometer," *Skin Research and Technology*. 10:32-37.

Alekseev, et al. (2008) "Millimeter Wave Reflectivity Used for Measurement of Skin Hydration with Different Moisturizers," *Skin Res. Technol*, 14:390-396.

Al-Halhouli et al. (2008) "Nanoindentation Testing of SU-8 Photoresist Mechanical Properties," *Microelectronic Eng.* 85:942-944.

(56) References Cited

OTHER PUBLICATIONS

Al-Hardan et al. (2010) "The Effect of Oxygen Ratio on the Crystallography and Optical Emission Properties of Reactive RF Sputtered ZnO Films," *Physica B*. 405:1081-1085.
Aliot et al. (2009) "EHRA/HRS Expert Consensus on Catheter Ablation of Ventricular Arrhythmias: Developed in a partnership with the European Heart Rhythm Association (EHRA), a Registered Branch of the European Society of Cardiology (ESC), and the Heart Rhythm Society (HRS); in collaboration with the American College of Cardiology (ACC) and the American Heart Association (AHA)," *Europace* 11:771-817.
Amir et al. (2000) "The Influence of Helium-Neon Irradiation on the Viability of Skin Flaps in the Rat," *Br. J. Plast. Surg.* 53:58-62.
Andosca et al. (2012) "Experimental and Theoretical Studies on MEMS Piezoelectric Vibrational Energy Harvesters with Mass Loading," *Sensors and Actuators A*. 178:76-87.
Angelopoulos et al. (Sep. 17-21, 2012) "Manufacturing aspects of an ultra-thin chip technology," In; Solid-State Device Research Conference (ESSDERC) 2012: Proceedings of the European. Bordeaux, France. Ed.: Yann Deval pp. 141-144.
Arumugam et al. (1994) "Effect of Strain Rate on the Fracture Behaviour of Skin," *J. Bioscience*. 19(3):307-313.
Attas et al. (2002) "Near-IR Spectroscopic Imaging for Skin Hydration: The Long and the Short of it," *Biopolymers*. 67:96-106.
Baca et al. (2007) "Printable Single-Crystal Silicon Micro/Nanoscale Ribbons, Platelets and Bars Generated from Bulk Wafers," *Adv. Funct. Mater.* 17:3051-3062.
Baca et al. (2008) "Semiconductor Wires and Ribbons for High-Performance Flexible Electronics," *Angew. Chem. Int. Ed.* 47:5524-5542.
Bach-y-Rita et al. (2003) "Seeing with the Brain," *Int. J. Hum-Comput. Int.*15:285-296.
Barbottin (1989) Ch. 15 In; *Instabilities in Silicon Devices*. vol. 2 *Elsevier*. Amsterdam, The Netherlands.
Barel et al. (1997) "In Vitro Calibration of the Capacitance Method (Corneometer CM 825) and Conductance Method (Skicon-200) for the Evaluation of the Hydration State of the Skin," *Skin Research and Technology*. 3:107-113.
Barfield et al. (1995) "Comparison of Human Sensory Capabilities with Technical Specifications for Virtual Environment Equipment," *Presence-Teleoperators and Virtual Environments*. 4:329-356.
Baskoutas et al. (2011) "Transition in the Optical Emission Polarization of ZnO Nanorods," *J. Phys. Chem. C*. 115:15862.
Berger (1929) "Über das Elektrenkephalogram des. Menschen." *Arch Psychiatr Nervenkr*. 87:527-570.
Bernardini et al. (1997) "Spontaneous Polarization and Piezoelectric Constants of III-V nitrides," *Physics Review B*. 56:10024.
Bettinger et al. (2010) "Biomaterials-Based Organic Electronic Devices," *Polym. Int.* 59:563-567.
Bettinger et al. (2010) "Organic Thin-Film Transistors Fabricated on Resorbable Biomaterial Substrates," *Adv. Mater.* 22:651-655.
Biot (1963) "Surface Instability of Rubber in Compression," *Appl. Sci. Res. A*. 12:168-182.
Blichmann et al. (1987) "Hydration Studies on Scaly Hand Eczema," *Contact Dermatitis*. 16:155-159.
Blom et al. (1990) "Thin-film ZnO as Micromechanical Actuator at Low Frequencies," *Sensors and Actuators*. 21:226-228.
Boguniewicz, et al. (2008) "A Multidisciplinary Approach to Evaluation and Treatment of Atopic Dermatitis," *Seminars in Cutaneous Medicine and Surgery*. 27:115-127.
Briscoe (2012) "Measured Efficiency of a ZnO Nanostructured Diode Piezoelectric Energy Harvesting Device," *Appl. Phys. Lett.* 101:093902.
Brown et al. (2005) "Evaluation of Polydimethylsiloxane Scaffolds with Physiologically-Relevant Elastic Moduli: Interplay of Substrate Mechanics and Surface Chemistry Effects on Vascular Smooth Muscle Cell Response," *Biomaterials* 26:3123-3129.
Buck et al. (1995) "Microfabrication technology of flexible membrane based sensors for in vivo applications," *Electroanalysis*. 7:846-851.

Bühlmann et al. (2012) "Ion-Selective Electrodes With Ionophore-Doped Sensing Membranes," In; *Supramolecular Chemistry*. Eds. Gale, P.; Steed, J. *John Wiley and Sons, Ltd*.
Burghartz et al. (2009) "A new fabrication and assembly process for ultra-thin chips," *IEEE T. Electron Dev.* 56:321-327.
Burk et al. (Aug. 16, 2013) "Electrodeposition of Pt Nanoparticle Catalysts from $H_2Pt(OH)_6$ and Their Application in PEM Fuel Cells," *J. Phys. Chem. C*. 117:18957-18966.
Camacho et al. (2011) "Structural, Optical and Electrical Properties of ZnO Thin Films Grown by Radio Frequency (RF) Sputtering in Oxygen Atmosphere," *International Journal of Physical Sciences*. 6:6660-6663.
Garcia et al. (2006) "High-Performance ZnO Thin-Film Transistors On Gate Dielectrics Grown By Atomic Layer Deposition," *Appl. Phys. Lett.* 88:123509.
Carlson et al. (2012) "Transfer printing techniques for materials assembly and micro/nanodevice fabrication," *Adv. Mater.* 24:5284-5318.
Chan et al. (Jan. 27, 2013) "MRI-detectable pH nanosensors incorporated into hydrogels for in vivo sensing of transplanted-cell viability," *Nat. Mater.* 12:268-275.
Chang et al. (2010) "Direct-Write Piezoelectric Polymeric Nanogenerator with High Energy Conversion Efficiency," *Nano Lett.*10:726-731.
Chaudhury et al. (1991) "Direct Measurement of Interfacial Interactions Between Semispherical Lenses and Flat Sheets of Poly(Dimethylsiloxane) and their Chemical Derivatives," *Langmuir*. 7:1013-1025.
Chen et al. (2005) "Humidity Sensors: A Review of Materials and Mechanisms," *Sensor Letters*. 3:274-295.
Choi et al. (2003) "Investigation of Gate-Induced Drain Leakage (GIDL) Current in Thin Body Devices: Single-Gate Ultra-Thin Body, Symmetrical Double-Gate, and Asymmetrical Double-Gate MOSFETs," *Jpn. J. Appl. Phys.* 42:2073-2076.
Choi-Yim et al. (1998) "The Effect of Silicon on the Glass Forming Ability of the $Cu_{47}Ti_{34}Zr_{11}Ni_8$ Bulk Metallic Glass Forming Alloy During Processing of Composites," *J. Appl. Phys.* 83:7993-7997.
Chung et al. (2011) "Fabrication of Releasable Single-Crystal Silicon-Metal Oxide Field-Effect Devices and Their Deterministic Assembly on Foreign Substrates," *Adv. Func. Mater.* 21:3029-3036.
Chung et al. (Jul. 19, 2013) "Stretchable, multiplexed pH sensors with demonstrations on rabbit and human hearts undergoing ischemia," *Adv. Healthc. Mater.* 3:59-68.
Clarys et al. (1999) "Non-Invasive Electrical Measurements for the Evaluation of the Hydration State of the Skin: Comparison Between Three Conventional Instruments—the Corneometer®, the Skicon® and the Nova DPM®," *Skin Research and Technology*. 5:14-20.
Clerc (1976) "Directional Differences of Impulse Spread in Trabecular Muscle from Mammalian Heart," *J. Physiol.* 255:335-346.
Cohen-Karni et al. (2009) "Flexible Electrical Recording from Cells Using Nanowire Transistor Arrays," *Proc. Natl. Acad. Sci. USA* 106:7309-7313.
Cole et al. (2008) "Patterned Growth and Transfer of ZnO Micro- and Nanocrystals with Size and Location Control," *Adv. Mater.* 20:1474-1478.
Corazza et al. (2007) "Photobiomodulation on the Angiogenesis of Skin Wounds in Rats Using Different Light Sources," *Photomedicine Laser Surg.* 25:102-106.
Cox (1952) "The Elasticity and Strength of Paper and Other Fibrous Materials," *Br. J. Appl. Phys.* 3:72-79.
Csutak et al. (2002) "CMOS-Compatible High-Speed Planar Silicon Photodiodes Fabricated on SOI Substrates," *IEEE Journal of Quantum Electronics*. 38:193-196.
Czekalla et al. (2008) "Spatial Fluctuations of Optical Emission from Single ZnO/MgZnO Nanowire Quantum Wells," *International Journal of Nanotechnology*. 19:115202.
Dagdeviren et al. (Apr. 19, 2013) "Transient, Biocompatible Electronics and Energy Harvesters Based on ZnO," *Small*. 9:3398-3404.
Danckwerts (1950) "Absorption by Simultaneous Diffusion and Chemical Reaction," *Transactions of the Faraday Society*. 46:300-304.

(56) References Cited

OTHER PUBLICATIONS

Danilova et al. (2008) "Dipole Analysis of Event-Related Oscillations in Anticipation Processes," *International Journal of Psychophysiology*. 69:161-162.
Dassault Systèmes (2010) "Abaqus 6.10: Analysis User's Manual v.6.10," *Dassault Systèmes Simulia Corp*. Rhode Island.
David et al. (2012) "Dissolution Kinetics and Solubility of ZnO Nanoparticles Followed by AGNES," *J. Phys. Chem*. 116:11758.
DeVries et al. (2001) "A novel technique for measurement of pericardial pressure," *Am. J. Physiol. Heart. Circ. Physiol*. 280:H2815-H2822.
D'hooge et al. (2000) "Regional strain and strain rate measurements by cardiac ultrasound: Principles, implementation and limitations," *Eur. J. Echocardiogr*. 1:154-170.
Dobrev (2000) "Use of Cutometer to Assess Epidermal Hydration," *Skin Research and Technology*. 6:239-244.
Ducéré et al. (2005) "A Capacitive Humidity Sensor Using Cross-Linked Cellulose Acetate Butyrate," *Sensors and Actuators B: Chemical*. 106:331-334.
Dupuis et al. (2008) "History, Development, and Applications of High-Brightness Visible Light-Emitting Diodes," *IEEE J. Lightwave Tech*. 26:1154-1171.
Efimov et al. (2004) "Optical imaging of the heart," *Circ. Res*. 95:21-33.
Farid et al. (Oct. 6, 2011) "Role of K-atp channels in the maintenance of ventricular fibrillation in cardiomyopathic human hearts," *Circ. Res*. 109:1309-1318.
Faris et al. (2003) "Novel technique for cardiac electromechanical mapping with magnetic resonance imaging tagging and an epicardial electrode sock," *Ann. Biomed. Eng*. 31:430-440.
Fink et al. (2001) "Enhancement of device performance in vertical sub-100 nm MOS devices due to local channel doping," *Solid State Electron*. 46:387-391.
Fluhr et al. (1999) "Comparative Study of Five Instruments Measuring Stratum Corneum Hydration (Corneometer CM 820 and CM 825, Skicon 200, Nova DPM 9003, DermaLab). Part I. In vitro," *Skin Research and Technology*. 5:161-170.
Forrest et al. (2004) "The Path to Ubiquitous and Low-Cost Organic Electronic Appliances on Plastic," *Nature* 428:911-918.
Fox et al. (1976) "Transcutaneous Electrical Stimulation and Acupuncture: Comparison of Treatment for Low-Back Pain," *Pain*. 2:141-148.
Frodin et al. (1988) "Hydration of Human Stratum Corneum Studied In Vivo by Optothermal Infrared Spectrometry, Electrical Capacitance Measurement, and Evaporimetry," *Acta Derm Venereol*. 68:461-467.
Fulati et al. (2009) "Miniaturized pH Sensors Based on Zinc Oxide Nanotubes/Nanorods," *Sensors*. 9:8911-8923.
Gardner et al. (1965) "Physical Aspects of the Internal Water Relations of Plant Leaves," *Plant Physiol*. 40:705-710.
Geerligs et al. (2011) "In Vivo Indentation to Determine the Mechanical Properties of Epidermis," *J. Biomech*. 44:1176-1181.
Gerischer et al. (1992) "Chemical dissolution of zinc oxide crystals in aqueous electrolytes—An analysis of the kinetics," *Electrochimica Acta*. 37:827-835.
Gonzalez et al. (2008) "Design of Metal Interconnects for Stretchable Electronic Circuits," *Microelectronics Reliability*. 48:825-832.
Griss et al. (2002) "Characterization of Micromachined Spiked Biopotential Electrodes," *IEEE Trans. Biomed. Eng*. 49:597-604.
Grosjean et al. (2006) "Hydrolysis of Mg—salt and MgH2-Salt Mixtures Prepared by Ball Milling for Hydrogen Production," *Journal of Alloys and Compounds*. 416:296-302.
Guimerà et al. (2008) "Method and Device for Bio-Impedance Measurement with Hard-Tissue Applications," *Physiological Measurement*. 29:S279.
Gullapalli et al. (2010) "Flexible Piezoelectric ZnO—Paper Nanocomposite Strain Sensor," *Small*. 6:1641-1646.
Gupta et al. (2010) "Development of Gas Sensors Using ZnO Nanostructures," *J. Chem. Sci*. 122:57-62.
Gutbrod et al. (Aug. 5, 2014) "Patient-specific flexible and stretchable devices for cardiac diagnostics and therapy," *Prog. Biophys. Mol. Biol*. 115:244-251.
Hamed et al. (Dec. 2012) "Construction, In Vitro and In Vivo Evaluation of an In-House Conductance Meter for Measurement of Skin Hydration," *Medical Engineering & Physics*. 34:1471-1476.
Hancock (1971) "Subacute effusive-constrictive pericarditis," *Circulation*. 43:183-192.
Hardyck et al. (1966) "Feedback of Speech Muscle Activity During Silent Reading: Rapid Extinction," *Science*. 154:1467-1468.
Harrison et al. (1980) "The sock electrode array—a tool for determining global epicardial activation during unstable arrhythmias," *Pacing Clin. Electrophysiol*. 3:531-540.
Hayase et al. (2001) "Photoangioplasty with Local Motexafin Lutetium Delivery Reduces Macrophages in a Rabbit Post-Balloon Injury Model," *Cardiovascular Res*. 49:449-455.
Hendriks, et al. (2004) "Influence of Hydration and Experimental Length Scale on the Mechanical Response of Human Skin In Vivo, Using Optical Coherence Tomography," *Skin Research and Technology*. 10: 231-241.
Hoffman et al. (2003) "ZnO-Based Transparent Thin-Film Transistors," *Appl. Phys. Lett*. 82:733.
Holt et al. (1960) "Pericardial and ventricular pressure," *Circ. Res*. 8:1171-1181.
Hu et al. (2009) "Highly Conductive Paper for Energy-Storage Devices," *Proc. Natl. Acad. Sci. USA* 106:21490-21494.
Hu et al. (2010) "Stretchable, Porous, and Conductive Energy Textiles," *Nano Lett*. 10:708-714.
Hua et al. (1993) "Finite Element Modeling of Electrode-Skin Contact Impedance in Electrical Impedance Tomography," *IEEE Transactions on Biomedical Engineering*. 40:335-343.
Huang et al. (2005) "Stamp Collapse in Soft Lithography," *Langmuir* 21:8058-8068.
Huang et al. (2011) "A Flexible pH Sensor Based on the Iridium Oxide Sensing Film," *Sensors and Actuators A: Physical*. 169:1-11.
Huang et al. (Dec. 2012) "Epidermal Differential Impedance Sensor for Conformal Skin Hydration Monitoring," *Biointerphases*. 7:52. pp. 1-9.
Hudson et al. (2008) "The Biocompatibility of Mesoporous Silicates," *Biomaterials*. 29:4045-4055.
Hutchinson et al. (1992) "Mixed Mode Cracking in Layered Materials," *Adv. Appl. Mech*. 29:63-191.
Hwang et al. (Sep. 28, 2012) "A Physically Transient Form of Silicon Electronics," *Science*. 337:1640-1644.
Ilican et al. (2008) "Preparation and Characterization of ZnO Thin Films Deposited by Sol-Gel Coating Method," *Journal of Optoelectronics and Advanced Materials*. 10:2578-2583.
International Search Report and Written Opinion corresponding to International Patent Application No. PCT/US2013/034667, dated Aug. 19, 2013.
International Search Report with Written Opinion corresponding to International Patent Application No. PCT/US2014/058768, dated Jan. 24, 2015.
Irimia-Vladu (2010) "Biocompatible and Biodegradable Materials for Organic Field-Effect Transistors," *Adv. Funct. Mater*. 20:4069-4076.
Ives et al. (2007) "Miniaturized, On-Head, Invasive Electrode Connector Integrated EEG Data Acquisition System," *Clinical Neurophysiol*. 118:1633-1638.
Jacobs et al. (2001) "Submicrometer Patterning of Charge in Thin-Film Electrets," *Science* 291:1763-1766.
Janardhan et al. (Sep. 26, 2013) "Multistage Electrotherapy Delivered Through Chronically-Implanted Leads Terminates Atrial Fibrillation With Lower Energy Than a Single Biphasic Shock," *J. Am. Coll. Cardiol*. 63:40-48.
Jeon et al. (2003) "Structural and Mechanical Properties of Woven Fabrics Employing Peirce's Model," *Textile Res. J*. 73:929-933.
Jeon et al. (2007) "Low-Voltage Zinc-Oxide Thin-Film Transistors on a Conventional $SiO_2$ Gate Insulator Grown by Radio-Frequency Magnetron Sputtering at Room Temperature," *J. of the Korean Physical Society* 51:1999-2003.

(56) References Cited

OTHER PUBLICATIONS

Jiang et al. (2008) "Post-Buckling Anlysis for the Precisely Controlled Buckling of Thin Film Encapsulated by Elastomeric Substrates," *Int. J. Solids Struct.* 45, 2014-2023.
Jones (2008) Tactile Displays: Guidance for Their Design and Application,: *Human Factors*. 50:90-111.
Kaczmarek et al. (1991) "Electrotactile and Vibrotactile Displays for Sensory Substitution Systems," *IEEE Transactions on Biomedical Engineering*. 38:1-16.
Kaczmarek et al. (2003) "Pattern Identification and Perceived Stimulus Quality as a Function of Stimulation Waveform on a Fingertip-Scanned Electrotactile Display," *IEEE Transactions on Neural Systems and Rehabilitation Engineering*. 11:9-16.
Kadish et al. (1988) "Interaction of Fiber Orientation and Direction of Impulse Propagation with Anatomic Barriers in Anisotropic Canine Myocardium," *Circulation*. 78:1478-1494.
Kadlec et al. (2008) "Assessing Skin Hydration Status in Haemodialysis Patients Using Terahertz Spectroscopy: A Pilot/Feasibility Study," *Physics in Medicine and Biology*. 53:7063.
Kaltenbrunner et al. (Jul. 24, 2013) "An ultra-lightweight design for imperceptible plastic electronics," *Nature*. 499:458-463.
Kaneko et al. (2005) "The Influence of Age on Pressure Perception of Static and Moving Two-Point Discrimination in Normal Subjects," *J. Hand Ther.* 18:421-424.
Keplinger et al. (2010) "Röntgen's Electrode-Free Elastomer Actuators without Electromechanical Pull-In Instability," *Proc. Natl. Acad. Sci. USA*. 107:4505-4510.
Khang et al. (2006) "A Stretchable Form of Single-Crystal Silicon for High-Performance Electronics on Rubber Substrates," *Science* 311:208-212.
Kim et al. (2008) "Stretchable and foldable silicon integrated circuits," *Science*. 320(5875):507-511.
Kim et al. (2008) "Stretchable Electronics: Materials Strategies and Devices," *Adv. Mater.* 20:4887-4892.
Kim et al. (2009) "Optimized Structural Designs for Stretchable Silicon Integrated Circuits," *Small* 5(24):2841-2847.
Kim et al. (2010) "Waterproof AlInGaP optoelectronics on stretchable substrates with applications in biomedicine and robotics," *Nat. Mater.* 9:929-937.
Kim et al. (2011) "Epidermal Electronics," *Science*. 333(6044):838-843.
Kim et al. (2011) "Materials for Multifunctional Balloon Catheters With Capabilities in Cardiac Electrophysiological Mapping and Ablation Therapy," *Nat. Mater.* 10:316-323.
Kim et al. (Dec. 2, 2008) "Materials and Noncoplanar Mesh Designs for Integrated Circuits with Linear Elastic Responses to Extreme Mechanical Deformations," *Proc. Natl. Acad. Sci. USA* 105(48):18675-18680.
Kim et al. (Dec. 4, 2012) "Electronic sensor and actuator webs for large-area complex geometry cardiac mapping and therapy," *Proc. Natl. Acad. Sci. USA*. 109:19910-19915.
Kim et al. (Jun. 21, 2011) "Unusual strategies for using indium gallium nitride grown on silicon (111) for solid-state lighting," *Proc. Natl. Acad. Sci. USA*. 108:10072-10077.
Kim et al. (May 2013) "Deterministic Assembly of Releasable Single Crystal Silicon-Metal Oxide Field-Effect Devices Formed From Bulk Wafers," *Applied Physics Letters*. 102:182104.
Kim et al. (Oct. 22, 2012) "Flexible vertical light emitting diodes," *Small*. 8:3123-3128.
Kim et al. (Web Release Apr. 18, 2010) "Dissolvable Films of Silk Fibroin for Ultrathin Conformal Bio-Integrated Electronics," *Nature Materials* 9:511-517.
Kim et al. (Web Release Jul. 6, 2009) "Ultrathin Silicon Circuits with Strain-Isolation Layers and Mesh Layouts for High-Performance Electronics on Fabric, Vinyl, Leather and Paper," *Adv. Mater.* 21(36):3703-3707.
Kleiner (1999) "Water: An Essential But Overlooked Nutrient," *Journal of the American Dietetic Association*. 99:200-206.

Klode et al. (2011) "Investigation of Adhesion of Modern Wound Dressings: A Comparative Analysis of 56 Different Wound Dressings," *J. Eur. Acad. Dermatol.* 25(8):933-939.
Knuesel et al. (2010) "Self-assembly of microscopic chiplets at a liquid-liquid-solid interface forming a flexible segmented monocrystalline solar cell," *Proc. Natl. Acad. Sci. USA* 107:993-998.
Ko et al. (2010) "Flexible Carbon Nanofiber Connectors with Anisotropic Adhesion Properties," *Small* 6:22-26.
Ko et al. (Aug. 7, 2008) "A Hemispherical Electronic Eye Camera Based on Compressible Silicon Optoelectronics," *Nature* 454:748-753.
Kubo et al. (2010) "Stretchable Microfluidic Radiofrequency Antennas," *Adv. Mater.* 22:2749-2752.
Kumar et al. (2006) "Ultrasensitive DNA Sequence Detection Using Nanoscale ZnO Sensor Arrays," *Nanotechnology*. 17:2875.
Kumar et al. (2011) "ZnO Nanoparticle as Catalyst for Efficient Green One-Pot Synthesis of Coumarins through Knoevenagel Condensation," *J. Chem. Sci.*123:615-621.
Kuo (2004) Ch.6 In; *Thin Film Transistors Materials and Processes*. vol. 1. *Klewer Academic*. Norwell, MA. pp. 241-271.
Kurzweil (2009) "Metal Oxides and Ion-Exchanging Surfaces as pH Sensors in Liquids: State-of-the-Art and Outlook," *Sensors (Basel)*. 9:4955-4985.
Kuwazuru et al. (2008) "Mechanical Approach to Aging and Wrinkling of Human Facial Skin Based on the Multistage Buckling Theory," *Med. Eng. Physics*. 30:516-522.
Lacour et al. (2005) "Stretchable Interconnects for Elastic Electronic Surfaces," *Proc. IEEE* 93:1459-1467.
Laughner et al. (Jul. 20, 2012) "Processing and analysis of cardiac optical mapping data obtained with potentiometric dyes," *Am. J. Physiol. Heart. Circ. Physiol.* 303:H753-H765.
Lee et al. (2005) "Dielectrophoresis and Chemically Mediated Directed Self-Assembly of Micrometer-Scale Three-Terminal Metal Oxide Semiconductor Field-Effect Transistors," *Adv. Mater.* 17:2671-2677.
Legnani et al. (2008) "Bacterial Cellulose Membrane as Flexible Substrate for Organic Light Emitting Devices," *Thin Film Solids*. 517:1016-1020.
Leong et al. (2009) "Tetherless Thermobiochemicall Actuated Microgrippers," *Proc. Natl. Acad. Sci. USA* 106:703-709.
Li et al. (2008) "Cellular Level Biocompatibility and Biosafety of ZnO Nanowires," *J. Phys. Chem. C.* 112:20114-20117.
Li et al. (Jan. 21, 2013) "An Analytical Model of Reactive Diffusion for Transient Electronics," *Adv. Funct. Mater.* 23:3106-3114.
Lipomi et al. (2011) "Skin-Like Sensors of Pressure and Strain Enabled by Transparent, Elastic Films of Carbon Nanotubes," *Nature Nanotech*. 6:788-792.
Loo et al. (2008) "Progress and Challenges in Commercialization of Organic Electronics," *MRS Bull*. 33:653-662.
Lou et al. (Oct. 28, 2011) "The role of dynamic instability and wavelength in arrhythmia maintenance as revealed by panoramic imaging with blebbistatin vs. 2,3-butanedione monoxime," *Am. J. Physiol. Heart. Circ. Physiol.* 302:H262-H269.
Lozano (2009) "Electrotactile Stimulation on the Tongue: Intensity Perception, Discrimination, and Cross-Modality Estimation," *Somatosens. Mot. Res.* 26:50-63.
Ma et al. (2010) "A Stretchable Electrode Array for Non-Invasive, Skin-Mounted Measurement of Electrocardiography (ECG), Electromyography (EMG) and Electroencephalography (EEG)," In; Engineering in Medicine and Biology Society (EMBC), 2010 Annual International Conference of the IEEE. Buenos Aires, Arentina. pp. 6405-6408.
Mack et al. (2006) "Mechanically Flexible Thin-Film Transistors that Use Ultrathin Ribbons of Silicon Derived from Bulk Wafers," *Appl. Phys. Lett.* 88:213101.
Mannsfeld et al. (2010) "Highly Sensitive Flexible Pressure Sensors with Microstructured Rubber Dielectric Layers," *Nat. Mater.* 9:859-864.
Martinez-Boubeta et al. (2010) "Self-Assembled Multifunctional Fe/MgO Nanospheres for Magnetic Resonance Imaging and Hyperthermia," *Nanomedicine: Nanotechnology, Biology, and Medicine*. 6:362-370.

(56) References Cited

OTHER PUBLICATIONS

Martinsen, et al. (1999) "Measuring depth depends on frequency in electrical skin impedance measurements," *Skin Research and Technology.* 5:179-181.
Masuda et al. (2003) "Transparent Thin Film Transistors Using Zno as an Active Channel Layer and Their Electrical Properties," *J. Appl. Phys.* 93:1624.
Matteau et al. (2010) "Beyond Visual, Aural and Haptic Movement Perception: hMT+ is Activated by Electrotactile Motion Stimulation of the Tongue in Sighted and in Congenitally Blind Individuals," *Brain Research Bulletin.* 82:264-270.
Matthie (2008) "Bioimpedance Measurements of Human Body Composition: Critical Analysis and Outlook," *Expert Rev. Med. Devices.* 5:239-261.
Meitl et al. (2006) "Transfer Printing by Kinetic Control of Adhesion to an Elastomeric Stamp," *Nat. Mater.* 5:33-38.
Menard et al. (2007) "Micro- and Nanopatterning Techniques for Organic Electronic and Optoelectronic Systems," *Chem. Rev.* 107:1117-1160.
Michalske et al. (1985) "Closure and Repropagation of Healed Cracks in Silicate Glass," *J. Am. Ceram. Soc.* 68:586-590.
Miyamoto et al. (2004) "High-Electron-Mobility ZnO epilayers Grown by Plasma-Assisted Molecular Beam Epitaxy," *Journal of Crystal Growth.* 265:34-40.
Momose et al. (2002) "Ultrathin gate oxide CMOS on (111) surface-oriented Si substrate," *IEEE Trans. Electron. Dev.* 49:1597-1605.
Mondal et al. (2008) "Preparation of Al—doped ZnO (AZO) Thin Film by SILAR," *Journal of Physical Sciences.* 12:221-229.
Moore et al. (1959) "II. Diffusion of Zinc and Oxygen in Zinc Oxide," *Discussions of the Faraday Society.* 28:86-93.
Moore et al. (2000) "Three-dimensional systolic strain patterns in the normal human left ventricle: Characterization with tagged MR imaging," *Radiology.* 214:453-466.
Moravej et al. (2011) "Biodegradable Metals for Cardiovascular Stent Application: Interests and New Opportunities," *Int. J. Mol. Sci.* 12:4250-4270.
Mudunkotuwa et al. (2012) "Dissolution of ZnO Nanoparticles at Circumeutral pH: A Study of Size Effects in the Prescencse and Asbsence of Citric Acid," *Langmuir.* 28:396-403.
Neely et al. (1967) "Effect of pressure development on oxygen consumption by isolated rat heart," *Am. J. Physiol.* 212:804-814.
Ondo-Ndong et al. (2003) "Electrical Properties of Zinc Oxide Sputtered Thin Films," *Microelectronics Journal.* 34:1087-1092.
Overholt et al. (2005) "Photodynamic Therapy for Esophageal Cancer using a 180° Windowed Esophageal Balloon," *Lasers in Surg. Med.* 14:27-33.
Pailler-Mattei et al. (2008) "In Vivo Measurements of the Elastic Mechanical Properties of Human Skin by Indentation Tests," *Med. Eng. Phys.* 30:599-606.
Pang et al. (2012) "A flexible and highly sensitive strain-gauge sensor using reversible interlocking of nanofibres," *Nat. Mater.* 11:795-801.
Panilaitis et al. (2003) "Macrophage Activation in Response to Silk," *Biomaterials.* 24:3079-3085.
Park et al. (2008) "Theoretical and Experimental Studies in Bending of Inorganic Electronic Materials on Plastic Substrates," *Adv. Funct. Mater.* 18:2673-2684.
Park et al. (2009) "The Effects of Rapid Thermal Annealing on the Performance of ZnO Thin-Film Transistors," *Journal of the Korean Physical Society.* 55:1925-1930.
Park et al. (Aug. 2009) "Printed Assemblies of Inorganic Light-Emitting Diodes for Deformable and Semitransparent Displays," *Science* 325:977-981.
Patolsky et al. (2006) "Stimulation, and Inhibition of Neuronal Signals with High-Density Nanowire Transistor Arrays," *Science* 313:1100-1104.
Paye et al. (1995) "Corneometiy Measurements to Evaluate Skin Dryness in the Modified Soap Chamber Test," *Skin Research and Technology.* 1:123-127.

Pierret (1996) Ch. 18 In; *Semiconductor Device Fundamentals. Addison-Wesley.* Natick, MA. pp. 645-690.
Qian et al. (2006) "Scaling Effects of Wet Adhesion in Biological Attachment Systems," *Acta Biomaterialia* 2:51-58.
Razavi et al. (2009) "Three Dimensional Nanopillar Array Photovoltaics on Low Cost and Flexible Substrates," *Nature Materials* 8:648-653.
Reed et al. (2012) "Solubility of Nano-Zinc Oxide in Environmentally and Biologically Important Matrices," *Environ. Toxicol. Chem.* 31:93-99.
Reuss et al. (Jul. 2005) "Macroelectronics: Perspectives on Technology and Applications," *Proc. IEEE* 93(7):1239-1256.
Richter et al. (2008) "Review on Hydrogel-based pH Sensors and Microsensors," *Sensors.* 8:561-581.
Rieke et al. (2008) "MR thermometry," *J. Magn. Reson. Imaging.* 27:376-390.
Rodriguez et al. (2007) "Dual-Frequency Resonance-Tracking Atomic Force Microscopy," *Nanotechnology.* 18:475504.
Rogers et al. (2009) "Correction for a Curvy, Stretchy Future for Electronics," *Proc. Natl. Acad. Sci. U. S. A.* 106:16889.
Rogers et al. (2009) "A Curvy, Stretchy Future for Electronics," *Proc. Natl. Acad. Sci. U. S. A.* 106:10875-10876.
Rogers et al. (2010) "Materials and Mechanics for Stretchable Electronics," *Science.* 327:1603-1607.
Rogers et al. (Sep. 1, 2011) "Synthesis, Assembly and Applications of Semiconductor Nanomembranes," *Nature.* 477:45-53.
Rubehn et al. (2009) "A MEMS based Flexible Multichannel ECoG-Electrode Array," *J. Neural Eng.* 6:036003.
Saad et al. (2008) "Characterization of Various Zinc Oxide Catalysts and Their Activity in the Dehydration-Dehydrogenation of Isobutanol" *J. Serb. Chem. Soc.* 73:997-1009.
Sato et al. (1999) "Anisotropic etching rates of single-crystal silicon for TMAH water solution as a function of crystallographic orientation," *Sens. Actuators A.* 73:131-137.
Scherlag et al. (1969) "Catheter Technique for Recording His Bundle Activity in Man," *Circulation* 39:13-18.
Schindl et al. (2003) "Direct Stimulatory Effect of Low-Intensity 670-nm Laser Irradiation on Human Endothelial Cell Proliferation," *Br. J. Dermatol.* 148:334-336.
Searle et al. (2000) "A Direct Comparison of Wet, Dry and Insulating Bioelectric Recording Electrodes," *Physiol. Meas.* 21:271.
Sekitani (2008) "A Rubberlike Stretchable Active Matrix Using Elastic Conductors," *Science.* 321:1468-1472.
Sekitani et al. (2009) "Stretchable Active-Matrix Organic Light-Emitting Diode Display Using Printable Elastic Conductors," *Nature Mater.* 8:494-499.
Sekitani et al. (2012) "Stretchable Organic Integrated Circuits for Large-Area Electronic Skin Surfaces," *MRS Bull.* 37:236-245.
Shabetai (2004) "Pericardial effusion: Haemodynamic spectrum," *Heart.* 90:255-256.
Shahrjerdi et al. (Oct. 23, 2013) "Extremely Flexible Nanoscale Ultrathin Body Silicon Integrated Circuits on Plastic," *Nano Lett.* 13:315-320.
Sharma et al. (1986) "Influence of Heat-Stress Induced Dehydration on Mental Functions," *Ergonomics.* 29:791-799.
Shen et al. (2007) "Submicron Particles of SBA-15 Modified with MgO as Carriers for Controlled Drug Delivery," *Chem. Pharm. Bull.* 55:985-991.
Shimizu et al. (2012) "Letter: Zinc Oxide Paste as Sunscreen in the Postoperative Period," *Dermatologic Surgery* 38:965-966.
Siegel et al. (2009) "Thin, Lightweight, Foldable Thermochromic Displays on Paper," *Lab Chip* 9:2775-2781.
Siegel et al. (2010) "Foldable Printed Circuit Boards on Paper Substrates," *Adv. Funct. Mater.* 20:28-35.
Smiseth et al. (1985) "Assessment of pericardial constraint in dogs," *Circulation.* 71:158-164.
So et al. (2008) "Organic Light-Emitting Devices for Solid-State Lighting," *MRS Bull.* 33:663-669.
Someya et al. (2005) "Conformable, Flexible, Large-Area Networks of Pressure and Thermal Sensors with Organic Transistor Active Matrixes," *Proc. Nat. Acad. Sci. USA* 102:12321-12325.

(56) References Cited

OTHER PUBLICATIONS

Someya et al. (Jul. 6, 2004) "A Large-Area, Flexible, Pressure Sensor Matric with Organic Field-Effect Transistors for Artificial Skin Applications," *Proc. Nat. Acad. Sci. USA* 101(27):9966-9970.
Song et al. (2003) "Understanding Magnesium Corrosion—A Framework for Improved Alloy Performance," *Advanced Engineering Materials*. 5:837-858.
Song et al. (2009) "Mechanics of noncoplanar mesh design for stretchable electronic circuits," *Journal of Applied Physics*. 105:123516.
Sparks et al. (1978) "Investigating the MESA (multipoint electrotactile speech aid): the transmission of segmental features of speech," *Journal of the Acoustical Society of America*. 63:246-257.
Staiger et al. (2006) "Magnesium and its Alloys as Orthopedic Biomaterials: A Review," *Biomaterials*. 27:1728-1734.
Stathis et al. (2006) "The negative bias temperature instability in MOS devices: A review," *Microelec. Rel*. 46:270-286.
Stauth et al. (2006) "Self-assembled single-crystal silicon circuits on plastic," *Proc. Natl. Acad. Sci. USA* 19:13922-13927.
Stroop (1935) "Studies of Interference in Serial Verbal Reactions," *Journal of Experimental Psychology*. 18:643-662.
Su et al. (2012) "Postbuckling Analysis and its Application to Stretchable Electronics," *Journal of the Mechanics and Physics of Solids*. 60:487-508.
Sum et al. (2009) "Near-Infrared Spectroscopy for the Detection of Lipid Core Coronary Plaques," *Curr. Cardiovasc. Imag. Rep*. 2:307-315.
Tagami et al. (1980) "Evaluation of the Skin Surface Hydration In Vivo by Electrical Measurement," *J. Investig. Dermatol*. 75:500-507.
Takagi et al. (1994) "On the Universality of Inversion Layer Mobility in Si MOSFET's: Part II—Effects on Surface Orientation," *IEEE Trans. Electron Dev*. 41:2363-2368.
Takei et al. (2010) "Nanowire Active-Matrix Circuitry for Low-Voltage Macroscale Artificial Skin," *Nat. Mater*. 9:821-826.
Tan et al. (1999) "Information Transmission with a Multifinger Tactual Display," *Perception & Psychophysics*. 61:993-1008.
Tchvialeva et al. (2010) "Skin Roughness Assessment," In; *New Developments in Biomedical Engineering*. D. Campolo: Eds. *InTech*. p. 341-358.
Timko et al. (2009) "Electrical Recording from Hearts with Flexible Nanowire Device Arrays," *Nano Lett*. 9:914-918.
Timoshenko et al. (1959) *Theory of Plates and Shells. McGraw-Hill Kogakusha*. Japan.
Trewyn et al. (2008) "Biocompatible Mesoporous Silica Nanoparticles with Different Morphologies for Animal Cell Membrane Penetration," *Chemical Engineering Journal*. 137:23-29.
Tyberg et al. (1986) "The relationship between pericardial pressure and right atrial pressure—an intraoperative study," *Circulation*. 73:428-432.
Valtiner et al. (2008) "Stabilization and acidic dissolution mechanism of single crystalline ZnO(0001) surfaces in electrolytes studied by in-situ AFM imaging and ex-situ LEED," *Langmuir*. 24:5350-5358.
Vidal-Verdu et al. (2007) "Graphical Tactile Displays for Visually-Impaired People," *IEEE Transactions on Neural Systems and Rehabilitation Engineering*. 15:119-130.
Vinck et al. (2003) "Increased Fibroblast Proliferation Induced by Light Emitting Diode and Low Power Laser Irradiation," *Lasers Med. Sci*. 18:95-99.
Viventi et al. (Mar. 2010) "A Conformal, Bio-Interfaced Class of Silicon Electronics for Mapping Cardiac Electrophysiology," *Sci. Trans. Med*. 2(24):24ra22.
Vuillerme et al. (2008) "Sensory Supplementation System Based on Electrotactile Tongue Biofeedback of Head Position for Balance Control," *Neurosci. Lett*. 431:206-210.
Waksman et al.(2008) "Photopoint Photodynamic Therapy Promotes Stabilization of Atherosclerotic Plaques and Inhibits Plaque Progression," *J. Am. Coll. Cardiol*. 52:1024-1032.
Wales et al. (2003) "Stationary Points and Dynamics in High-Dimensional Systems," *J. Chem. Phys*. 119:12409.

Wang (May 2012) "Mechanics of Epidermal Electronics," *Journal of Applied Mechanics*. 79:031022.
Wang et al. (1999) "Electromechanical Coupling and Output Efficiency of Piezoelectric Bending Actuators," *IEEE transactions on Ultrasonics, Ferroelectrics and Frequency Control*. 46:638-646.
Warren et al. (2008) "Receptive Field Characteristics Under Electrotactile Stimulation of the Fingertip," *IEEE Transactions on Neural Systems and Rehabilitation Engineering*. 16:410-415.
Waxman et al. (2009) "In vivo Validation of a Catheter-Based Near-Infrared Spectroscopy System for Detection of Lipid Core Coronary Plaques: Initial Results of the Spectacl Study," *J. Am. Coll. Cardiol. Img*. 2:858-868.
Waxman, S. (2008) "Near-Infrared Spectroscopy for Plaque Characterization," *J. Interv. Cardiol*. 21:452-458.
Webb et al. (Sep. 15, 2013) "Ultrathin conformal devices for precise and continuous thermal characterization of human skin," *Nat. Mater*. 12:938-944.
Wegnera et al. (2006) "In situ formation and hydrolysis of Zn nanoparticles for $H_2$ Production by the 2-Step ZnO/Zn Water-Splitting Thermochemical Cycle," *International Journal of Hydrogen Energy*. 31:55-61.
Won et al. (2011) "Piezoresitive Strain Sensors and Multiplexed Arrays Using Assemblies of Single-Crystalline Silicon Nanoribbons on Plastic Substrates," *IEEE Transactions on Electron Devices*. 58:4074-4078.
Wong-Riley et al. (2005) "Photobiomodulation Directly Benefits Primary Neurons Functionally Inactivated by Toxins," *J. Biol. Chem*. 280:4761-4771.
Woo et al. (1992) "Skin Impedance Measurements Using Simple and Compound Electrodes," *Medical & Biological Engineering& Computing*. 30:97-102.
Woodburn et al. (1996) "Phototherapy of Cancer and Atheromatous Plaque with Texaphyrins," *J. Clin. Laser Med. Surg*. 14:343-348.
Worley et al. (1987) "A new sock electrode for recording epicardial activation from the human heart—one size fits all," *Pacing Clin. Electrophysiol*. 10:21-31.
Xu et al. (Feb. 25, 2014) "3D multifunctional integumentary membranes for spatiotemporal cardiac measurements and stimulation across the entire epicardium," *Nat. Commun*. 5: 3329.
Yao et al. (2008) "Seeing Molecules by Eye: Surface Plasmon Resonance Imaging at Visible Wavelengths with High Spatial Resolution and Submonolayer Sensitivity," *Angew. Chem*. 47:5013-5017.
Yao et al. (2010) "Functional Nanostructured Plasmonic Materials," *Adv. Mater*. 22:1102-1110.
Yao et al. (Mar. 15, 2012) "A contact lens with embedded sensor for monitoring tear glucose level," *Bioelectron*. 26:3290-3296.
Yeo et al. (Feb. 26, 2013) "Multifunctional Epidermal Electronics Printed Directly Onto the Skin," *Advanced Materials*. 25:2773-2778.
Ying et al. (Mar. 27, 2012) "Silicon Nanomembranes for Fingertip Electronics," *Nanotechnology*. 23: 344004.
Yu et al. (2004) "The Yield Strength of Thin Copper Films on Kapton," *J. Appl. Phys*. 95:2991-2997.
Yu et al. (2007) "Micropatterning Metal Electrode of Organic Light Emitting Devices Using Rapid Polydimethylsiloxane Lift-Off," *Appl. Phys. Lett*. 91:043102.
Yu et al. (2009) "A Microfabricated Electrode with Hollow Microneedles for ECG Measurement," *Sens. Actuators A*. 151:17-22.
Zhai et al. (2012) "High-Performance Flexible Thin-Film Transistors Exfoliated from Bulk Wafer," *Nano Lett*. 12:5609-5615.
Zhang et al. (2010) "Fabrication and Comparative Study of Top-Gate and Bottom-Gate ZnO-TFTs with Various Insulator Layers," *J. Mater. Sci: Mater. Electron*. 21:671-675.
Zhao et al. (2004) "Piezoelectric Characterization of Individual Zinc Oxide Nanobelt Probed by Piezoresponse Force Microscopy," *Nano Lett*. 4:587-590.
Zheng et al. (1998) "Sudden Cardiac Death in the United States, 1989 to 1998," *Circulation* 104, 2158-2163.
Zheng et al. (2009) "In Vitro and In Vivo Biocompatibility Studies of ZnO Nanoparticles," *International Journal of Modern Physics B*. 23:1566-1571.

(56) References Cited

OTHER PUBLICATIONS

Zhou et al. (2006) "Dissolving Behavior and Stability of ZnO Wires in Biofluids: A Study on Biodegradability and Biocompatibility of ZnO Nanostructures," *Adv. Mater.* 18:2432-2435.

Zhou et al. (Feb. 18, 2013) "Fast Flexible Electronics with Strained Silicon Nanomembranes," *Scientific Reports.* 3:1291.

Zhu et al. (2010) "Flexible High-Output Nanogenerator Based on Lateral ZnO Nanowire Array," *Nano Lett.* 10:3151-3155.

Zipes et al. (2006) "ACC/AHA/ESC 2006 Guidelines for Management of Patients With Ventricular Arrhythmias and the Prevention of Sudden Cardiac Death: A Report of the American College of Cardiology/American Heart Association Task Force and the European Society of Cardiology Committee for Practice Guidelines (Writing Committee to Develop Guidelines for Management of Patients With Ventricular Arrhythmias and the Prevention of Sudden Cardiac Death," *Circulation* 114:385-484.

Extended European Search Report and Opinion dated May 12, 2017 for European Patent Application No. 14851143.9.

\* cited by examiner

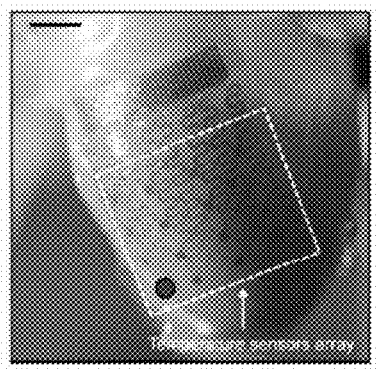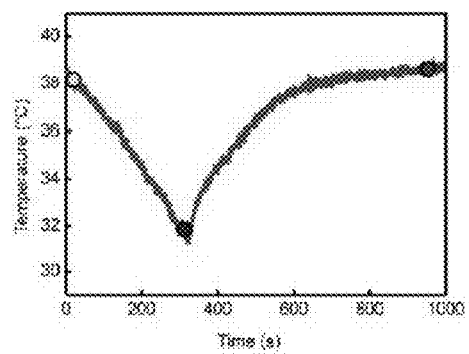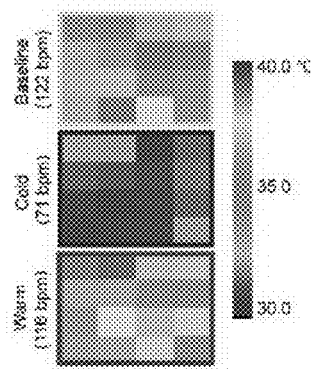
Figure 6A
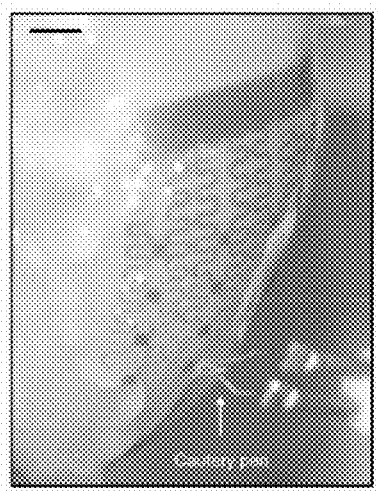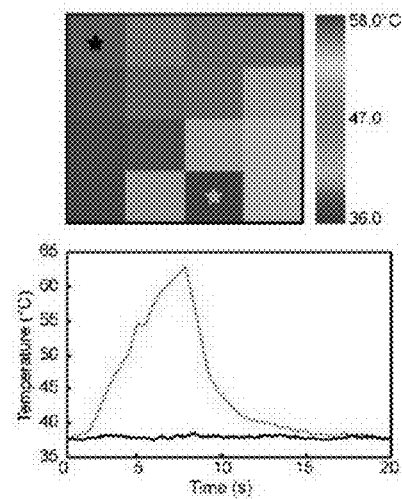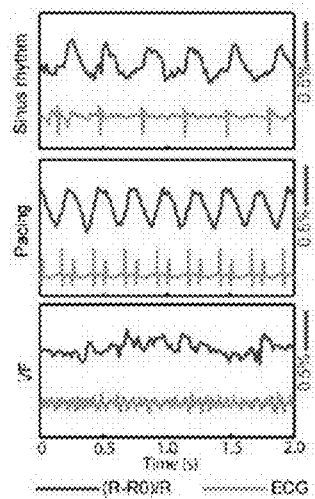
Figure 6B
Figure 6C
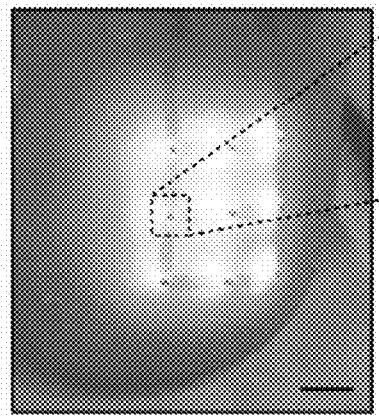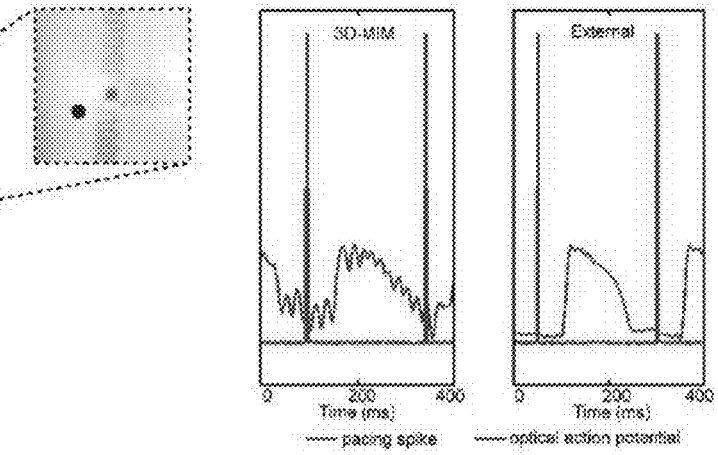
Figure 6D

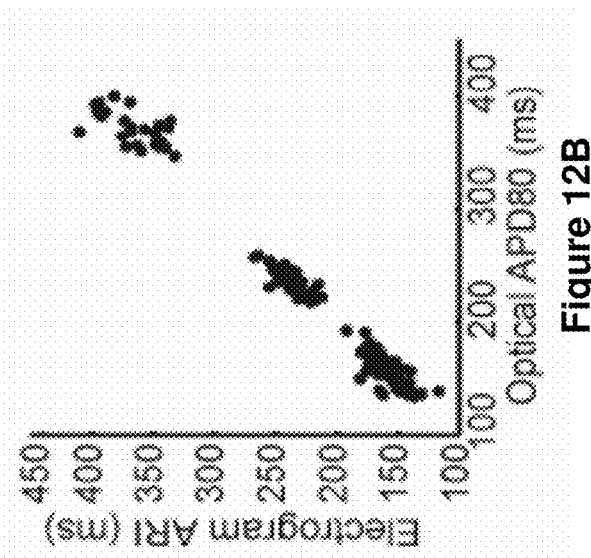
Figure 12A
Figure 12B
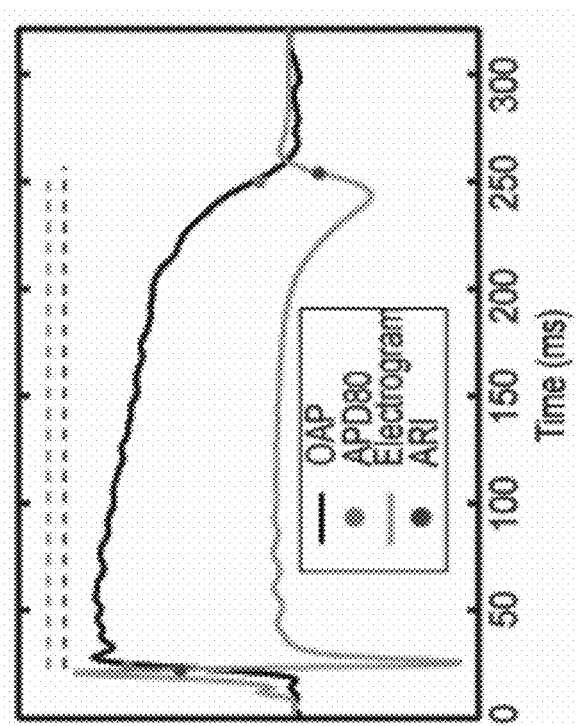
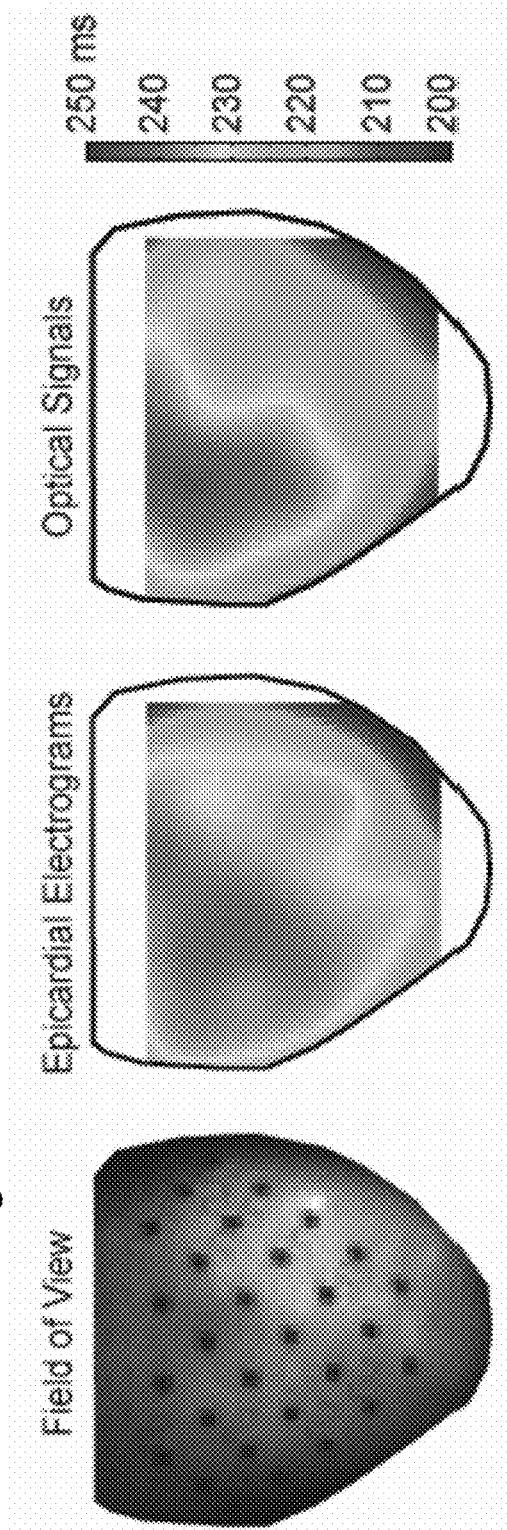
Figure 12C

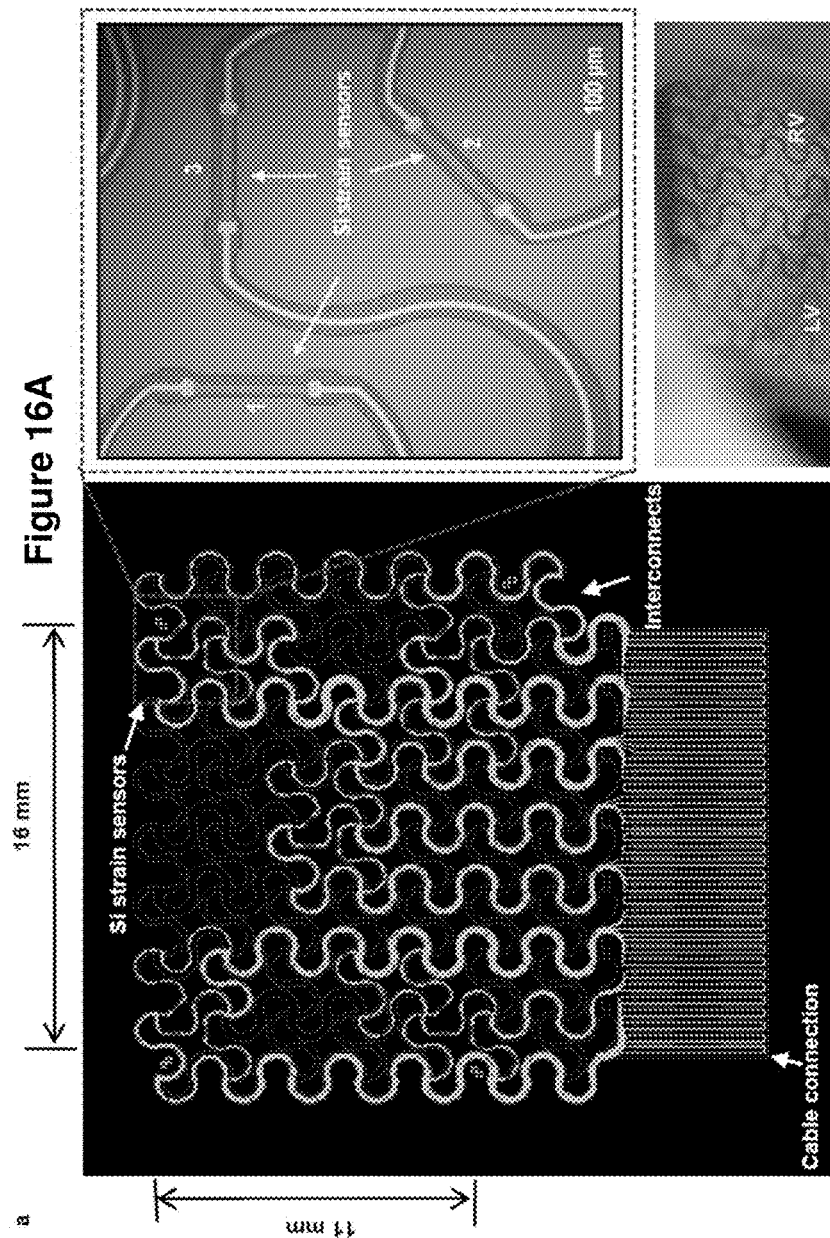
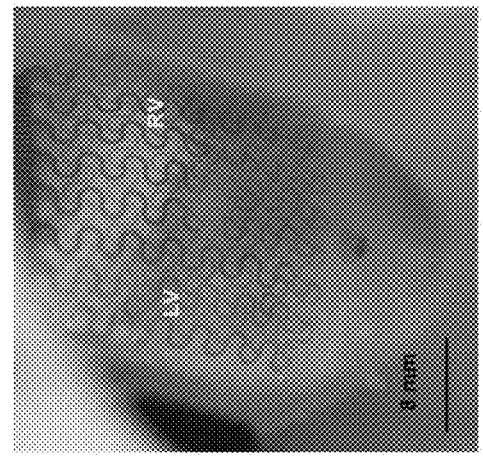
Figure 16A
Figure 16B

ORGAN MOUNTED ELECTRONICS

CROSS-REFERENCE TO RELATED APPLICATIONS

This application claims the benefit of U.S. Provisional Pat. App. 61/885,994, filed Oct. 2, 2013, U.S. Provisional Pat. App. 61/937,187, filed Feb. 7, 2014, and U.S. Provisional Pat. App. 62/003,786, filed on May 28, 2014, each of which is hereby incorporated by reference in its entirety.

STATEMENT REGARDING FEDERALLY SPONSORED RESEARCH OR DEVELOPMENT

This invention was made with governmental support under Award Nos. R01 HL115415, R01 HL114395 and R21 HL112278 awarded by the National Institutes of Health and Award No. DGE-1144245 awarded by the National Science Foundation. The government has certain rights in the invention.

BACKGROUND

Sudden cardiac arrest is a leading cause of death in developed countries. Many patients at risk for arrhythmic death have advanced structural heart disease, and preexisting non-lethal ventricular arrhythmias. In these and other cases, cardiac electrophysiologic (EP) characterization is useful to aid diagnosis and guide therapeutic interventions. Conventional clinical tools for this purpose have traditionally used sparse arrays of electrodes or point-contact catheters that probe potentials at the surface of cardiac tissue. During mapping, sensors are commonly maneuvered to record from discrete positions on the heart. These sequential local recordings are combined to render a composite representation of cardiac electrical activity over a region of interest. The iterative nature of this approach prolongs EP clinical procedures, thereby impeding real time mapping of transient abnormal rhythms. Alternative approaches have been developed to address these shortcomings including devices mounted on woven fabric networks matched to the shape of the ventricle and imaging techniques using fluorescence, nuclear magnetic resonance or ultrasound for cardiac EP mapping applications, even though each has significant shortcomings.

Despite explosive growth and innovation in the broader electronics industry, a key limitation of many state of the art EP devices is that they retain the simple electronics-tissue interface developed decades ago. Sensing and stimulating electrodes, for example, are commonly purely passive metallic contacts individually wired to separate, remote processing units that use traditional semiconductor wafer-based electronics. Rapid, high resolution EP mapping might be most effectively accomplished by embedding modern silicon-based integrated circuit (IC) technology directly at the tissue-electrode interface. Unfortunately the planar shapes and rigid, brittle mechanical properties associated with conventional ICs severely limit their non-destructive, intimate integration with the curvilinear, soft surfaces of cardiac tissue undergoing periodic deformation due to cardiac contractions.

Recently, a number of patents and publications have disclosed flexible, resilient and implantable electrode arrays for physiological mapping. For example, U.S. Patent Application Publication US 2007/0043416 discloses an implantable flexible elastic support with a plurality of electrodes held in contact with a target tissue. Similarly, International Patent Application Publication WO 98/49936 discloses a resilient electrode array for sensing signals associated with mapping and ablating heart tissue. U.S. Pat. No. 5,678,737 discloses an electrophysiology mapping system for displaying a 3D model of epicardial and endocardial surfaces with dynamic display of potential distribution data.

U.S. Patent Application Publication US 2003/0149456 discloses a multi-electrode cardiac lead adapter which incorporates a multiplexing circuit allowing for control by a conventional single lead cardiac pacing pulse generator. Similarly, U.S. Patent Application Publication US 2006/0173364 discloses a multichannel electrophysiology acquisition system which utilizes a digital multiplexing circuit built on a conventional integrated circuit. U.S. Pat. No. 6,666,821 discloses an implantable sensor array system with an associated protective member which prevents the sensors from interacting with the surrounding environment until it is disabled.

Other approaches for tissue mounted devices for cardiac EP mapping and epidermal electronics applications integrate high quality semiconductor materials in thin, flexible and/or stretchable form factors with 2D elastomeric substrates via dry transfer printing. Examples of this approach are described in US Patent Publication Nos. US 2013/0041235, published on Feb. 14, 2013, and US 2012/0157804, published on Jun. 21, 2012, which are hereby incorporated by reference in their entireties.

Despite these advances, there is a significant need for devices capable of 3D integration with large areas of biological tissue. Devices are needed that are capable of direct, conformal and non-invasive integration to allow for effective characterization and/or actuation of organ function. There is an unmet need, for example, for devices supporting multiparametric mapping capabilities for cardiac applications, inclusive but far beyond electrical sensing, in a conformal, high-resolution manner, which cannot be realized using conventional materials, device technologies or imaging modalities.

SUMMARY OF THE INVENTION

Provided herein are tissue-mounted and implantable devices and methods of making and using devices for medical diagnostic, sensing and therapeutic applications. The present invention provides medical devices and methods, for example, capable of establishing a continuous conformal interface with 3D surfaces of biological tissues, such as the 3D surfaces of organs like the heart. Devices and methods of certain embodiments provide the ability to monitor and/or control physical, chemical, biochemical and thermal properties of tissues in real time, for example, tissue surfaces having large areas and complex, nonplanar morphologies. Devices and methods of certain embodiments, for example, provide for high density, large area multiparametric mapping and/or actuation over 3D tissue surfaces using arrays of micro- and/or nano-scale sensors and actuators to spatially and temporally monitor and/or control a variety of physical, chemical and biological tissue parameters, such as temperature, pH, ion concentration, intrinsic fluorescence, spatial position, force, pressure, and electrophysiology and/or provide a variety of stimuli, such as heat, light, voltage and current in a spatially and temporally controlled manner. Multiparametric mapping and/or actuation may be implemented, for example, in a device comprising light emitting diodes and photodetectors for optical spectroscopy of intrinsic or extrinsic fluorescence, such as intrinsic fluorescence from an enzyme or compound, like NADH. In another embodiment, multiparametric mapping and/or actuation may be implemented in a device comprising both sensors and actuators, where at least a portion of the actuators provide a pacing signal while at least a portion of the sensors detect a response of the tissue to the pacing signal.

In some embodiments, the devices and methods of the invention utilize stretchable and flexible materials to conformally interface with large areas of tissue surfaces while completely immersed in fluid and without the use of sutures or adhesives. In certain embodiments, for example, the present devices combine stretchable, high quality (e.g., single crystalline, high purity, low defects, etc.) inorganic semiconductor structures and/or devices supported by an elastic membrane having a 3D geometry complementary to the shape of an organ to provide integration over a significant portion of the exterior surface of an organ, such as the epicardium of the heart. Advantageously, incorporation of stretchable materials in the present device configurations provide for the ability to form and maintain a conformal interface with the 3D surface of tissues undergoing physical displacement, including repetitive motion, for example during cardiac cycling. Biocompatible and bioinert materials are optionally used in the present devices in order to enable long-term, noninvasive monitoring and interfacing with biological tissues.

Devices and methods of the invention enable interfacing with large tissue surface areas, such as by enclosing a tissue within a device enclosure providing sensors and actuators at the interface between the tissue and the inner surface of the enclosure. For certain tissue configurations, a device enclosure of the present invention provides for the ability to conformally contact 70% or more, and optionally all, of a tissue's surface area, such as the external surface of an organ, muscle, vasculature, bone or other biological tissue body, thereby supporting application of the present devices for high density physiological characterization and/or stimulation on a system-level scale. Certain methods of the invention include preparation of a device enclosure using a three-dimensional model of an organ to form the shape of the device enclosure prior to deployment onto the tissue for interfacing. Use of three-dimensional models as device fabrication templates in the present invention provides for the ability to precisely control or minimize stresses and forces placed on a tissue when enclosed via a device enclosure, thus minimizing or reducing the risk of stress or damage to the tissue during interfacing due to excess pressure or force. In addition, use of three-dimensional models for fabrication of the present devices also enables overall device geometries providing a force directed toward the surface of the tissue necessary for maintaining conformal contact during physical displacement of the tissue, for example, by movement, expansion or contraction of an organ.

In a first aspect, the present invention provides devices for at least partially interfacing with an internal biological tissue, such as an organ, vasculature or bone. In a specific embodiment, a device of this aspect comprises: a flexible and stretchable substrate having an inner surface and an external surface, with the inner surface defining an enclosure to enclose the internal biological tissue; a flexible and stretchable electronic device or device component comprising one or more sensors, actuators or both supported by the inner surface of the flexible or stretchable substrate; the sensors, the actuators or both comprising one or more inorganic semiconductor components, one or more metallic components, or one or more inorganic semiconductor components and one or more metallic components. In embodiments, at least a portion of the inorganic semiconductor components, the metallic components or both has a thickness less than or equal to 500 microns, optionally for some embodiments less than or equal to 100 microns and optionally for some embodiments less than or equal to 10 microns. In embodiments, the flexible and stretchable substrate and the electronic device or device component provide a net bending stiffness of the system low enough such that the inner surface of the substrate is capable of establishing conformal contact with at least 70%, optionally at least 90%, of an outer surface of the internal biological tissue, optionally in continuous conformal contact with at least 70%, optionally at least 90%, of an outer surface of the internal biological tissue.

In an embodiment, the device at least partially surrounds, and optionally entirely surrounds, the internal biological tissue. In an embodiment, for example, at least a portion of the sensors, the actuators or both of the device are in physical contact, optical contact, thermal contact and/or fluid contact with the internal biological tissue. In a specific embodiment, for example, the flexible and stretchable substrate and the electronic device or device component provide a net flexural rigidity of the device less than or equal to $1 \times 10^{-4}$ Nm, optionally for some applications less than or equal to $0.5 \times 10^{-4}$ Nm and optionally for some applications less than or equal to $0.1 \times 10^{-4}$ Nm. These and other embodiments advantageously provide for the ability to conform to and interface with biological tissues having complex surface geometries and for the ability to interface with biological tissues that undergo complex motion and/or a change in shape as a function of time.

Devices and methods of the invention are particularly useful for sensing, characterizing and actuating a range of biological tissues due to the unique ability of the devices to conform to and maintain conformality with complex surface shapes characteristic of many types of organs, muscle, vasculature and/or bone. Various aspects of the disclosed devices provide for the ability to directly interface with a biological tissue, such as electronically, optically or thermally interface, and permit real-time investigation of biological tissues in vivo or ex vivo. In addition, the flexibility and stretchability of the devices provide the ability to interface with biological tissues that change shape and/or size as a function of time, thereby permitting spatial and temporal characterization and actuation of biological tissues as they move, change shape, grow and/or reduce in size or volume. For example, devices of the invention provide the ability to interface with muscle tissue as the muscle moves due to voluntary and/or involuntary muscle contractions, such as experienced by the heart during cardiac cycling. This aspect of the present systems and methods enables advanced systems-level diagnostic and therapeutic functionality for characterization and treatment of organ function.

For example, in various embodiments, the internal biological tissue is selected from the group consisting of: an organ, a blood vessel, muscle, a bone, any combinations thereof, and any portions thereof. In an embodiment, the biological tissue in conformal contact with the device is epicardium tissue. In some embodiments, for example, the internal biological tissue has a time-varying outer surface shape. For example, in a specific embodiment, the internal biological tissue comprises a heart having an outer surface corresponding to heart epicardium. In embodiments, the device in conformal contact with the internal biological tissue is immersed in a fluid. For example, the tissue is optionally immersed in a body fluid, a saline solution or water. In some embodiments, the device includes one or more barrier layers for preventing fluid, such as blood or water-based physiological ionic solution, from the environment from penetrating to an interior layer of the device. Such a configuration optionally also prevents or reduces leakage current from/to the sensors, actuators and/or electrical interconnects to tissue at the device interface and, thus, reduces or minimizes the risk of damage thereto due to current flow, electronic biasing, etc. Optionally, minimizing or reducing a leakage current maintains the sensing, actuating and/or interconnecting components in working electronic condition. In a specific embodiment, the internal biological tissue comprises an ex vivo explant. In an exemplary embodiment, the internal biological tissue comprises tissue within a living animal.

As described above, the devices and methods of the invention advantageously provide for the ability to conformally contact a biological tissue, such as a biological tissue that has a non-planar or non-uniformly curved shape or a biological tissue that changes shape and/or size as a function of time. In some embodiments, for example, the conformal contact provides physical contact, electrical contact, thermal contact or any combination of these between the device and a surface of a tissue. Various properties of the devices and device components disclosed herein provide for this ability to make conformal contact with biological tissues, including the overall properties of stretchability and flexibility, as well as material properties such as bending stiffness, elasticity, geometry, composition, thickness, etc. The conformal configuration of the devices described herein is aided, at least for some embodiments, by internal forces generated within the devices, such as elastic forces or restoring forces that act to return the devices to their neutral, strain-free, configurations. As stretchable and/or flexible devices and materials therein are stretched to an expanded configuration, elastic forces within the devices and materials can be used to maintain conformal contact with a surface underlying the device or material, particularly when the device is provided in an enclosed type geometry, such as a geometry that is used to surround another object.

In some embodiments, the flexible and stretchable substrate and electronic device or device component generates a contact force to maintain conformal contact with the outer surface of the internal biological tissue during use. For example, in one embodiment, the contact force is generated by an elastic force of the enclosure in an expanded state. For example, the enclosure is optionally expanded to an expanded state by stretching at least a portion of the flexible and stretchable substrate, while a restoring force resists the expansion and provides the elastic force in an attempt to return the enclosure to its neutral configuration where the flexible and stretchable substrate is in a strain-free configuration. In an exemplary embodiment, for example, the expanded state is an increase in a volume of the enclosure selected from the range of 1% and 100%, and optionally for some applications 10% and 100% to accommodate the internal biological tissue within the enclosure. In embodiments, conformal contact is maintained during deformation of the internal biological tissue within the enclosure. For example, as the biological tissue within the enclosure is moved, or expands or contracts, conformal contact is optionally maintained.

In embodiments, the contact force corresponds to a contact pressure that is sufficiently low to avoid an adverse physiological response from the internal biological tissue. In specific embodiments, for example, the contact pressure is greater than or equal to 10 Pa and less than or equal to 1 kPa. For some embodiments, the contact pressure is substantially uniformly distributed over an outer surface of the internal biological tissue in conformal contact with the flexible and stretchable substrate. Optionally, a peak pressure is less than or equal to 3 times the contact pressure averaged over the outer surface of the internal biological tissue in conformal contact with the flexible and stretchable substrate. In certain embodiments, the contact force varies with changes in internal biological tissue shape. For example, in some embodiments, the contact force is larger when the internal biological tissue shape expands and is smaller when the internal biological tissue shape contracts.

In embodiments, the enclosure has a shape complementary to an outer surface shape of the internal biological tissue, optionally a custom-formed shape using a model as a device fabrication template. In a specific embodiment, for example, the enclosure has a shape complementary to or mimicking that of an outer surface shape of a heart or another organ. In exemplary embodiments, the enclosure at least partially envelops, optionally entirely envelops, the internal biological tissue. In certain embodiments, openings are provided in the enclosure to allow an enveloped internal biological tissue to maintain physiological connection with a body, such as through blood vessels or other fluid or nervous system pathways.

Optionally, in embodiments, the enclosure has an enclosure volume that is selected from a range that is greater than or equal to 0.1 $cm^3$ and less than or equal to 2,000 $cm^3$. Optionally, in embodiments, the enclosure has an enclosure surface area that is selected from a range that is greater than or equal to 100 $\mu m^2$ and less than or equal to 800 $cm^2$. In an embodiment, for example, the device has an enclosure characterized by an enclosure volume and surface area corresponding to a selected target tissue, such as the heart or other organ of a human subject. For example, in one embodiment, the enclosure volume varies to accommodate volume or surface shape changes in the internal biological tissue over time while the contact force remains sufficiently high to maintain conformal contact and sufficiently low to avoid an adverse physiological response. For example, in one embodiment, the enclosure area varies to accommodate area or surface shape changes in the internal biological tissue over time while the contact force remains sufficiently high to maintain conformal contact and sufficiently low to avoid an adverse physiological response.

Devices and methods of the invention provide for the ability to investigate and interact with biological tissues using one or more sensors, actuators or both. As used herein, the term sensor relates to an electronic device or device component used to probe a physical quantity or property, an electrical or magnetic property, an optical property, a thermal property or a chemical property. As used herein, the term actuator relates to an electronic device or device component used to control a physical quantity or property, an electrical or magnetic property, an optical property, a thermal property or a chemical property. In various embodiments, sensors and actuators used with the devices and methods described herein allow for real-time measurement and control of various properties of biological tissues.

In various embodiments, the flexible and stretchable electronic device or device component comprises an array of sensors, an array of actuators, or an array of sensors and actuators. Optionally, for some embodiments, the sensors, actuators or both the sensors and the actuators move synchronously with internal biological tissue that underlays the sensors, the actuators or both the sensors and the actuators.

A variety of actuators are useful with the devices and methods of the present invention. For example, in embodiments, each actuator in a device or used in a method is independently selected from the group consisting of an electrode, a heat source, a piezoelectric element, an acoustic element, a source of RF energy, a magnetic actuator, a source of electromagnetic radiation, a laser, a light emitting diode and arrays and combinations thereof.

A variety of sensors are useful with the devices and methods of the present invention. For example, in embodiments, each sensor in a device or used in a method is independently selected from the group consisting of an electrode, a strain sensor, a capacitance sensor, a temperature sensor, a pressure sensor, a motion sensor, a position sensor, a displacement sensor, an acceleration sensor, a force sensor, a chemical sensor, a pH sensor, a capacitive sensor, an optical sensor, a photodetector, an imaging system and any arrays and combinations thereof.

In exemplary embodiments, the electronic device or device component comprises both sensors and actuators. For example in some embodiments, the electronic device or device component comprises 2 to 10,000 of the sensors, the actuators or both. In exemplary embodiments, the flexible and stretchable electronic device or device component is multifunctional. For example, in some embodiments, the electronic device or device component comprises at least 3 different types of sensors, actuators or both.

In order to provide stretchability and flexibility to the devices of the invention, certain features are optionally incorporated to allow the sensors and actuators of the devices to undergo relative motion while also maintaining useful and reliable electrical conductivity. For example, in some embodiments, the sensors, actuators or both are electrically connected via a network of stretchable interconnects, such as mesh or serpentine electrical interconnects. In some embodiments, the stretchable interconnects are at least partially free-standing or have a tethered geometry. In some embodiments, for example, the sensors, actuators or both are provided in an open mesh geometry. In some embodiments, for example, the sensors, actuators or both are provided in an island—bridge geometry, for example, comprising ridged semiconductor devices or device components supported by the elastic substrate and interconnected via bridge structures such as stretchable interconnects. Optionally, for certain embodiments, the sensors, actuators, or both have a spatial density of between about 1 cm$^{-2}$ to 1 mm$^{-2}$.

In a specific embodiment, the flexible and stretchable electronic device or device component comprises electrodes for mapping internal biological tissue electrical activity. For example, in some embodiments, the electrodes are positioned in an array and spaced between 1 µm and 5 mm apart from each other, optionally for some applications between 1 mm and 5 mm apart from each other. Optionally, in embodiments, the electrodes are distributed over a surface area that is greater than or equal to 0.1 mm$^2$ and less than or equal to 1000 mm$^2$. In an exemplary embodiment, the electrodes comprise an array distributed over the flexible and stretchable substrate to monitor electrical activity on both an anterior and posterior surface of a heart.

In certain embodiments, the sensors comprise pH sensors. The use of pH sensors, in embodiments, advantageously provides for the ability to monitor or sense an indication of metabolic state of internal biological tissue underlying the sensors. For example, in one embodiment, the pH sensors comprise an iridium oxide (IrO$_x$) layer provided on an electrode surface. In an embodiment, for example, the pH sensors, optionally in combination with one or more other sensors, provide for measurement of pH, transmembrane potential, calcium transient signals or any combination of these.

In certain embodiments, the sensors comprise an array of temperature sensors, for example an array of temperature sensors for monitoring a spatial distribution of temperature. In one embodiment, for example, each temperature sensor in the array of temperature sensors independently comprises a serpentine electrically conductive nanowire having an electrical resistance that varies with changes in temperature. For example, in embodiments, a length, resistance and/or conductance of each temperature serpentine electrically conductive nanowire is selected so as to provide the ability to independently measure temperature at a variety of spatial locations.

In certain embodiments, the actuators comprise one or more thermal actuators, for example, for spatially controlled heating of the internal biological tissue. Optionally, the spatially controlled heating is independently monitored by an array of temperature sensors, such as described above.

In certain embodiments, the one or more sensors comprise a strain sensor. For example, in one embodiment, a strain sensor comprises a plurality of p-doped Si piezoresistors oriented in different directions relative to each other, each of the piezoresistors electrically connected to serpentine electrical interconnects. In a specific embodiment, a device of this aspect comprises three piezoresistors arranged in a rosette configuration, with two piezoresistors aligned in a <110> crystalline direction of the Si and a third piezoresistor aligned in a <100> crystalline direction of the Si. Such a configuration optionally provides for the ability to compensate for and/or correct for temperature variations in piezoeresistive strain measurements.

In certain embodiments, the electronic device or device component comprises a plurality of optical sources. For example, in one embodiment, the optical sources comprise one or more light emitting diodes (LEDs). Optionally, in embodiments, the LEDs each independently have a thickness less than 10 µm and a surface area that is less than 0.25 mm$^2$. Optionally, in embodiments, the LEDs comprise aluminum gallium indium phosphide (AlInGaP). In a specific embodiment, the optical sources provide optical mapping of a surface of the internal biological tissue. For example, in one embodiment, the optical sources are for monitoring and mapping action potential of the internal biological tissue underlying the optical sources.

In an embodiment, the devices of the invention are implantable devices, such as implantable tissue mounted devices. In an embodiment, for example, a device of the invention encloses at least 70% of an organ, and optionally for some applications encloses at least 90% of an organ. In an embodiment, the invention provides an optically transparent device, for example, that is transparent for at least a portion of wavelengths in the visible region of the electromagnetic spectrum, thereby allowing visualization of at least a portion of the underlying biological tissue. In an embodiment, for example, the inner surface of the substrate establishes a continuous physical contact with the at least 70% of the outer surface of the internal biological tissue, and optionally for some applications at least 90% of the outer surface of the internal biological tissue. In an embodiment, for example, the inner surface of the substrate establishes a continuous physical contact with an area of the outer surface of the internal biological tissue selected from the range of 100 µm$^2$ to 800 cm$^2$. In an embodiment, for example, the flexible and stretchable substrate and the electronic device provide a net bending stiffness of the device less than or equal to 1 nN m, optionally less than or equal to 0.5 nN m. In an embodiment, for example, the flexible and stretchable substrate and the electronic device provide a net bending stiffness of the device selected over the range of 0.1 to 1 nN m, optionally 0.1 to 0.5 nN m, optionally 0.2 nN m to 1 nNm.

A variety of flexible and stretchable substrates are useful with the devices and methods described herein. The properties, geometries and chemical identity of the flexible and stretchable substrates are optionally selected to allow the devices to adopt conformal configurations, to be biocompatible with or otherwise able to interact with a biological tissue. In an embodiment, the flexible and stretchable substrate comprises a low modulus elastomer. For example, in embodiments, the flexible and stretchable substrate comprises a material selected from the group consisting of: a polymer, an inorganic polymer, an organic polymer, a plastic, an elastomer, a biopolymer, a thermoset, a rubber, a fabric, a paper and any combination of these. In an embodiment, the flexible and stretchable substrate comprises a low modulus elastomer.

In some embodiments, for example, the flexible and stretchable substrate has a thickness that is less than or equal to 10 mm, optionally a thickness that is less than or equal to 1 mm and optionally a thickness that is less than or equal to 500 µm. In some embodiments, for example, the flexible and stretchable substrate has an average modulus less than or equal to 500 kPa. In some embodiments, for example, the flexible and stretchable substrate has an average modulus selected over the range of 0.5 kPa to 500 kPa. In some embodiments, for example, the flexible and stretchable substrate has an average modulus equal to or less than 50 times the average modulus of the internal biological tissue at the interface with the inner surface of the flexible and stretchable substrate.

In exemplary embodiments, the flexible and stretchable substrate forms a closed surface over the internal biological tissue. In exemplary embodiments, the flexible and stretchable substrate comprises a biocompatible material or a bioinert material.

The devices provided herein are optionally further described in terms of the geometry and properties of the electronic device or device component. In an embodiment, for example, the sensors, the actuators or both comprise one or more inorganic semiconductor structures, such as single crystalline inorganic semiconductor structures, such as thin film semiconductor structures. In an embodiment, for example, the sensors, the actuators or both comprise one or more metallic structures, such as thin film metallic structures. For example, the one or more inorganic semiconductor components or one or more metallic conductor components may independently comprise an ultrathin structure. For example, the one or more inorganic semiconductor components or one or more metallic conductor components may independently comprise one or more thin film structures; independently have a thickness selected from the range of 10 nm to 100 µm; or independently have a thickness less than or equal to 100 nm. In an aspect, any of the devices may comprise one or more inorganic semiconductor components, such as an inorganic semiconductor component independently comprising: a nanomembrane structure, a polycrystalline semiconductor material, single crystalline semiconductor material or a doped polycrystalline or single crystalline semiconductor material. To provide good flexibility or stretchability, at least one of the inorganic semiconductor components or one or more metallic conductor components is optionally a flexible or a stretchable structure. The flexible or stretchable structure may be an interconnect that connects island structures, such as island structures that tend to be relatively less stretchable or flexible. In this manner, the interconnects may accommodate stresses and strains associated with stretching or flexing. In an aspect, at least one of the inorganic semiconductor components or one or more metallic conductor components is a nanoribbon, a nanomembrane, a nanowire, a transistor channel, a diode, a p-n junction, a photodiode, a light emitting diode, a laser or a combination of these. In an aspect, at least one of the inorganic semiconductor components or one or more metallic conductor components has a Young's modulus selected from the range of 0.5 MPa to 10 GPa. In an aspect, at least one of the inorganic semiconductor components or one or more metallic conductor components has a net bending stiffness less than or equal to $1 \times 10^8$ GPa $\mu m^4$.

In another aspect, provided are methods of making devices. For example, in one embodiment, the present invention provides a method of making a device for interfacing with an internal biological tissue. An exemplary method embodiment of this aspect comprises the steps of: transferring a flexible and stretchable electronic device or device component to a flexible and stretchable substrate, wherein the flexible and stretchable electronic device or device component comprises one or more sensors, actuators or both; wherein the sensors, the actuators or both comprise one or more inorganic semiconductor components, one or more metallic components, or both one or more inorganic semiconductor components and one or more metallic components; wherein at least a portion of the inorganic semiconductor components, metallic components or both has a thickness less than or equal to 500 microns; and shaping the flexible and stretchable substrate to substantially match a three-dimensional surface shape of the internal biological tissue, thereby making an enclosure for receiving and enclosing at least 70% of an outer surface of the internal biological tissue. In various embodiments, methods of this aspect comprise methods for making devices for interfacing with an internal biological tissue, such as any of the above described device embodiments.

In a specific embodiment, the sensors, actuators or both are positioned on an enclosure-forming surface of the flexible and stretchable substrate. In an exemplary embodiment, a method of this aspect further comprises the steps of applying the flexible and stretchable electronic device or device component to an outer surface of the biological tissue; and casting a flexible and stretchable layer against the flexible and stretchable electronic device or device component applied to the outer surface of the biological tissue.

In a specific embodiment, the enclosure has a dimension that is less than a dimension of the internal biological tissue to be enclosed by the enclosure, thereby generating a contact force between the device and the internal biological tissue to maintain conformal contact during use due to an elasticity of the flexible and stretchable substrate when in an expanded state. In exemplary embodiments, for example, the contact force corresponds to a contact pressure that is selected from a range that is greater than or equal to 10 Pa and less than or equal to 1 kPa. In one embodiment, the contact force corresponds to a contact pressure that does not generate an adverse physiological response from the internal biological tissue during use of the device.

In another aspect, the present invention provides methods of interfacing with a tissue, such as an internal biological tissue. In an embodiment, an exemplary method of this aspect comprises the steps of: providing a device comprising a flexible and stretchable electronic device or device component comprising one or more sensors, actuators or both supported by an inner surface of a flexible or stretchable substrate; the sensors, the actuators or both comprising one or more inorganic semiconductor components, one or more metallic components, or both one or more inorganic semiconductor components and one or more metallic components; wherein at least a portion of the inorganic semiconductor components, the metallic components or both has a thickness less than or equal to 500 microns; and wherein the inner surface of the flexible or stretchable substrate defines an enclosure; expanding the enclosure to an expanded state; and enclosing the internal biological tissue within the enclosure in the expanded state, thereby generating an elastic contact force to conformally mount and enclose the internal biological tissue to the device and interface with the internal biological tissue, wherein the device encloses at least 70% of an outer surface of the internal biological tissue. In various embodiments, the methods of this aspect comprise providing a device for interfacing with an internal biological tissue, such as any of the above described device embodiments.

In a specific embodiment, the conformally mounting and enclosing step further comprises: generating an average contact pressure between the device and the mounted and enclosed internal biological tissue that is sufficiently high to maintain conformal contact during use of the device without causing an adverse physiological response from the internal biological tissue.

In certain embodiments, the invention encompasses administering an implantable or surface mounted device to a patient or subject. A "patient" or "subject", used equivalently herein, refers to an animal. In particular, an animal refers to a mammal, preferably a human. The subject can either: (1) have a condition able to be monitored, diagnosed, prevented and/or treated by administration of an implantable or tissue mounted device of the invention; or (2) be susceptible to a condition that is able to be monitored, diagnosed, prevented and/or treated by administering an implantable or tissue mounted device of the invention. In an embodiment, a method of this aspect further comprises administering a device of the invention to a subject in need of treatment, for example, a subject having a disease, propensity for a disease or other pathological condition. The present devices and methods are particularly useful for treatment and management of a range of diseases or other pathological conditions including cardiac diseases and disorders, such as arrhythmias, ischemia, hypoxia and heart failure.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 2A: Graphical depiction of the key steps in device design and fabrication. FIG. 2B: Images of a representative 3D-MIM integrated on a Langendorff-perfused rabbit heart. FIG. 2C: Magnified views of the functional elements in conformal contact with the epicardium.

FIG. 3A: Calculated pressure distribution induced by a device with total thickness of 150 μm and effective Young's modulus of 60 kPa under various conditions of volume expansion of a heart geometry. FIG. 3B: FEM and analytical results of average pressure as functions of volume expansion (left), thickness (middle) and Young's modulus (right) of the membrane.

FIG. 4A, FIG. 4B, FIG. 4C and FIG. 4D provide an overview of high-density electrical mapping. FIG. 4A: Representative optical and electrical signals acquired simultaneously from the corresponding colored electrode locations on a Langendorff-perfused rabbit heart. FIG. 4B: Top: schematic illustration of a representative optical action potential (OAP), unipolar electrogram (EG) and position of the activation time; Bottom: correlation of electrical and optical activation times for hearts tested in a variety of states. FIG. 4C: Interpolated spatial activation maps determined from the electrical and optical measurements. FIG. 4D: 3D mapping of electrical signaling from both the anterior and posterior surfaces of the heart.

FIG. 5A, FIG. 5B, FIG. 5C, FIG. 5D, FIG. 5E and FIG. 5F demonstrate high-density pH mapping with simultaneous optical mapping of transmembrane potential and calcium transients. FIG. 5A: 3D-MIM with pH sensors array integrated on a Langendorff-perfused rabbit heart with 2 pH sensors highlighted and values displayed in FIG. 5B. FIG. 5B: Temporal change in pH during 30 minutes of no-flow ischemia followed by 30 minutes of reperfusion. FIG. 5C: Representative far-field ECG during baseline and reperfusion induced VT. FIGS. 5D-5F: pH map of 32 sensors (left), representative transmembrane potential and calcium transient signals (middle), and APD70-CaT70 maps (right) at baseline (FIG. 5D), 10 minutes of no-flow ischemia (FIG. 5E), and 20 minutes of reperfusion (FIG. 5F).

FIG. 6A, FIG. 6B, FIG. 6C and FIG. 6D demonstrate high-density temperature and strain sensing, and imaging using integrated μ-ILEDs. FIG. 6A: Application of a 3D-MIM for temperature monitoring during cold perfusion. FIG. 6B: Temperature measurements during an ablation experiment. FIG. 6C: Responses of a Si strain sensor under representative physiological conditions, compared with simultaneous ECG recordings. FIG. 6D: Left: image of a 3D-MIM with μ-ILEDs array in optical mapping experiments. Inset shows a magnified view of area around a representative μ-ILED. Right: comparison of optical signals from a representative pixel (blue dot on the left inset) recorded during excitation using μ-ILEDs on 3D-MIM and external optical excitation, respectively.

FIG. 7A: Schematic illustration of the partial axisymmetric ellipsoid with the lengths a and b of semiprincipal axes for the analytic model. FIG. 7B: The comparison of the stiffness of the 3D-MIM with and without electronic devices along two directions.

FIG. 8A: A chronological comparison of the pressure waveform at the aorta and electrophysiological indicators of ischemia during the working heart preparation with and without the 3D-MIMs on the heart. FIG. 8B: Example traces at the beginning and end of the stability hour for the 3D-MIM group and the control group.

FIG. 11A, FIG. 11B and FIG. 11C provide a comparison of signal quality of 3D-MIMs electrophysiological measurements under beating and arrested heart conditions. Surface electrogram recordings under both beating (FIG. 11A) and arrested (FIG. 11B) conditions capture various morphologies of the QRS and T waves. FIG. 11C: Comparison of the signal to noise ratio (SNR) of the measurements.

FIG. 12A, FIG. 12B and FIG. 12C demonstrate spatial mapping of repolarization p parameters with 3D-MIMs. FIG. 12A: Representative electrical trace from the device overlaid with a corresponding optical trace for validation defines activation recovery interval (ARI) from max –dV/dt to the max dV/dt after the QRS complex and defines action potential duration to 80% repolarization (APD80) from max dV/dt to 80% recovery. FIG. 12B: Correlation between the activation recovery interval from the electrograms and the corresponding optical action potential duration from a variety of conditions. FIG. 12C: Representative spatial reconstruction of repolarization parameters with the electrical device and the optical mapping.

FIG. 16A and FIG. 16B provide images of devices incorporating a Si strain sensor array. FIG. 16A provides an overview of the design and optical microscope image of the Si strain sensor array, where the inset provides an optical microscope image of 3 p-doped Si piezoresistors arranged in a rosette configuration. FIG. 16B provides an image of a 3D-MIM with Si strain sensor array integrated on a Langendorff-perfused rabbit heart.

DETAILED DESCRIPTION OF THE INVENTION

Figure 1A:
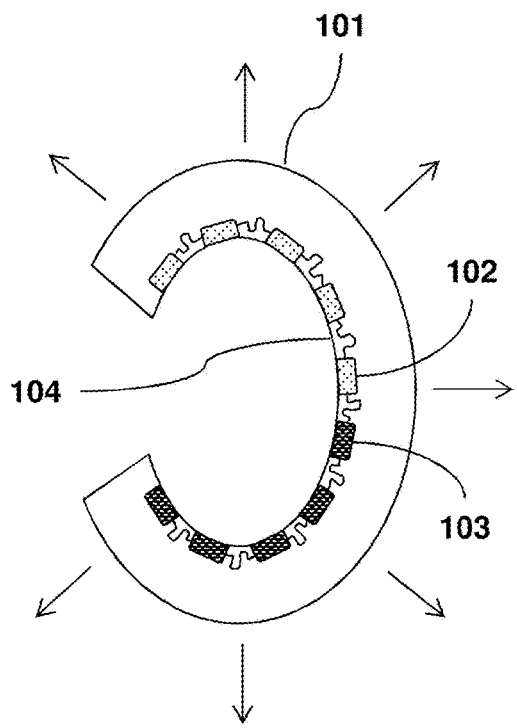
FIG. 1A, FIG. 1B, FIG. 1C, FIG. 1D, FIG. 1E, FIG. 1F and FIG. 1G provide schematic illustrations giving an overview of method embodiments of the invention for interfacing with a tissue.
Figure 1B:
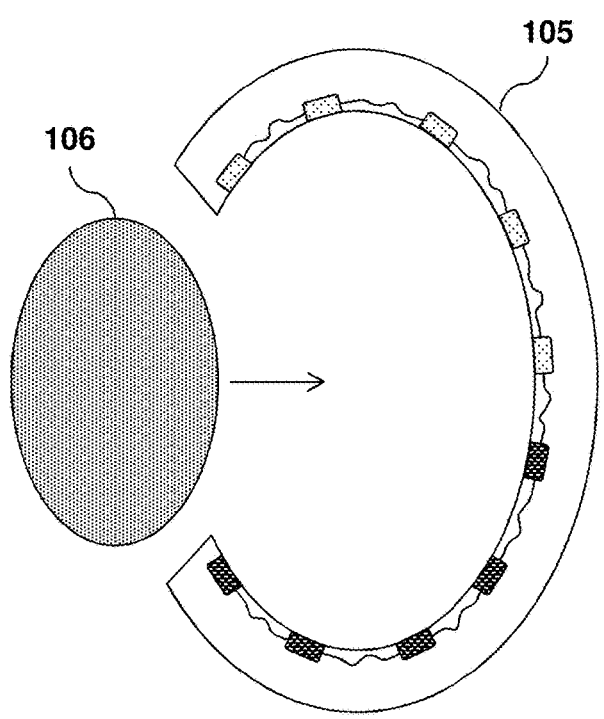

In general, the terms and phrases used herein have their art-recognized meaning, which can be found by reference to standard texts, journal references and contexts known to those skilled in the art. The following definitions are provided to clarify their specific use in the context of the invention.

The terms "flexible" and "bendable" are used synonymously in the present description and refer to the ability of a material, structure, device or device component to be deformed into a curved or bent shape without undergoing a transformation that introduces very high levels of strain, such as strain characterizing the failure point of a material, structure, device or device component. In an exemplary embodiment, a flexible material, structure, device or device component may be deformed into a curved shape without introducing strain larger than or equal to 5%, for some applications larger than or equal to 1%, and for yet other applications larger than or equal to 0.5% in strain-sensitive regions. A used herein, some, but not necessarily all, flexible structures are also stretchable. A variety of properties provide flexible structures (e.g., device components) of the invention, including materials properties such as a low modulus, bending stiffness and flexural rigidity; physical dimensions such as small average thickness (e.g., less than 100 microns, optionally less than 10 microns and optionally less than 1 micron) and device geometries such as thin film and mesh geometries.

"Stretchable" refers to the ability of a material, structure, device or device component to be strained without undergoing fracture. In an exemplary embodiment, a stretchable material, structure, device or device component may undergo strain larger than 0.5% without fracturing, for some applications strain larger than 1% without fracturing and for yet other applications strain larger than 3% without fracturing. A used herein, many stretchable structures are also flexible. Some stretchable structures (e.g., device components) are engineered to be able to undergo compression, elongation and/or twisting so as to be able to deform without fracturing. Stretchable structures include thin film structures comprising stretchable materials, such as elastomers; bent structures capable of elongation, compression and/or twisting motion; and structures having an island—bridge geometry. Stretchable device components include structures having stretchable interconnects, such as stretchable electrical interconnects.

"Implantable" refers to a device that is positioned on tissue or inserted into tissue, such as for interfacing with an exterior or interior portion of tissue that is not surface-accessible. "Interfacing" with tissue refers to sensing, measuring, actuating and/or controlling one or more parameters associated with the tissue. For example, a physical parameter such as temperature or electrical potential may be measured and/or controlled. Similarly, a biological parameter, such as concentration of a biologic material, cell surface receptor blocking/activation, membrane porosity, may be measured and/or controlled. Accordingly, interfacing is used broadly to refer to passive measurement of a tissue or cell property, active control of a tissue or cell property, or both.

"Target tissue" refers to a tissue that a device makes conformal contact with and, more specifically, a specific portion of tissue for which interfacing is desired. Target tissue may refer to internal biological tissue. Target tissue is used broadly and in some embodiments refers to an exterior or interior surface of a tissue or organ that is not visually or physically accessible without opening up of a body of a subject.

"Internal biological tissue" refers to cells, tissue or organs of a subject or patient that is not normally present at an exterior surface of the patient or subject and is generally only accessible by opening up the body or skin of the patient or subject. In embodiments, internal biological tissue includes, but is not limited to, organs, muscles, blood vessels, vasculature, bones, epithelial tissue, connective tissue, nervous tissue or neural tissue. Optionally, internal biological tissue is target tissue. In some embodiments, internal biological tissue is removed from a living subject or patient and is referred to herein as "ex vivo" tissue. The term ex vivo contrasts with "in vivo", which refers to biological tissue that is present within a living subject or patient.

"Substrate" refers to a material, layer or other structure having a surface, such as a receiving surface, that is capable of supporting one or more components or devices. A component that is "bonded" to the substrate refers to a component that is in physical contact with the substrate and unable to substantially move relative to the substrate surface to which it is bonded. Unbounded or unbonded components or portions of a component, in contrast, are capable of substantial movement relative to the substrate. In an embodiment, the invention provides devices wherein one or more inorganic semiconductor components, one or more metallic conductor components and/or one or more dielectric components are directly or indirectly bonded to the substrate, for example, via a bonding layer, an adhesive layer or other intermediate layer positioned between the inorganic semiconductor components and/or metallic conductor components and the substrate. The direct bonding to the substrate includes in some embodiments components that are embedded, either partially or completely, in the substrate.

"Functional layer" refers to a layer that imparts some functionality to the device. For example, the functional layer may contain semiconductor components, metallic components, dielectric components, optical components, piezoelectric components, etc. that form an electronic device. A "functional electronic device" refers to an electronic device, such as a sensor or actuator that interfaces with tissue with which the device is in contact. The functional layer may comprise multiple layers, such as multiple semiconductor layers, metallic layers or dielectric layers separated by support layers. The functional layer may comprise a plurality of patterned elements, such as interconnects running between electrodes or islands. The functional layer may be heterogeneous or may have one or more properties that are inhomogeneous. "Inhomogeneous property" refers to a physical parameter that can spatially vary, thereby effecting the position of a neutral mechanical plane within a multilayer device to thereby increase the bendability or deformability of the device.

"Semiconductor" refers to any material that is an insulator at a very low temperature, but which has an appreciable electrical conductivity at a temperature of about 300 Kelvin. In the present description, use of the term semiconductor is intended to be consistent with use of this term in the art of microelectronics and electronic devices. Useful semiconductors include those comprising elemental semiconductors, such as silicon, germanium and diamond, and compound semiconductors, such as group IV compound semiconductors such as SiC and SiGe, group III-V semiconductors such as AlSb, AlAs, AlN, AlP, BN, BP, BAs, GaSb, GaAs, GaN, GaP, InSb, InAs, InN, and InP, group III-V ternary semiconductors such as $Al_xGa_{1-x}As$, group II-VI semiconductors such as CsSe, CdS, CdTe, ZnO, ZnSe, ZnS, and ZnTe, group I-VII semiconductors such as CuCl, group IV-VI semiconductors such as PbS, PbTe, and SnS, layer semiconductors such as $PbI_2$, $MoS_2$, and GaSe, and oxide semiconductors such as CuO and $Cu_2O$. The term semiconductor includes intrinsic semiconductors and extrinsic semiconductors that are doped with one or more selected materials, including semiconductors having p-type doping materials and n-type doping materials, to provide beneficial electronic properties useful for a given application or device. The term semiconductor includes composite materials comprising a mixture of semiconductors and/or dopants. Specific semiconductor materials useful for some embodiments include, but are not limited to, Si, Ge, Se, diamond, fullerenes, SiC, SiGe, SiO, $SiO_2$, SiN, AlSb, AlAs, AlIn, AlN, AlP, AlS, BN, BP, BAs, $As_2S_3$, GaSb, GaAs, GaN, GaP, GaSe, InSb, InAs, InN, InP, CsSe, CdS, CdSe, CdTe, $Cd_3P_2$, $Cd_3As_2$, $Cd_3Sb_2$, ZnO, ZnSe, ZnS, ZnTe, $Zn_3P_2$, $Zn_3As_2$, $Zn_3Sb_2$, $ZnSiP_2$, CuCl, PbS, PbSe, PbTe, FeO, FeS$_2$, NiO, EuO, EuS, PtSi, TlBr, CrBr$_3$, SnS, SnTe, PbI$_2$, MoS$_2$, GaSe, CuO, Cu$_2$O, HgS, HgSe, HgTe, HgI$_2$, MgS, MgSe, MgTe, CaS, CaSe, SrS, SrTe, BaS, BaSe, BaTe, SnO$_2$, TiO, TiO$_2$, Bi$_2$S$_3$, Bi$_2$O$_3$, Bi$_2$Te$_3$, BiI$_3$, UO$_2$, UO$_3$, AgGaS$_2$, PbMnTe, BaTiO$_3$, SrTiO$_3$, LiNbO$_3$, La$_2$CuO$_4$, La$_{0.7}$Ca$_{0.3}$MnO$_3$, CdZnTe, CdMnTe, CuInSe$_2$, copper indium gallium selenide (CIGS), HgCdTe, HgZnTe, HgZnSe, PbSnTe, Tl$_2$SnTe$_5$, Tl$_2$GeTe$_5$, AlGaAs, AlGaN, AlGaP, AlInAs, AlInSb, AlInP, AlInAsP, AlGaAsN, GaAsP, GaAsN, GaMnAs, GaAsSbN, GaInAs, GaInP, AlGaAsSb, AlGaAsP, AlGaInP, GaInAsP, InGaAs, InGaP, InGaN, InAsSb, InGaSb, InMnAs, InGaAsP, InGaAsN, InAlAsN, GaInNAsSb, GaInAsSbP, and any combination of these. Porous silicon semiconductor materials are useful for aspects described herein. Impurities of semiconductor materials are atoms, elements, ions and/or molecules other than the semiconductor material(s) themselves or any dopants provided to the semiconductor material. Impurities are undesirable materials present in semiconductor materials which may negatively impact the electronic properties of semiconductor materials, and include but are not limited to oxygen, carbon, and metals including heavy metals. Heavy metal impurities include, but are not limited to, the group of elements between copper and lead on the periodic table, calcium, sodium, and all ions, compounds and/or complexes thereof.

A "semiconductor component" broadly refers to any semiconductor material, composition or structure, and expressly includes high quality single crystalline and polycrystalline semiconductors, semiconductor materials fabricated via high temperature processing, doped semiconductor materials, inorganic semiconductors, and composite semiconductor materials.

A "component" is used broadly to refer to an individual part of a device. An "interconnect" is one example of a component, and refers to an electrically conducting structure capable of establishing an electrical connection with another component or between components. In particular, an interconnect may establish electrical contact between components that are separate. Depending on the desired device specifications, operation, and application, an interconnect is made from a suitable material. Suitable conductive materials include semiconductors and metallic conductors.

Other components include, but are not limited to, thin film transistors (TFTs), transistors, diodes, electrodes, integrated circuits, circuit elements, control elements, photovoltaic elements (e.g. solar cell), sensors, light emitting elements, actuators, piezoelectric elements, piezoresistive elements, receivers, transmitters, microprocessors, transducers, islands, bridges and combinations thereof. Components may be connected to one or more contact pads as known in the art, such as by metal evaporation, wire bonding, and application of solids or conductive pastes, for example. Electronic devices of the invention may comprise one or more components, optionally provided in an interconnected configuration.

"Stacked configuration" refers to an arrangement of various layers and substrates having coincident surface areas, with adjacent layers or substrates positioned on top of each other. In some embodiments, for example, flexible and stretchable electronic device or device components of the present invention are composite structures having a stacked configuration, for example, including one or more semiconductor layers, metallic layers, or dielectric layers. In this manner, multiple functionality can be achieved by stacking multiple functional layers on top of each other, without adversely affecting the device form factor or packaged shape. For example, use of ultra-thin functional layers ensures a stacked device remains extremely thin. This is advantageous, for example, to provide devices that are conformable to complex 3D surfaces.

"Neutral mechanical plane" (NMP) and "neutral mechanical surface" (NMS) refer to an imaginary plane or surface existing in the lateral, b, and longitudinal, l, directions of a device. The NMP or NMS are less susceptible to bending stress than other planes or surfaces of the device that lie at more extreme positions along the vertical, h, axis of the device and/or within more bendable layers of the device. Thus, the position of the NMP or NMS is determined by both the thickness of the device and the materials forming the layer(s) of the device. In an embodiment, a device of the invention includes one or more inorganic semiconductor components, one or more metallic conductor components or one or more inorganic semiconductor components and one or more metallic conductor components provided coincident with, or proximate to, the neutral mechanical plane of the device. "Proximate" refers to the relative position of two or more objects, planes or surfaces, for example a NMP or NMS that closely follows the position of a layer, such as a functional layer, substrate layer, or other layer while still providing desired flexibility or stretchability without an adverse impact on the strain-sensitive material physical properties. In general, a layer having a high strain sensitivity, and consequently being prone to being the first layer to fracture, is located in the functional layer, such as a functional layer containing a relatively brittle semiconductor or other strain-sensitive device element. A NMP or NMS that is proximate to a layer need not be constrained within that layer, but may be positioned proximate or sufficiently near to provide a functional benefit of reducing the strain on the strain-sensitive device element when the device is folded.

"Coincident" refers to the relative position of two or more objects, planes or surfaces, for example a surface such as a neutral mechanical plane that is positioned within or is adjacent to a layer, such as a functional layer, substrate layer, or other layer. In an embodiment, a neutral mechanical plane is positioned to correspond to the most strain-sensitive layer or material within the layer.

"Proximate" refers to the relative position of two or more objects, planes or surfaces, for example a neutral mechanical plane that closely follows the position of a layer, such as a functional layer, substrate layer, or other layer while still providing desired conformability without an adverse impact on the strain-sensitive material physical properties. "Strain-sensitive" refers to a material that fractures or is otherwise impaired in response to a relatively low level of strain. In general, a layer having a high strain sensitivity, and consequently being prone to being the first layer to fracture, is located in the functional layer, such as a functional layer containing a relatively brittle semiconductor or other strain-sensitive device element. A neutral mechanical plane that is proximate to a layer need not be constrained within that layer, but may be positioned proximate or sufficiently near to provide a functional benefit of reducing the strain on the strain-sensitive device element when the device is conformed to a tissue surface. In some embodiments, proximate to refers to a position of a first element within 100 microns of a second element, or optionally within 10 microns for some embodiments, or optionally within 1 micron for some embodiments.

"Electronic device" generally refers to a device incorporating a plurality of components, and includes integrated circuits, large area electronics, printed wire boards, component arrays, biological and/or chemical sensors, physical sensors (e.g., temperature, strain, etc.), nanoelectromechanical systems, microelectromechanical systems, photovoltaic devices, communication systems, medical devices, piezo devices, optical devices and electro-optic devices. An electronic device may sense a property of the target tissue and/or may control a property of the target tissue.

"Sensing" and "sensor" refer to a functional electronic device or device component useful for detecting the presence, absence, amount, magnitude or intensity of a physical, biological state, and/or chemical property. Useful electronic device components for sensing include, but are not limited to, electrode elements, chemical or biological sensor elements, pH sensors, temperature sensors, strain sensors, mechanical sensors, position sensors, optical sensors and capacitive sensors. Useful functional electronic devices include various device components operably arranged to provide electrodes for detecting adjacent electric potential, sensors for detecting a biological condition (e.g., disease state, cell type, cell condition) or a chemical, pH, temperature, pressure, position, electromagnetic radiation (including over desired wavelengths such as associated with a fluorescent dye injected into tissue) or electric potential.

"Actuating" and "actuator" refer to a functional electronic device or device component useful for interacting with, stimulating, controlling, or otherwise affecting an external structure, material or fluid, for example a target tissue that is biological tissue. Useful actuating elements include, but are not limited to, electrode elements, electromagnetic radiation emitting elements, light emitting diodes, lasers, force generating elements, piezoelectric elements, acoustic elements, chemical elements and heating elements. Functional electronic devices include actuators that are electrodes for providing a voltage or current to a tissue, sources of electromagnetic radiation for providing electromagnetic radiation to a tissue, such as LEDs. Actuators also include ablation sources for ablating tissue, thermal sources for heating tissue, displacement sources for displacing or otherwise moving a tissue, fluid reservoirs, such as reservoirs of biologics or chemicals for releasing biologics or chemicals to affect biological function, such as a biological response including cell death, cell proliferation, or cell therapy by application of biologics or chemicals.

An "open mesh geometry" refers to a spatial arrangement of sensors and/or actuators in which the individual sensors and actuators are spaced from one another and distributed across an area of a flexible and stretchable substrate. An open mesh geometry is characterized by elements that occupy some, but not all, of an area of a substrate. In embodiments, the sensors and/or actuators in an open mesh geometry have a spatial density of between about 1 per $cm^2$ to 1 per $mm^2$.

"Mapping" refers to a process of spatially determining a physical, electrical, electromagnetic, chemical, biochemical and/or thermal property of an object or surface. In embodiments, a spatial map refers to a spatial distribution of contours or features of an object or surface. In embodiments, an optical map refers to a spatial distribution of an optical or electromagnetic property of an object or surface, such as absorbance, reflectance, emittance or transmittance. In embodiments, an electrical map refers to a spatial distribution of an electrical property of an object or surface, such as voltage, potential, resistance, capacitance, impedance, inductance, current or electric or magnetic field strength. In embodiments, a temperature map refers to a spatial distribution of temperature of an object or surface.

"Biocompatible" refers to a material that does not elicit an immunological rejection or detrimental effect, referred to herein as an adverse immune response, when it is disposed within an in-vivo biological environment. For example, in embodiments a biological marker indicative of an immune response changes less than 10%, or less than 20%, or less than 25%, or less than 40%, or less than 50% from a baseline value when a biocompatible material is implanted into a human or animal. Alternatively, immune response may be determined histologically, wherein localized immune response is assessed by visually assessing markers, including immune cells or markers that are involved in the immune response pathway, in and adjacent to the implanted device. In an aspect, a biocompatible device does not observably change immune response as determined histologically. In some embodiments, the invention provides biocompatible devices configured for long-term implantation, such as on the order of weeks to months, without invoking an adverse immune response. The implantation does contemplate some immune response as may occur for any minimally invasive procedures, such as needle insertion into tissue, so long as the immune response is locally confined, transient and does not lead to large-scale inflammation and attendant deleterious effects.

"Bioinert" refers to a material that does not elicit an immune response from a human or animal when it is disposed within an in-vivo biological environment. For example, a biological marker indicative of an immune response remains substantially constant (plus or minus 5% of a baseline value) when a bioinert material is implanted into a human or animal. In some embodiments, the invention provides bioinert devices.

The terms "directly and indirectly" describe the actions or physical positions of one component relative to another component. For example, a component that "directly" acts upon or touches another component does so without intervention from an intermediary. Contrarily, a component that "indirectly" acts upon or touches another component does so through an intermediary (e.g., a third component). In this manner, a delivery substrate may be described as indirectly supporting a device component through intermediate components corresponding to an adhesive layer and a substrate.

"Island" refers to a relatively rigid component of an electronic device comprising a plurality of semiconductor and/or metallic components. "Bridge" refers to structures interconnecting two or more islands or one island to another component. Specific bridge structures include stretchable semiconductor and metallic interconnects. In an embodiment, a device of the invention comprises one or more semiconductor-containing island structures, such as transistors, electrical circuits or integrated circuits, electrically connected via one or more bridge structures comprising electrical interconnects. The bridge structures may be bent, wavy (connected to wavy substrate), serpentine (in plane curvature) and/or in a pop-up (out of plane curvature) configuration, as described in various patent documents listed below in TABLE R1 (e.g., Ser. Nos. 11/851,182; 12/398,811, 12/405,475), which are specifically incorporated by reference herein. The invention includes tissue mounted devices and implantable devices comprising a flexible and stretchable device or device component that is provided in an island—bridge geometry, for example, comprising a plurality of ridged device islands corresponding to semiconductor devices or device components interconnected by bridge structures comprising stretchable interconnects. An interconnect that is "stretchable" or "flexible" is used herein to broadly refer to an interconnect capable of undergoing a variety of forces and strains such as stretching, bending and/or compression in one or more directions without adversely impacting electrical connection to, or electrical conduction from, a device component. Accordingly, a stretchable interconnect may be formed of a relatively brittle material, such as GaAs, yet remain capable of continued function even when exposed to a significant deformatory force (e.g., stretching, bending, compression) due to the interconnect's geometrical configuration. In an exemplary embodiment, a stretchable interconnect may undergo strain larger than 1%, optionally 10% or optionally 30% or optionally up to 100% without fracturing. In an example, the strain is generated by stretching an underlying elastomeric substrate to which at least a portion of the interconnect is bonded. For certain embodiments, flexible or stretchable interconnects include interconnects having wavy, meandering or serpentine shapes.

"Encapsulate" refers to the orientation of one structure such that it is at least partially, and in some cases completely, surrounded by one or more other structures, such as a substrate, adhesive layer or encapsulating layer. "Partially encapsulated" refers to the orientation of one structure such that it is partially surrounded by one or more other structures, for example, wherein 30%, or optionally 50% or optionally 90%, of the external surfaces of the structure is surrounded by one or more structures. "Completely encapsulated" refers to the orientation of one structure such that it is completely surrounded by one or more other structures. The invention includes devices having partially or completely encapsulated inorganic semiconductor components, metallic conductor components and/or dielectric components, for example, via incorporation a polymer encapsulant, such as biopolymer, silk, a silk composite, or an elastomer encapsulant.

"Enclosure" refers to a surface, object or device for at least partially surrounding or containing at least a portion of another surface, object or device or volume. In embodiments, a stretchable and flexible electronic device is provided as an enclosure which surrounds an enclosure volume. In embodiments, a biological tissue is provided inside a stretchable and flexible electronic device defining an enclosure and sensors and actuators of the stretchable and flexible electronic device are provided in conformal contact with the biological tissue.

"Barrier layer" refers to a component spatially separating two or more other components or spatially separating a component from a structure, material, fluid or environment external to the device. In one embodiment, a barrier layer encapsulates one or more components. In some embodiments, a barrier layer separates one or more components from an aqueous solution, a biological tissue or both. The invention includes devices having one or more barrier layers, for example, one or more barrier layers positioned at the interface of the device with an external environment.

"Nanostructured material" and "microstructured material" refer to materials having one or more nanometer-sized and micrometer-sized, respectively, physical dimensions (e.g., thickness) or features such as recessed or relief features, such as one or more nanometer-sized and micrometer-sized channels, voids, pores, pillars, etc. The relief features or recessed features of a nanostructured material have at least one physical dimension selected from the range of 1-1000 nm, while the relief features or recessed features of a microstructured material have at least one physical dimension selected from the range of 1-1000 µm. Nanostructured and microstructured materials include, for example, thin films (e.g., microfilms and nanofilms), porous materials, patterns of recessed features, patterns of relief features, materials having abrasive or rough surfaces, and the like. A nanofilm structure is also an example of a nanostructured material and a microfilm structure is an example of a microstructured material. In an embodiment, the invention provides devices comprising one or more nanostructured or microstructured inorganic semiconductor components, one or more nanostructured or microstructured metallic conductor components, one or more nanostructured or microstructured dielectric components, one or more nanostructured or microstructured encapsulating layers and/or one or more nanostructured or microstructured substrate layers.

A "nanomembrane" is a structure having a thickness selected from the range of 1-1000 nm or alternatively for some applications a thickness selected from the range of 1-100 nm, for example provided in the form of a ribbon, cylinder or platelet. In some embodiments, a nanoribbon is a semiconductor, dielectric or metallic conductor structure of an electronic device. In some embodiments, a nanoribbon has a thickness less than 1000 nm and optionally less than 100 nm. In some embodiments, a nanoribbon has a ratio of thickness to a lateral dimension (e.g., length or width) selected from the range of 0.1 to 0.0001. In some embodiments, a nanowire is a semiconductor, dielectric or metallic conductor structure of an electronic device. In some embodiments, a nanowire has a diameter less than 1000 nm and optionally less than 100 nm. In some embodiments, a nanowire has a ratio of thickness to width selected from the range of 0.1 to 10.

"Dielectric" refers to a non-conducting or insulating material. In an embodiment, an inorganic dielectric comprises a dielectric material substantially free of carbon. Specific examples of inorganic dielectric materials include, but are not limited to, silicon nitride and silicon dioxide. Dielectric materials further include silk, silk composites, elastomers and polymers.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomeric stamp" and "elastomeric transfer device" are used interchangeably and refer to an elastomeric material having a surface that can receive as well as transfer a material. Exemplary conformal transfer devices useful in some methods of the invention include elastomeric transfer devices such as elastomeric stamps, molds and masks. The transfer device affects and/or facilitates material transfer from a donor material to a receiver material. In an embodiment, a method of the invention uses a conformal transfer device, such as an elastomeric transfer device (e.g. elastomeric stamp) in a microtransfer printing process, for example, to transfer one or more single crystalline inorganic semiconductor structures, one or more dielectric structures and/or one or more metallic conductor structures from a fabrication substrate to a device substrate.

"Elastomer" refers to a polymeric material which can be stretched or deformed and returned to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers include, but are not limited to, thermoplastic elastomers, styrenic materials, olefinic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. In some embodiments, an elastomeric stamp comprises an elastomer. Exemplary elastomers include, but are not limited to silicon containing polymers such as polysiloxanes including poly(dimethyl siloxane) (i.e. PDMS and h-PDMS), poly(methyl siloxane), partially alkylated poly(methyl siloxane), poly(alkyl methyl siloxane) and poly(phenyl methyl siloxane), silicon modified elastomers, thermoplastic elastomers, styrenic materials, olefinic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a polymer is an elastomer.

"Conformable" refers to a device, material or substrate which has a bending stiffness that is sufficiently low to allow the device, material or substrate to adopt any desired contour profile, for example a contour profile allowing for conformal contact with a surface having a pattern of relief features. In certain embodiments, a desired contour profile is that of a tissue in a biological environment.

"Conformal contact" refers to contact established between a device and a receiving surface. In one aspect, conformal contact involves a macroscopic adaptation of one or more surfaces (e.g., contact surfaces) of a device to the overall shape of a surface. In another aspect, conformal contact involves a microscopic adaptation of one or more surfaces (e.g., contact surfaces) of a device to a surface resulting in an intimate contact substantially free of voids. In an embodiment, conformal contact involves adaptation of a contact surface(s) of the device to a receiving surface(s) such that intimate contact is achieved, for example, wherein less than 20% of the surface area of a contact surface of the device does not physically contact the receiving surface, or optionally less than 10% of a contact surface of the device does not physically contact the receiving surface, or optionally less than 5% of a contact surface of the device does not physically contact the receiving surface. In an embodiment, a method of the invention comprises establishing conformal contact between a conformal transfer device and one or more single crystalline inorganic semiconductor structures, one or more dielectric structures and/or one or more metallic conductor structures, for example, in a microtransfer printing process, such as dry transfer contact printing. In some embodiments, a force or pressure is provided between a device and a receiving surface, referred to herein as a "contact force" or a "contact pressure", that maintains contact between the device and the receiving surface. In some embodiments, a contact force is provided by gravity. In some embodiments, a contact force is provided by an elastic force generated within a stretchable and flexible substrate or layer that is in an expanded or stretched configuration where the elastic force is a restoring force tending to bring the stretchable and flexible substrate or layer to a non-expanded or -non stretched configuration.

"Young's modulus" also referred to as "modulus" is a mechanical property of a material, device or layer which refers to the ratio of stress to strain for a given substance. Young's modulus may be provided by the expression:

$$E = \frac{(\text{stress})}{(\text{strain})} = \left(\frac{L_0}{\Delta L}\right)\left(\frac{F}{A}\right), \tag{I}$$

where E is Young's modulus, $L_0$ is the equilibrium length, $\Delta L$ is the length change under the applied stress, F is the force applied, and A is the area over which the force is applied. Young's modulus may also be expressed in terms of Lame constants via the equation:

$$E = \frac{\mu(3\lambda + 2\mu)}{\lambda + \mu}, \tag{II}$$

where $\lambda$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably about 10 times larger for some applications, more preferably about 100 times larger for other applications, and even more preferably about 1000 times larger for yet other applications. In an embodiment, a low modulus layer has a Young's modulus less than 100 MPa, optionally less than 10 MPa, and optionally a Young's modulus selected from the range of 0.1 MPa to 50 MPa. In an embodiment, a high modulus layer has a Young's modulus greater than 100 MPa, optionally greater than 10 GPa, and optionally a Young's modulus selected from the range of 1 GPa to 100 GPa. In an embodiment, a device of the invention has one or more components, such as substrate, encapsulating layer, inorganic semiconductor structures, dielectric structures and/or metallic conductor structures, having a low Young's modulus. In an embodiment, a device of the invention has an overall low Young's modulus. In some embodiments, the flexible and stretchable substrate is a low modulus layer.

"Inhomogeneous Young's modulus" refers to a material having a Young's modulus that spatially varies (e.g., changes with surface location). A material having an inhomogeneous Young's modulus may optionally be described in terms of a "bulk" or "average" Young's modulus for the entire material.

"Low modulus" refers to materials having a Young's modulus less than or equal to 10 MPa, less than or equal to 5 MPa or less than or equal to 1 MPa. In an aspect, the functional layer has a low modulus and the delivery substrate has a higher Young's modulus, such as 10 times, 100 times, or 1000 times larger than the functional layer Young's modulus.

"Bending stiffness" is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

In the context of this description, a "bent configuration" refers to a structure having a curved conformation resulting from the application of a force. In an embodiment, the flexible and stretchable device or device components of the invention include one or more bent structures. Bent structures may have one or more folded regions, convex regions, concave regions, and any combinations thereof. Useful bent structures, for example, may be provided in a coiled conformation, a wrinkled conformation, a buckled conformation and/or a wavy (i.e., wave-shaped) configuration. Bent structures include structures having an overall spring geometry. Bent structures, such as stretchable bent interconnects, may be bonded to a flexible substrate, such as a polymer and/or elastic substrate, in a conformation wherein the bent structure is under strain. In some embodiments, the bent structure, such as a bent ribbon structure, is under a strain equal to or less than 30%, optionally a strain equal to or less than 10%, optionally a strain equal to or less than 5% and optionally a strain equal to or less than 1% in embodiments preferred for some applications. In some embodiments, the bent structure, such as a bent ribbon structure, is under a strain selected from the range of 0.5% to 30%, optionally a strain selected from the range of 0.5% to 10%, and optionally a strain selected from the range of 0.5% to 5%. Alternatively, the stretchable bent interconnects may be bonded to a substrate that is a substrate of a device component, including a substrate that is itself not flexible. The substrate itself may be planar, substantially planar, curved, have sharp edges, or any combination thereof. Stretchable bent interconnects are available for transferring to any one or more of these complex substrate surface shapes.

"Thermal contact" refers to the contact of two or more materials and/or structures that are capable of substantial heat transfer from the higher temperature material to the lower temperature material, such as by conduction. Thermal communication refers to a configuration of two or more components such that heat can be directly or indirectly transferred from one component to another. In some embodiments, components in thermal communication are in direct thermal communication wherein heat is directly transferred from one component to another. In some embodiments, components in thermal communication are in indirect thermal communication wherein heat is indirectly transferred from one component to another via one or more intermediate structures separating the components.

"Fluid communication" refers to the configuration of two or more components such that a fluid (e.g., a gas or a liquid) is capable of transport, flowing and/or diffusing from one component to another component. Elements may be in fluid communication via one or more additional elements such as tubes, containment structures, channels, valves, pumps or any combinations of these. In some embodiments, components in fluid communication are in direct fluid communication wherein fluid is capable of transport directly from one component to another. In some embodiments, components in fluid communication are in indirect fluid communication wherein fluid is capable of transport indirectly from one component to another via one or more intermediate structures separating the components.

"Electrical contact" or electrical communication refers to the ability of two or more materials and/or structures to transfer charge between them, such as in the form of the transfer of electrons or ions. Electrical communication refers to a configuration of two or more components such that an electronic signal or charge carrier can be directly or indirectly transferred from one component to another. As used herein, electrical communication includes one way and two way electrical communication. In some embodiments, components in electrical communication are in direct electrical communication wherein an electronic signal or charge carrier is directly transferred from one component to another. In some embodiments, components in electrical communication are in indirect electrical communication wherein an electronic signal or charge carrier is indirectly transferred from one component to another via one or more intermediate structures, such as circuit elements, separating the components.

"Optical communication" or optical contact refers to a configuration of two or more components such that electromagnetic radiation can be directly or indirectly transferred from one component to another. As used herein, optical communication includes one way and two way optical communication. In some embodiments, components in optical communication are in direct optical communication wherein electromagnetic radiation is directly transferred from one component to another. In some embodiments, components in optical communication are in indirect optical communication wherein electromagnetic radiation is indirectly transferred from one component to another via one or more intermediate structures, such as reflectors, lenses, or prisms, separating the components.

"Ultrathin" refers to devices of thin geometries that exhibit extreme levels of bendability. In an embodiment, ultrathin refers to circuits having a thickness less than 1 µm, less than 600 nm or less than 500 nm. In an embodiment, a multilayer device that is ultrathin has a thickness less than 200 µm, less than 50 µm, or less than 10 µm.

"Thin layer" refers to a material that at least partially covers an underlying substrate, wherein the thickness is less than or equal to 300 µm, less than or equal to 200 µm, or less than or equal to 50 µm. Alternatively, the layer is described in terms of a functional parameter, such as a thickness that is sufficient to isolate or substantially reduce the strain on the electronic device, and more particularly a functional layer in the electronic device that is sensitive to strain.

Figure 1D:
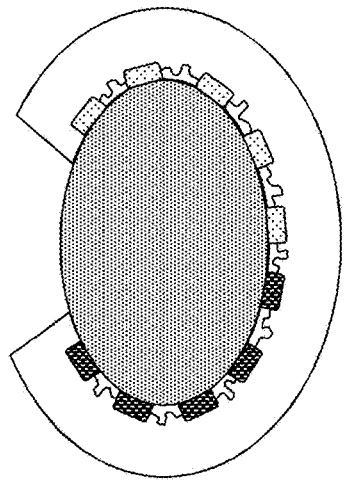
Figure 1C:
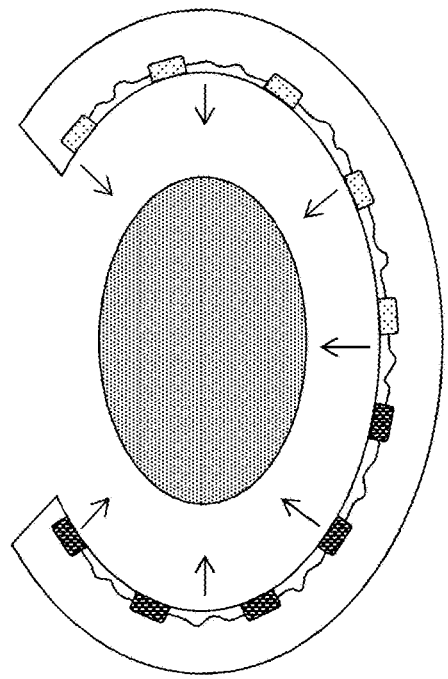

FIGS. 1A, 1B, 1C, 1D, 1E, 1F and 1G provide schematic illustrations of an overview of device and method embodiments of the invention for interfacing with a tissue, such as an internal biological tissue. As shown in FIG. 1A, a flexible and stretchable electronic device or device component 101 is provided. Here, device 101 comprises a plurality of sensors 102 and actuators 103 supported on an inner surface of a flexible and stretchable substrate 104. Device 101 is provided as an enclosure, defined by flexible and stretchable substrate 104. As illustrated schematically by the arrows in FIG. 1A, the enclosure is expanded to an expanded state 105, shown in FIG. 1B. Tissue 106 is then placed within the expanded enclosure 105, again schematically depicted by the arrow in FIG. 1B. In the expanded state 105, elastic forces, schematically depicted by the arrows in FIG. 1C, generated within device 101 tend to restore device 101 back to its original configuration and provide a contact force to conformally mount the sensors 102 and actuators 103 against the surface of tissue 106. FIG. 1D depicts device 101 enclosing approximately 80% of an outer surface of tissue 106, with sensors 102 and actuators 103 provided in conformal contact with tissue 106.

Figure 1E:
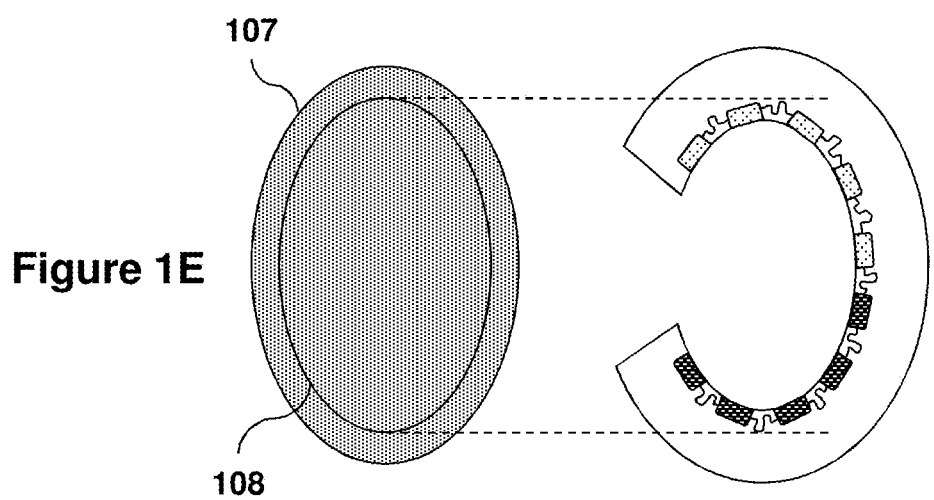
Figure 1F:
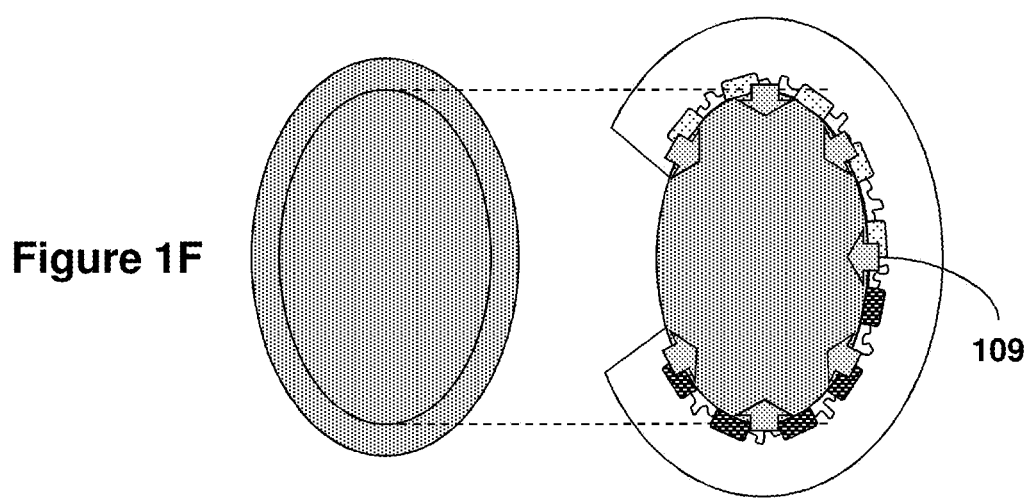
Figure 1G:
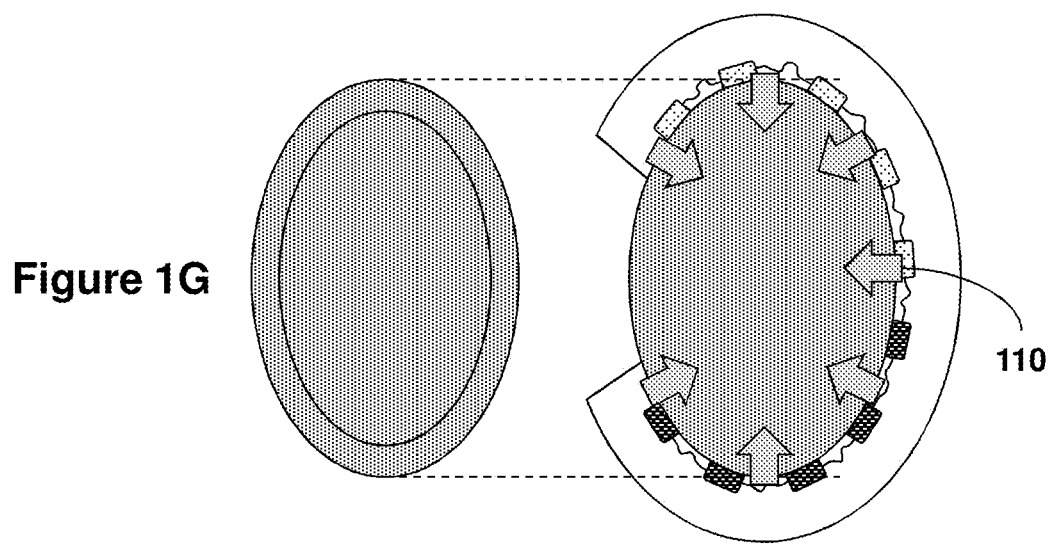

In embodiments, tissue 106 expands and contracts. FIG. 1E depicts a maximum size 107 of tissue 106 and a minimum size 108 of tissue 106 as compared to an unexpanded state of device 101, illustrating that even at its minimum size 108, tissue 106 is larger than the enclosure defined by the inner surface of the flexible and stretchable substrate 104 when device 101 is in an unexpanded state. FIG. 1F illustrates tissue placed within device 101 in an expanded state such that the inner surface of the flexible and stretchable substrate 104 makes conformal contact with tissue 106 at its minimum size 108. A first contact force, represented schematically by arrows 109 in FIG. 1F, is provided due to device 101 being provided in an expanded state and provides for maintaining conformal contact with tissue 106. As tissue 106 expands to its maximum size 107, device 101 is expanded to an even larger expanded state while the inner surface of the flexible and stretchable substrate 104 maintains conformal contact with tissue 106, as depicted in FIG. 1G. A second contact force, represented schematically by arrows 110 in FIG. 1F, is provided due to device 101 being provided in an expanded state and provides for maintaining conformal contact with tissue 106. In embodiments, tissue 106 repeatedly expands and contracts between its maximum size 107 and its minimum size 108 while conformal contact is maintained between tissue 106 and the inner surface of the flexible and stretchable substrate 104.

Figure 1H:
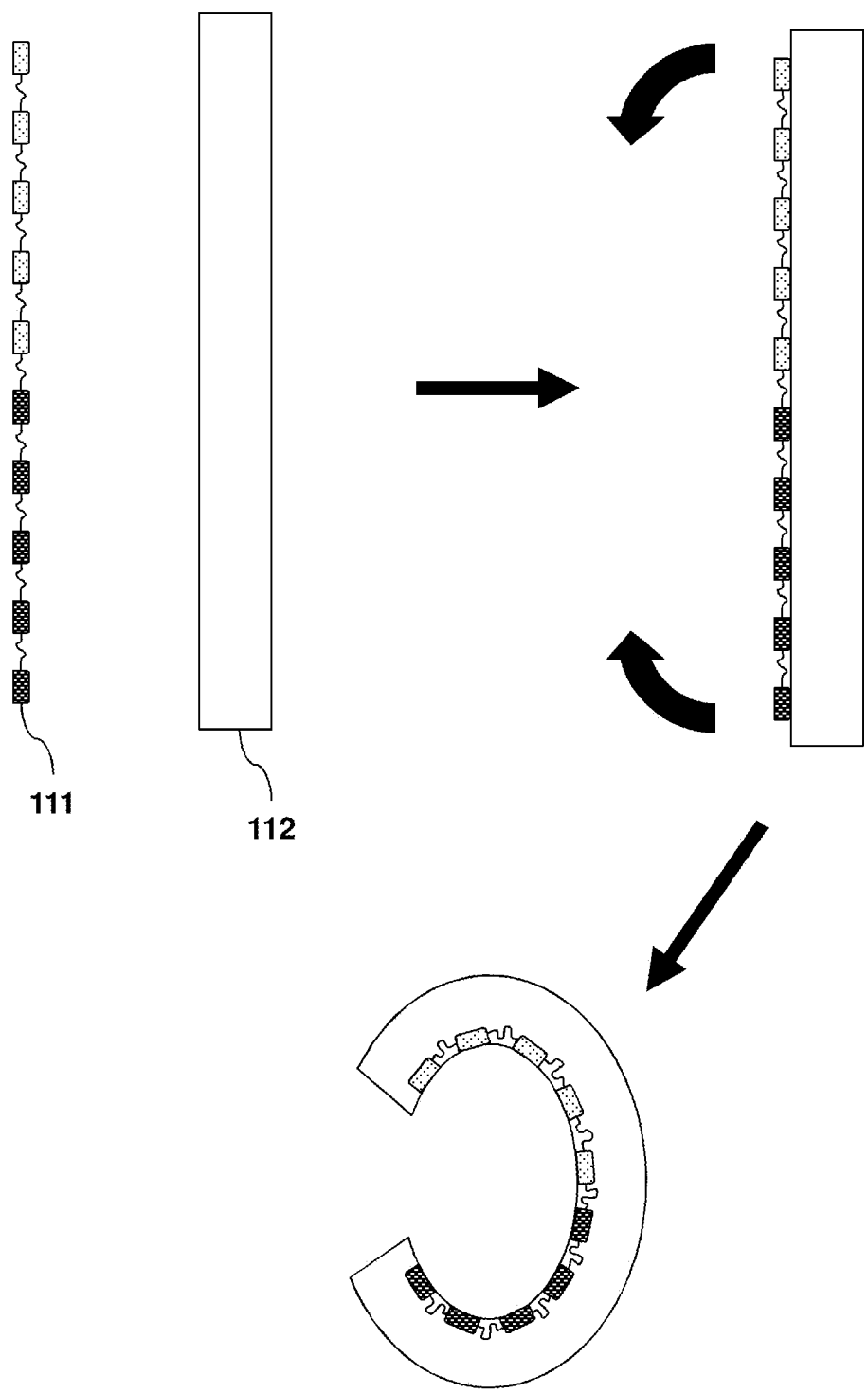
FIG. 1H and FIG. 1I provide schematic illustrations of method embodiments for making flexible and stretchable electronic devices.

FIG. 1H provides a schematic illustration of a method embodiment for making a flexible and stretchable electronic device or device component, such as a device for interfacing with, and optionally surrounding, an internal biological tissue. In this embodiment, a stretchable and flexible electronic device or device component 111 is transferred to stretchable and flexible substrate 112. Stretchable and flexible substrate 112 is then shaped, as schematically illustrated by the curved arrows, to match a three-dimensional surface shape of a target tissue.

Figure 1I:
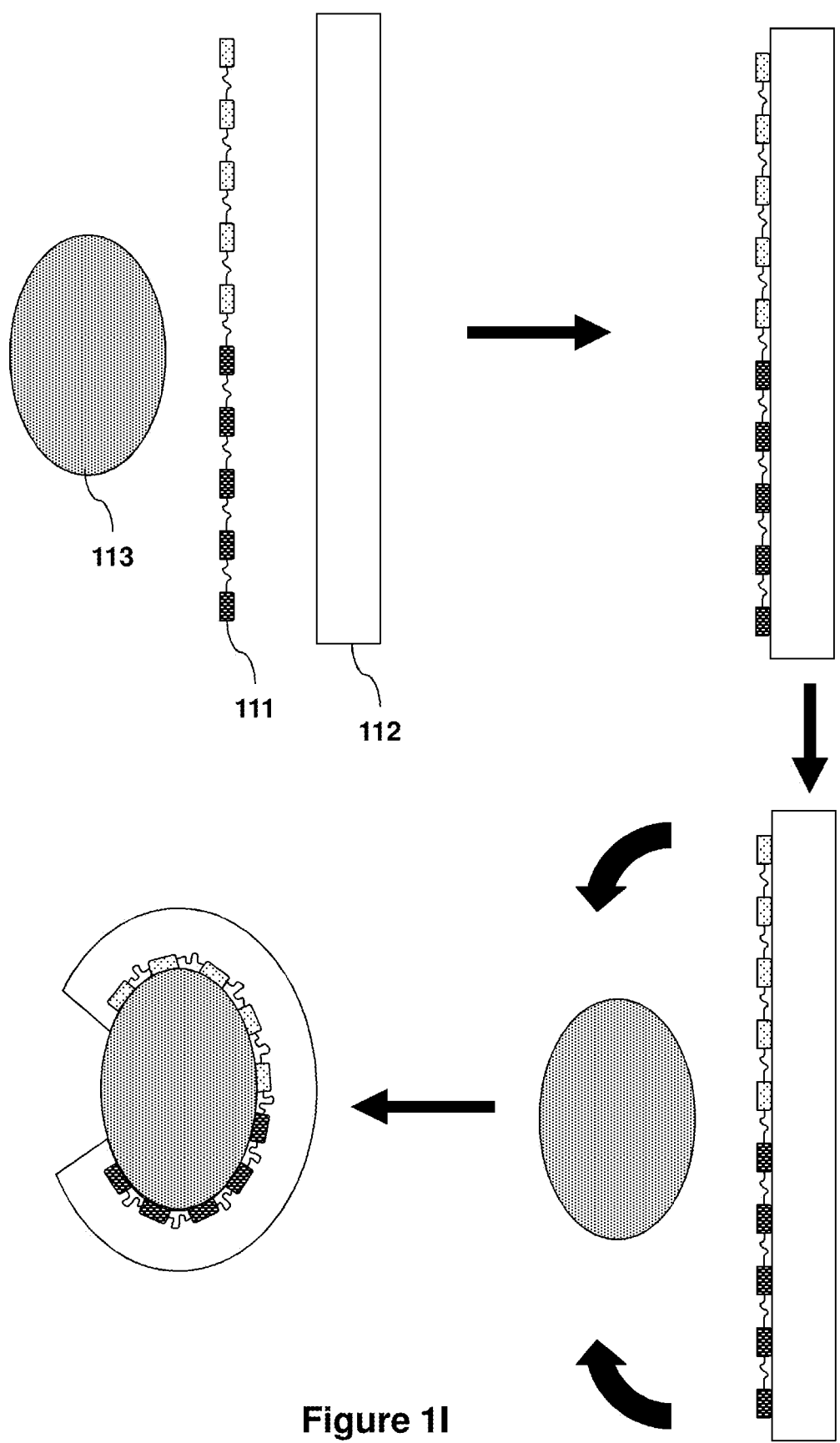

FIG. 1I provides a schematic illustration of another method embodiment for making a flexible and stretchable electronic device or device component, such as a device for surrounding and interfacing with an internal biological tissue. In this embodiment, a three-dimensional model 113 of the target tissue is provided. In some embodiments, three-dimensional model 113 represents an average size of the target tissue. In some embodiments, three-dimensional model 113 represents a minimum size of the target tissue. In some embodiments, three-dimensional model 113 represents the actual size of the target tissue. Optionally, the target tissue itself is provided in place of three-dimensional model 113. Three-dimensional model 113 also optionally represents a scaled-down version of the target tissue. Stretchable and flexible electronic device or device component 111 is transferred to stretchable and flexible substrate 112, and then stretchable and flexible substrate is shaped to three-dimensional model 113, as schematically illustrated by the curved arrows. For subsequent application to a target tissue itself, three-dimensional model 113 is removed from shaped stretchable and flexible substrate 112 and stretchable and flexible electronic device or device component 111.

Figure 1J:
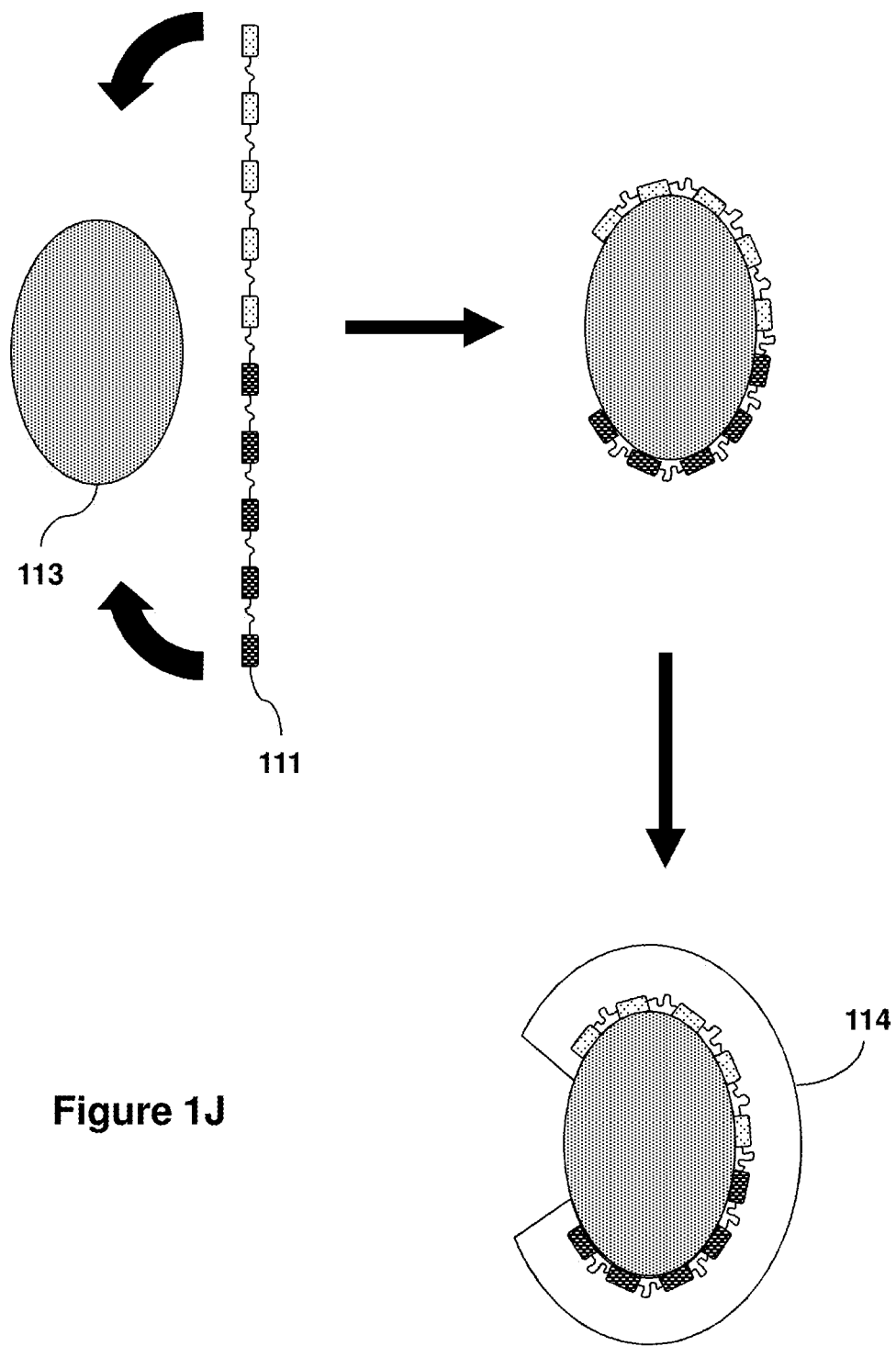
FIG. 1J provides a schematic illustration of another method embodiment for making a flexible and stretchable electronic device.

FIG. 1J provides a schematic illustration of another method embodiment for making a flexible and stretchable electronic device or device component, such as a device for surrounding and interfacing with an internal biological tissue. In this embodiment, a three-dimensional model 113 of the target tissue is provided. Optionally, the target tissue itself is provided in place of three-dimensional model 113. Flexible and stretchable electronic device or device component 111 is then applied to an outer surface of three-dimensional model 113. Next, a flexible and stretchable layer 114 is cast against the flexible and stretchable electronic device or device component applied to the outer surface of three-dimensional model 113. For subsequent application to a target tissue itself, three-dimensional model 113 is removed from cast stretchable and flexible layer 114 and stretchable and flexible electronic device or device component 111.

Figure 1K:
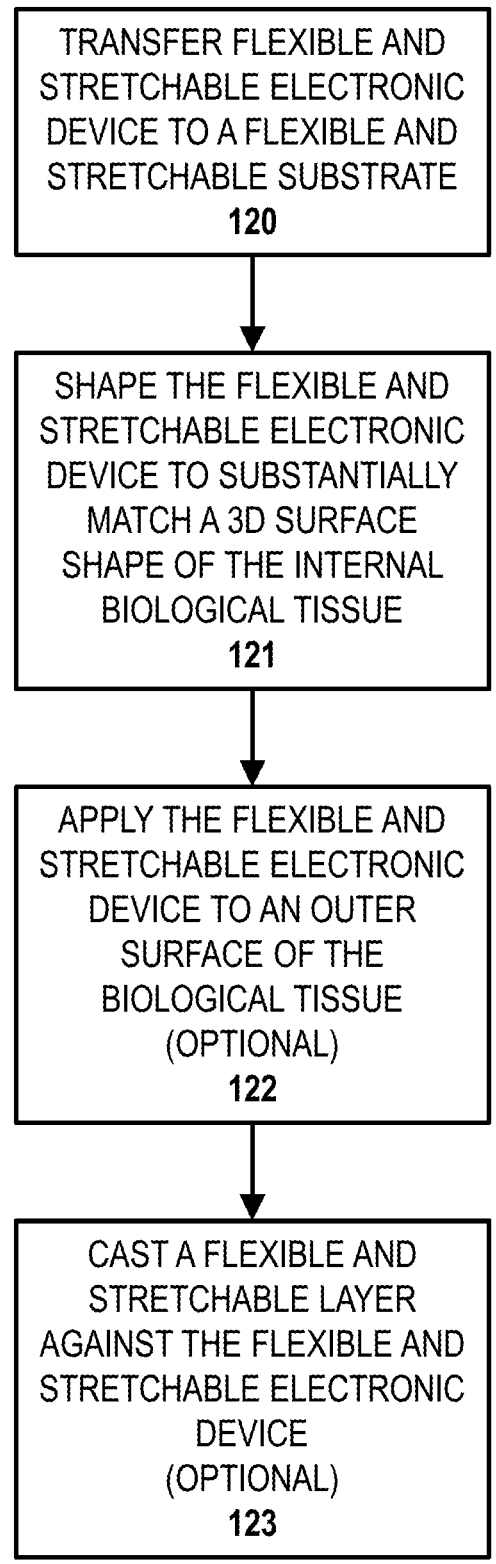
FIG. 1K provides an overview of an exemplary method embodiment for making a device for interfacing with an internal biological tissue.

FIG. 1K provides an overview of an exemplary method embodiment for making a device for surrounding and interfacing with an internal biological tissue. Initially, a flexible and stretchable electronic device or device component is transferred to a flexible and stretchable substrate (120), such as a flexible and stretchable electronic device or device component comprising one or more sensors, actuators or both. Next, the flexible and stretchable electronic device or device component is shaped to substantially match a three-dimensional surface shape of the internal biological tissue (121). Optionally, the flexible and stretchable electronic device or device component is applied to an outer surface of the biological tissue (122). Optionally, a flexible and stretchable layer is cast against the flexible and stretchable electronic device or device component applied to the outer surface of the biological tissue (123).

Figure 1L:
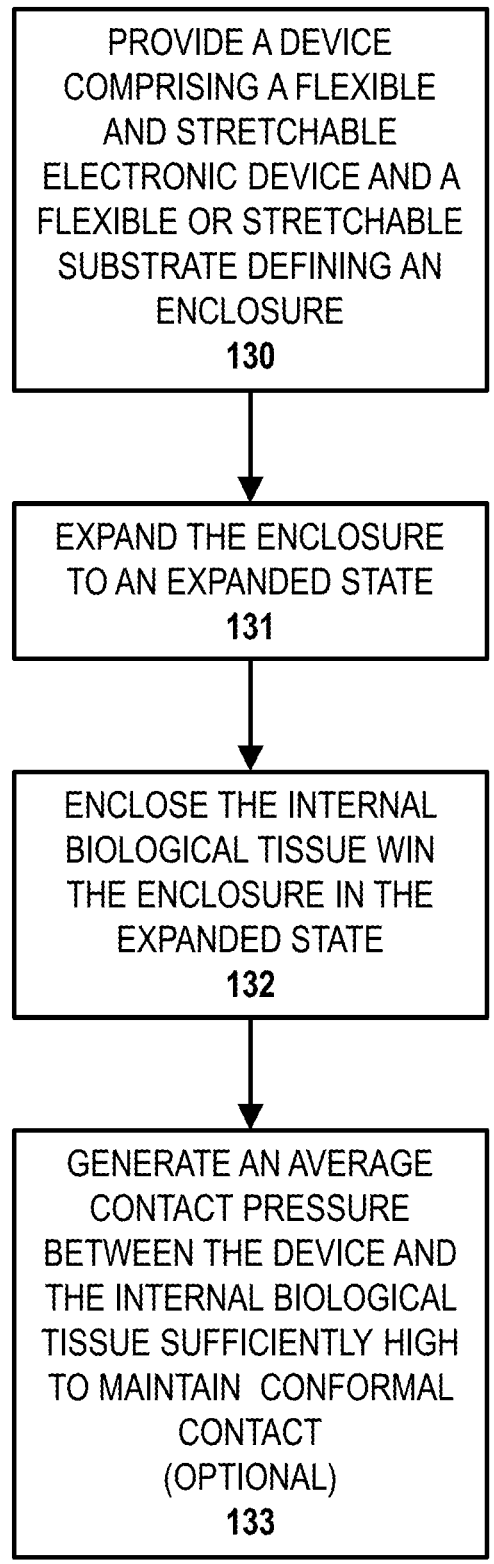
FIG. 1L provides an overview of an exemplary method embodiment for interfacing with an internal biological tissue.

FIG. 1L provides an overview of an exemplary method embodiment for interfacing with an internal biological tissue. Initially, a device comprising a flexible and stretchable electronic device or device component and a flexible or stretchable substrate defining an enclosure is provided (130), such as a flexible and stretchable electronic device or device component comprising one or more sensors, actuators or both supported by an inner surface of the flexible or stretchable substrate. Next, the enclosure is expanded to an expanded state (131). Next, the internal biological tissue is enclosed within the enclosure in the expanded state (132) such that an elastic contact force is generated to conformally mount and enclose the internal biological tissue to the device and interface with the internal biological tissue. Optionally, an average contact pressure between the device and the internal biological tissue is generated that is sufficiently high to maintain conformal contact (133)

The invention can be further understood by the following non-limiting examples.

Example 1: 3D Multifunctional Integumentary Membranes for Spatiotemporal Measurement/Stimulation Across the Entire Epicardium Means for high-density, large area, conformal multiparametric physiological mapping and stimulation are critically important in both basic and clinical cardiology. Recently developed conformal electronic systems enable important capabilities, but their embodiments as 2D sheets prevent integration over the full 3D epicardial surface and reliable contact for chronic use without sutures or adhesives. This example presents a qualitatively different approach that exploits 3D elastic membranes shaped precisely to match the epicardium of the heart via the techniques of 3D printing, as a platform for deformable arrays of multifunctional sensors, electronic and optoelectronic components. Such integumentary devices completely envelop the heart, in a form-fitting manner, as a sort of artificial pericardium. Inherent elasticity in the soft membranes provides a mechanically stable biotic/abiotic interface during normal cardiac cycles, even when completely immersed in fluids, without inducing adverse physiological responses. Component examples range from actuators for electrical, thermal and optical stimulation, to sensors for pH, temperature and mechanical strain. The semiconductor materials include silicon, gallium arsenide and gallium nitride, co-integrated with metals, metal oxides and polymers, to provide these and other operational capabilities. Ex vivo physiological experiments demonstrate various functions and methodological possibilities for cardiac research and therapy.

Tools for cardiac physiological mapping are indispensable for the clinical identification and understanding of mechanisms of excitation-contraction coupling, metabolic dysfunction, arrhythmia and others. Devices developed in the 1980s attempted to address this need by using synthetic fabrics sewn to loosely resemble the shape of the ventricle, with bulk electrodes manually assembled and woven into this platform. Although such schemes provide some utility, they do not enable uniform quality of contact across the heart, practical deployment in clinical settings, high-density mapping capabilities, provision for multifunctional, precision measurement/stimulation or deployment as chronic implants. As a result, alternative strategies based on serial mapping with point-contact catheters or on imaging techniques that use fluorescence, nuclear magnetic resonance or ultrasound have emerged, even though each has significant shortcomings.

The ideal scenario remains one in which device functionality integrates directly and non-invasively with the heart and is suitable for long-term use. The essential challenge is that the heart is a complex electromechanical syncytium with numerous elements working in synchrony to reliably pump blood and respond to changing metabolic demands. Although much has been gained from isolated cellular studies, the integral functional behavior on the organ level and the interaction between the electrical, metabolic and mechanical remodeling in disease states, especially in vivo, remain poorly explored due to paucity of adequate tools. Thus there is an unmet need for multiparametric mapping capabilities inclusive of but far beyond electrical sensing in a conformal, high-resolution manner, which cannot be realized using conventional materials, device technologies or imaging modalities.

Recent developments in materials and mechanics concepts for stretchable electronics create an opportunity to meet this challenge of direct, full 3D integration of devices with the epicardial surface. This example expands on previously reported small-scale electronic devices as 2D flexible sheets, to build multifunctional semiconductor systems in lithographically defined configurations on 3D, thin elastic membranes, custom-formed to match the shape of the heart. The physical format resembles that of the naturally occurring membrane that surrounds the heart, i.e. the pericardium. These systems, which are referred to herein as 3D multifunctional integumentary membranes (3D-MIMs) provide conformal interfaces to all points on the heart, with robust but non-invasive contacts enabled by the soft elasticity of the membrane itself, throughout dynamic cardiac cycles, even when completely immersed in fluid media. Measurements on isolated perfused rabbit hearts demonstrate the utility of these ideas as a general platform for multifunctional, high-density epicardial mapping/stimulation. The results provide advanced methodological possibilities for basic and clinical cardiology.

Figure 2A:
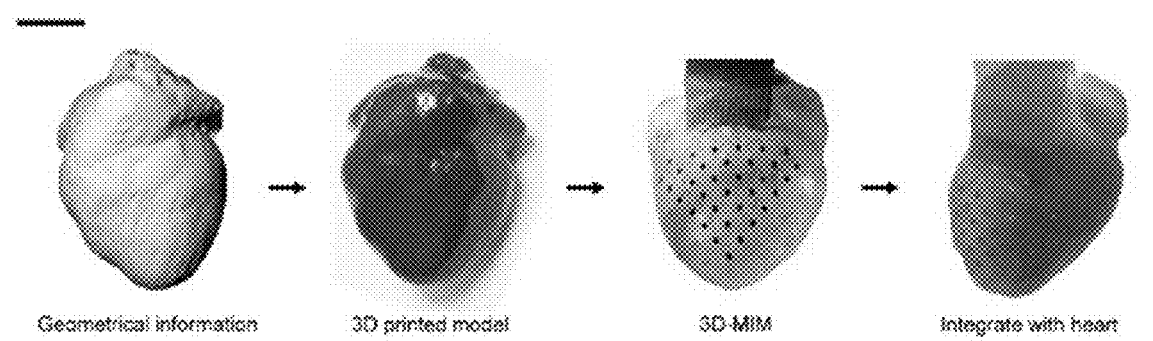
FIG. 2A, FIG. 2B and FIG. 2C provide an overview of 3D multifunctional integumentary membranes (3D-MIMs) for spatiotemporal measurement/stimulation across the entire epicardial surface.

The fabrication begins with the creation of a thin, 3D elastic membrane shaped to the heart. As shown in FIG. 2A, optical segmentation techniques first capture the full 3D geometry of a heart of interest. A commercial 3D printer (ZPrinter 450, Z-Corporation) then renders a solid model of the heart in a proportionally scaled form, as described later, to serve as a substrate for mounting ultrathin electronic/optoelectronic and sensor systems, separately prefabricated on planar substrates. Casting and curing a thin layer of silicone elastomer on top of the heart model with these multifunctional devices on its surface defines the overall format. The front faces of the device components contact the model while the back faces bond to the elastomer. Removing the system (i.e. 3D membrane with integrated device components) from the model prepares it for installation around a living heart, as a type of 'instrumented', artificial pericardium.

Figure 2B:
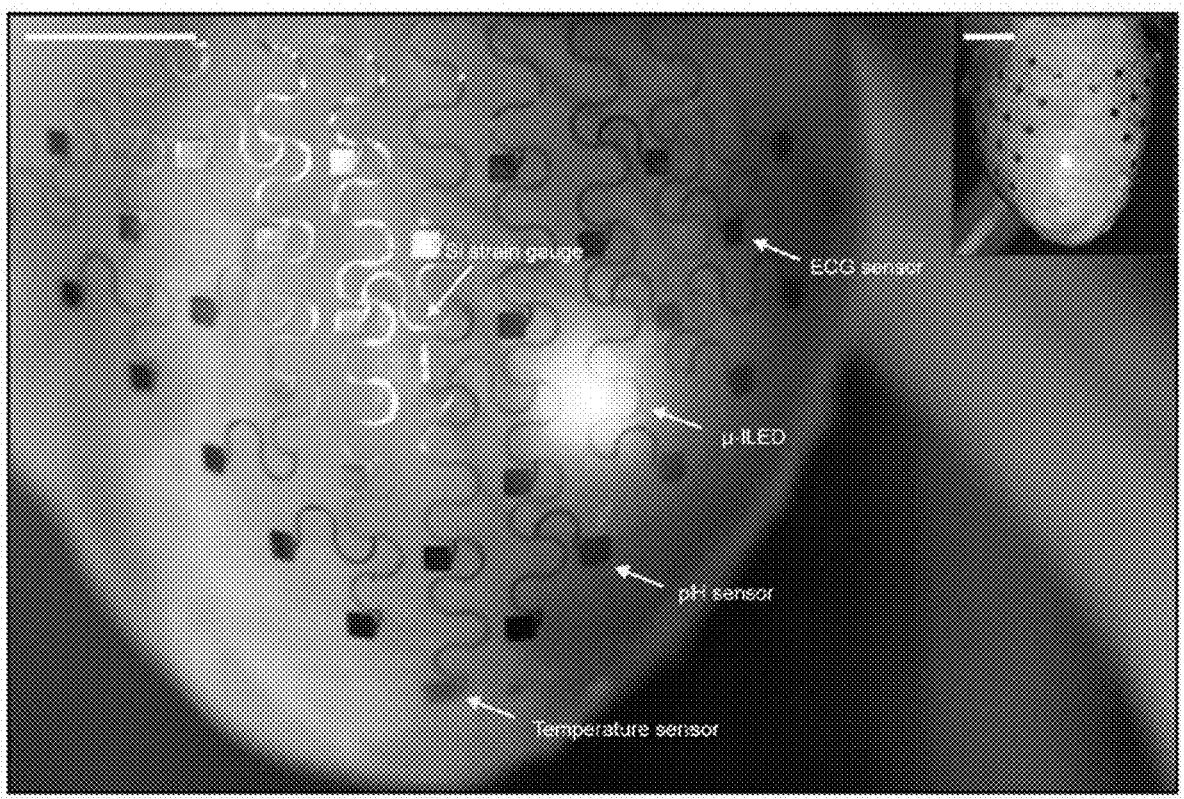

FIG. 2B shows a representative 3D-MIM that includes microscale, inorganic light emitting diodes (µ-ILEDs) based on indium gallium nitride (InGaN) for optical mapping, silicon (Si) nanomembranes for strain gauges, gold (Au) electrodes for electrical sensing/stimulation, iridium oxide (IrOx) pads for pH sensors and Au serpentine resistors for temperature sensors/heaters. The methods for creating these components exploit modern integrated circuit technologies and achieve spatial resolution far beyond that possible with manually assembled arrays. A thin, flexible heat-seal conductive cable (Elform, HST-9805-210) provides connection to external hardware for data acquisition, power supply and control. The 3D-MIM is engineered with overall dimensions slightly smaller than those of the real heart, to provide adequate elasticity and mechanical support for robust contact with the epicardium during diastole and systole, but with sufficiently small pressures to avoid disruption of natural behaviors of the cardiac tissue. The serpentine mesh that interconnects the device components covers the ventricle and conforms to the contours of the epicardium. Although this example is designed for research applications on rabbit hearts, the same strategies are applicable to human hearts, or even other organ systems. Here, the 3D geometries can be obtained using similar 3D printed substrates with patient specific MRI or CT organ segmentation.

Figure 3A:
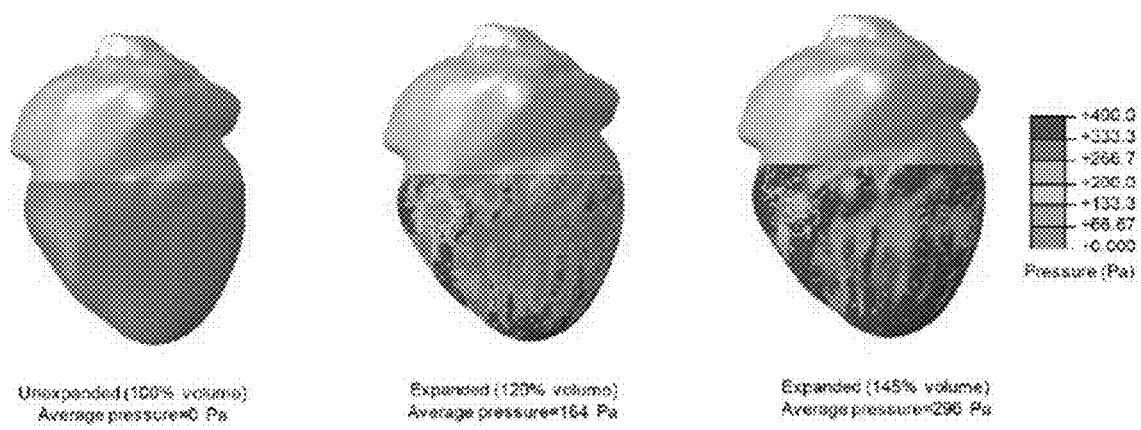
FIG. 3A and FIG. 3B provide an analysis of pressures on the epicardium associated with integration of a 3D-MIM.
Figure 3B:
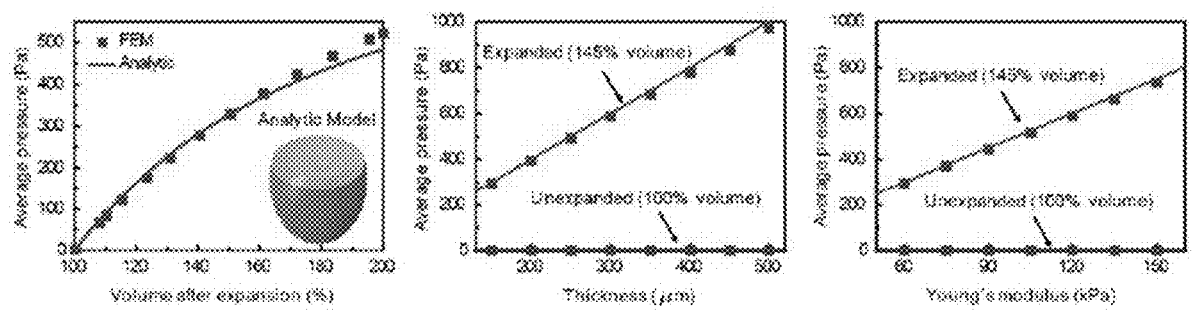

A useful and important feature of this type of device is that it can be designed to maintain a stable mechanical interface to the tissue while exerting minimal force on the contracting and relaxing heart muscle. In the cardiac anatomy of humans and other vertebrates, the myocardium is enclosed in a space sealed by the pericardium, which allows reversible volume change within a certain range. When a pathophysiological condition leads to inflammation, the pericardium exerts pressure to constrain the motions of the heart chambers. Quantitative analysis allows a comparative assessment of the pressure associated with our 3D device membrane on the epicardium, as well as the dependence of this pressure on materials properties and design parameters. FIG. 3A shows results for a 3D-MIM with a membrane thickness of 150 µm and effective Young's modulus of ~60 kPa (Ecoflex, Smooth-on) at various states of volume expansion $(1+\varepsilon)^3$ of a heart geometry, calculated using 3D finite element methods (FEM), where $\varepsilon$ is the linear expansion factor. The thickness of the membrane is uniform in the analysis; the nonuniformity due to the electronic devices results in local increase of the effective Young's modulus to ~80 kPa and adds <50% of the approximate pressure, as discussed below and in FIGS. 7A and 7B. The form of the undeformed membrane follows that of a 3D model, proportionally size-reduced (~30% volume reduction comparing to the diastolic state of the real heart) to ensure a baseline level of pressure upon application on the real heart. Computations correspond to the heart at its contracted volume (3D model), and at systolic (120% of the contracted volume) and diastolic (145% of the contracted volume) conditions. The calculated average pressures are similar to those of pericardium under normal physiological conditions, and only ~20% of these pressures under conditions of pericardial constraint. The results suggest that the device is unlikely to cause restrictive impact, as confirmed by ex vivo studies described subsequently. FEM and analytic modeling also establish general relationships between the pressure and the design parameters. FIG. 3B shows the average pressure as a function of the volume expansion, the thickness of the membrane and its Young's modulus. The analytic model uses a partial ellipsoid to approximate the geometry of the heart. Details appear below and in FIGS. 7A and 7B. The following expression connects the average pressure, the membrane geometry, mechanical properties and expansion factor:

$$P_{average} = C \times \frac{Et\varepsilon}{(1-v)(1+\varepsilon)^2}, \quad (1)$$

where t is the thickness of the membrane, E and v are the effective Young's modulus and the Poisson's ratio, respectively. The constant C decreases as the heart size increases, and C also depends on the shape of the heart (~0.2 mm$^{-1}$ for a rabbit heart). Decreases in membrane thicknesses and Young's moduli both linearly reduce the pressure. This scaling allows designs that provide pressures sufficiently large to maintain good contact between the sensor/actuator network and the epicardial surface, but sufficiently small to avoid impact on the intrinsic physiology. Monitoring the time course of several electrophysiological parameters that indicate ischemia in an isolated pressure loaded, working rabbit heart model with and without a 3D-MIM reveals the effects. The results, based on control (N=3) and experimental (N=3) hearts (FIGS. 8A and 8B), suggest that there is no additional ischemia caused by the devices, as measured by ST elevation and the amplitude of the LV pressure waveform.

Figure 4A:
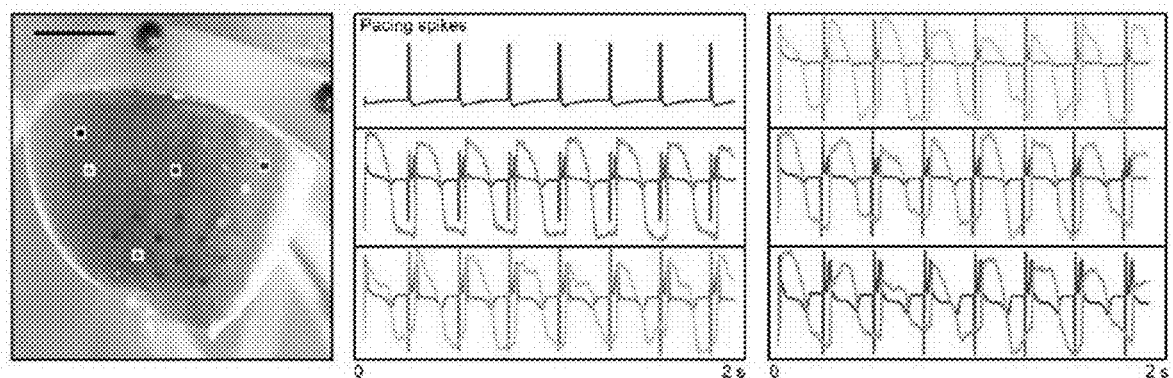
Figure 4D:
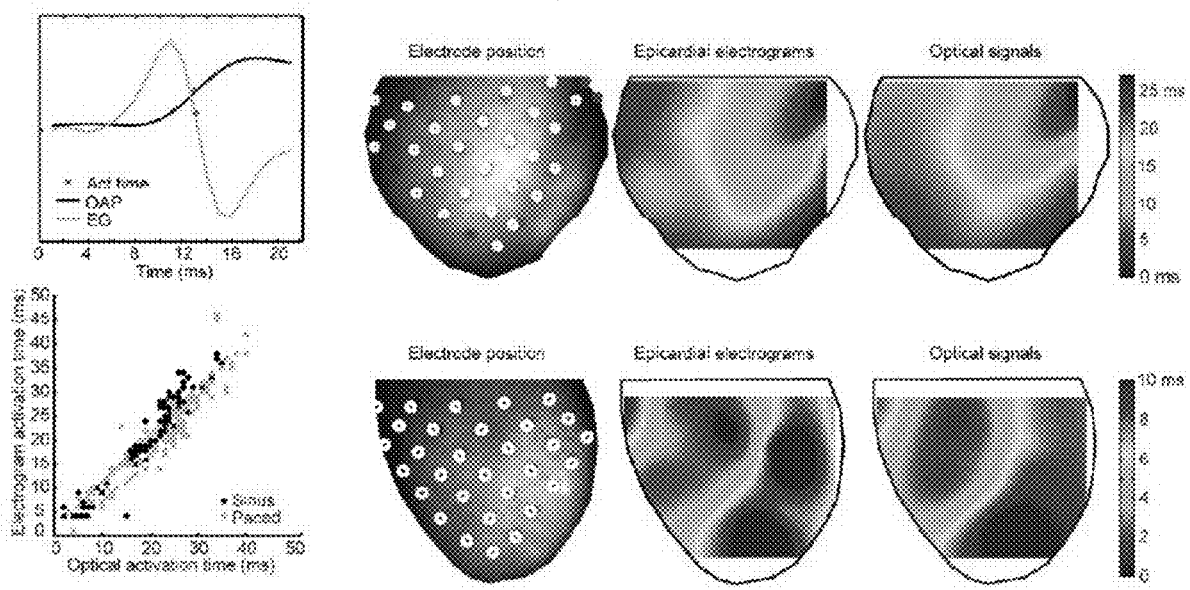
Figure 4D:
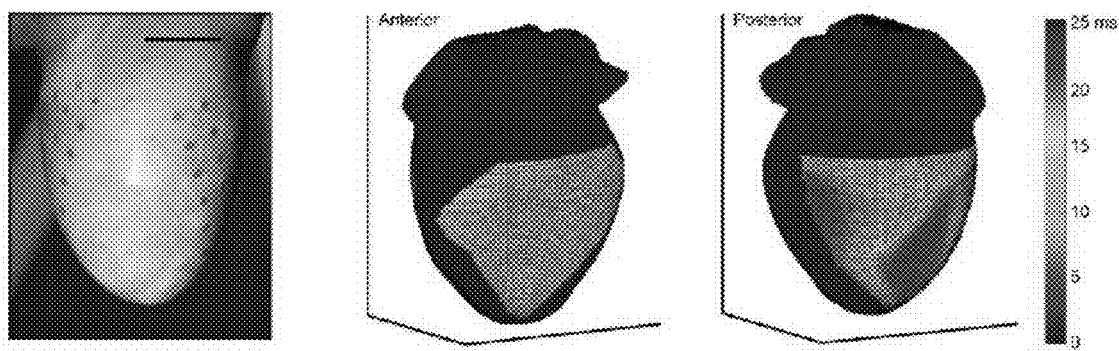
Figure 9:
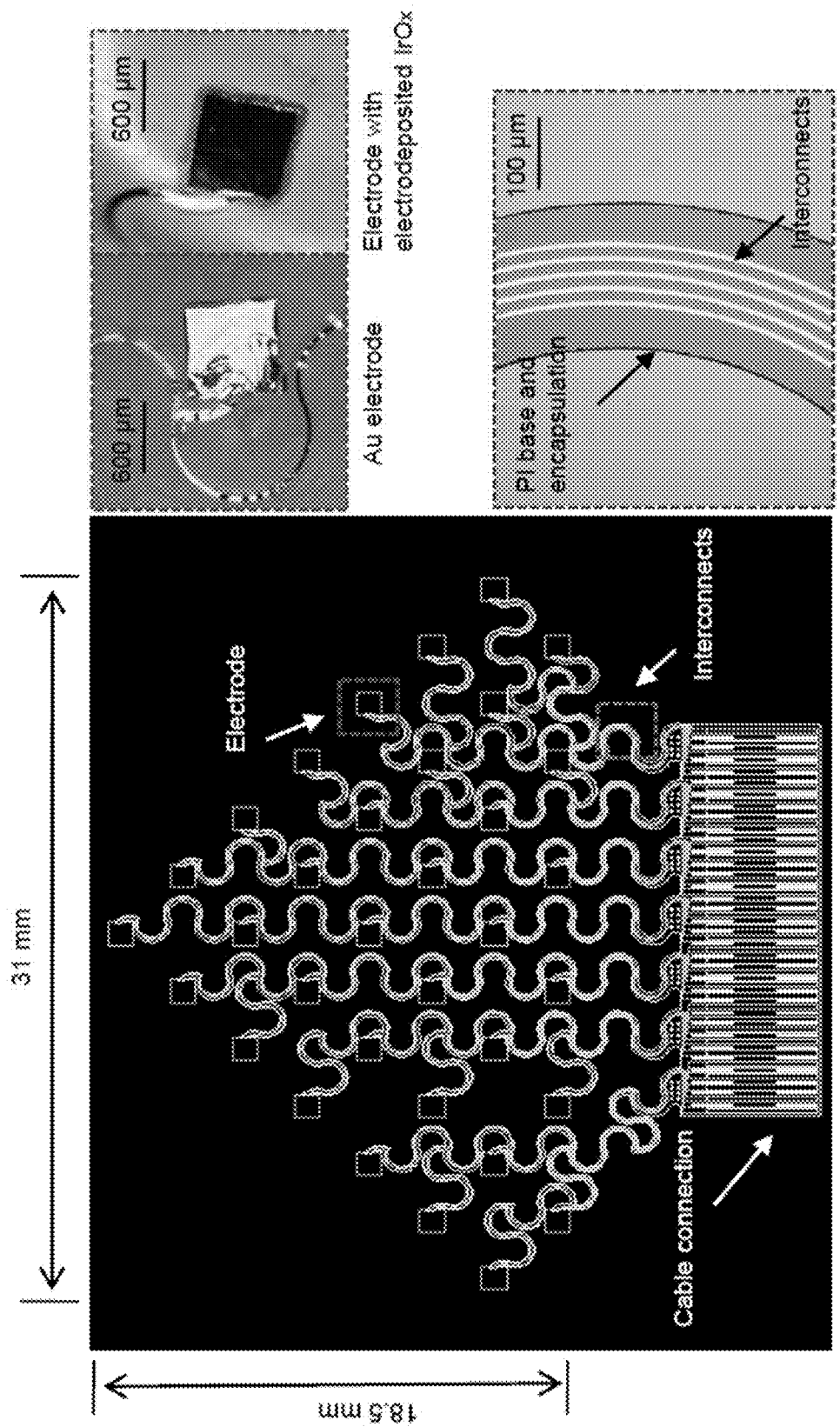
FIG. 9 provides an overview of the design of the electrode array for high precision ECG and pH mappings. The insets show magnified image of the gold electrode, electrode with electrodeposited $IrO_x$, and interconnects with PI base and encapsulation layers, respectively.
Figure 10:
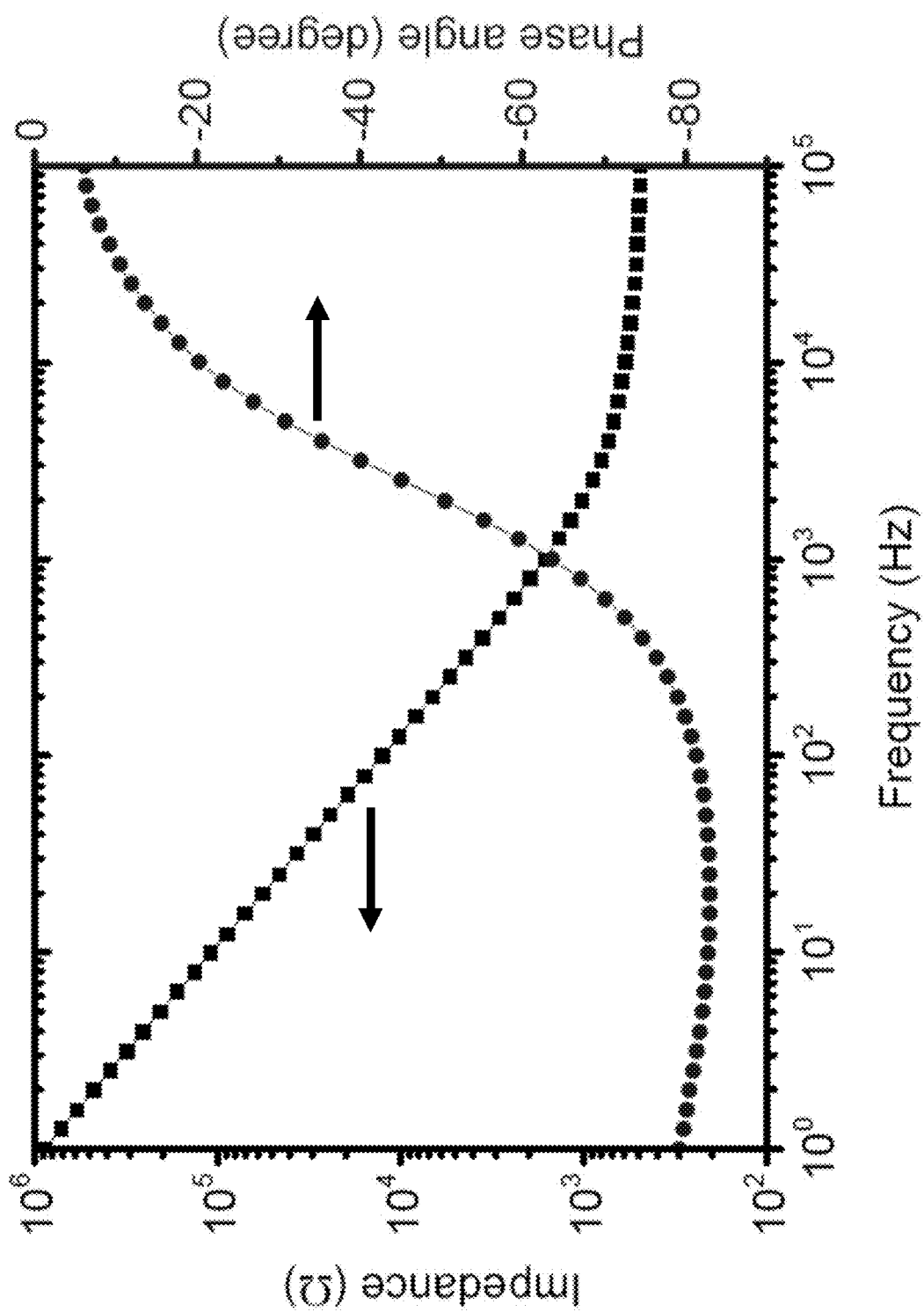
FIG. 10 provides electrochemical impedance spectroscopy (EIS) data of a representative 3D-MIM gold electrode measured in phosphate buffered saline.
Figure 11A:
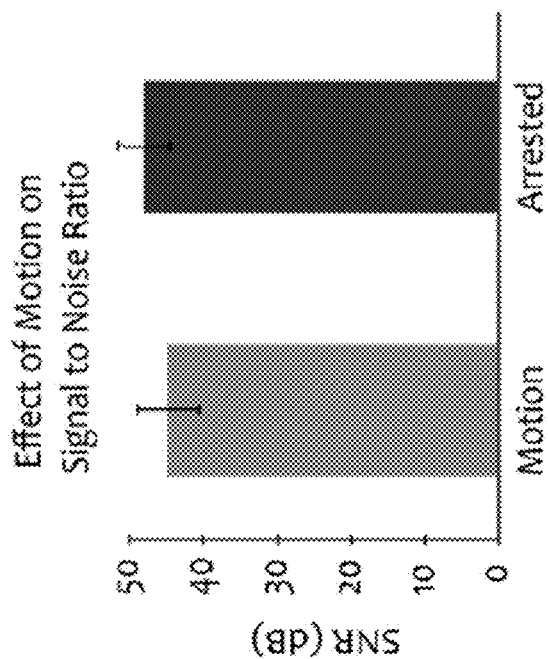
Figure 11A:
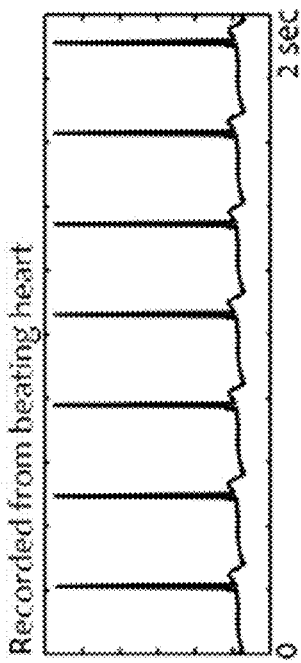
Figure 11A:
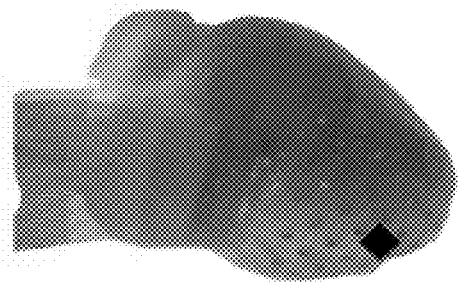
Figure 11B:
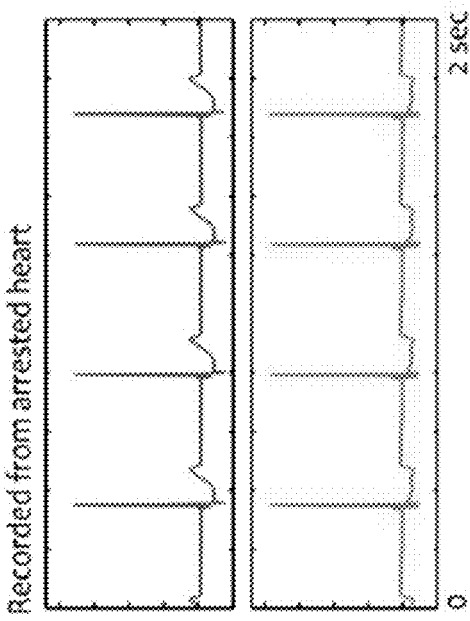
Figure 11B:
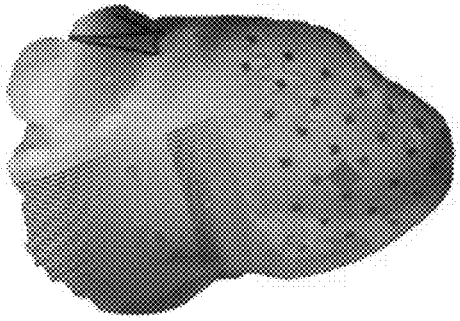

To demonstrate the various functional modes of operation we begin with high precision mapping of epicardial electrical activity. These experiments, and all of those that follow, used explanted Langendorff-perfused rabbit hearts. The device here incorporates 68 Au electrodes (1 mm$^2$ surface area and spacing of 3.5 mm), distributed across both the anterior and posterior surfaces of the epicardium (FIGS. 4A, 4D, and FIG. 9). The electrochemical impedances of individual electrodes are ~2 kΩ at frequency of 1 kHz, measured in phosphate buffered saline (FIG. 10). The transparency of the membrane allows simultaneous optical mapping through voltage dependent fluorescence, as a means for validating the electrical measurements. Experiments involved signals acquired from 4 hearts for a variety of conditions: normal sinus rhythms, and paced at a range of frequencies and from a range of electrode pairs to increase the variability of the propagation patterns in the spatial activation maps. The surface electrograms captured various key morphologies associated with the QRS and T waves (FIG. 4A). Representative maps and correlations between electrical and optical activation times appear in FIGS. 4C and 4B, respectively. The overall linear correlations between optical and electrical activation times were 0.957 for sinus data and 0.943 for paced data. These studies indicate that this configuration of measurement electrodes can replicate patterns of activation to a resolution that captures the spatial variations observed optically. Analyses for additional electrophysiological parameters are summarized in FIGS. 12A, 12B and 12C. FIG. 4D presents a 3D map derived from signals recorded from both anterior and posterior surface of the heart. Unlike optical mapping where motion artifacts dramatically impact the measurement quality and static heart geometries are required, electrophysiological mapping with 3D-MIMs can be applied under normal beating condition. It was observed that the integrated sensors move synchronously with the underlying cardiac tissue. Although it is practically difficult to avoid relative lateral motion between the sensors and the epicardium during beating cycles, due to the engineered geometries of 3D-MIMs, the displacement can be minimized to be less than the characteristic sizes of the sensors and to have negligible impact to the signal quality (FIGS. 11A, 11B and 11C). This feature is important for extending the mapping capabilities beyond laboratory studies and implementing in clinical electrophysiology.

Figure 5D:
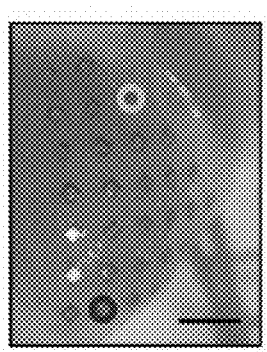
Figure 5D:
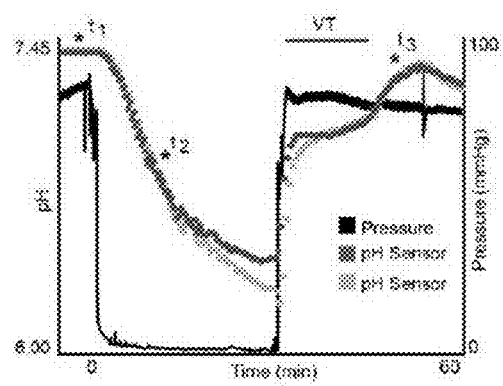
Figure 5D:
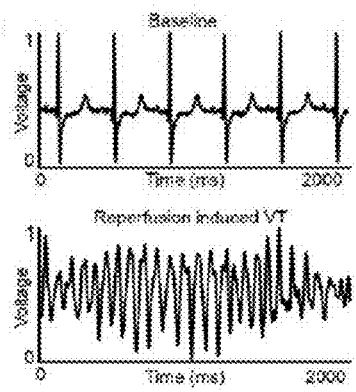
Figure 5D:
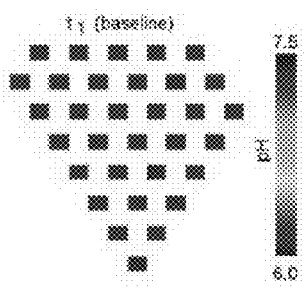
Figure 5D:
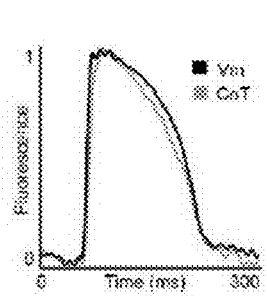
Figure 5D:
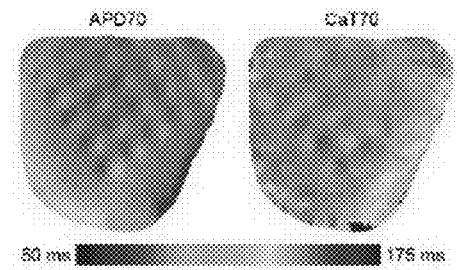
Figure 5E:
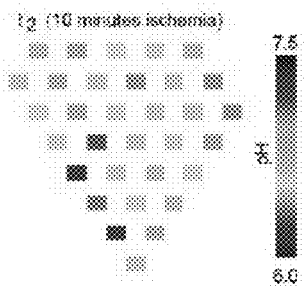
Figure 5E:
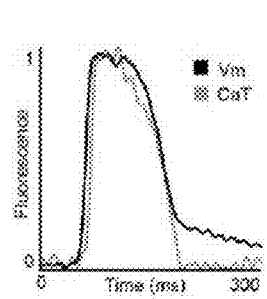
Figure 5E:
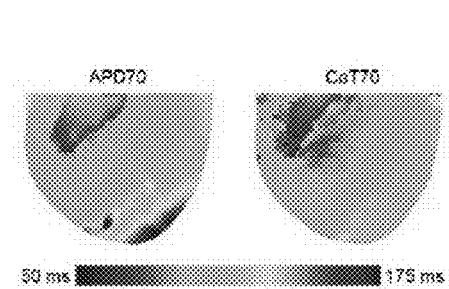
Figure 5F:
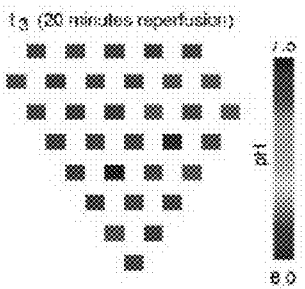
Figure 5F:
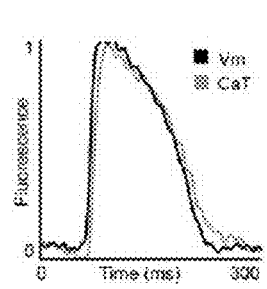
Figure 5F:
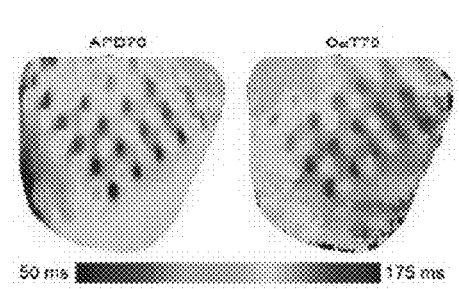
Figure 13:
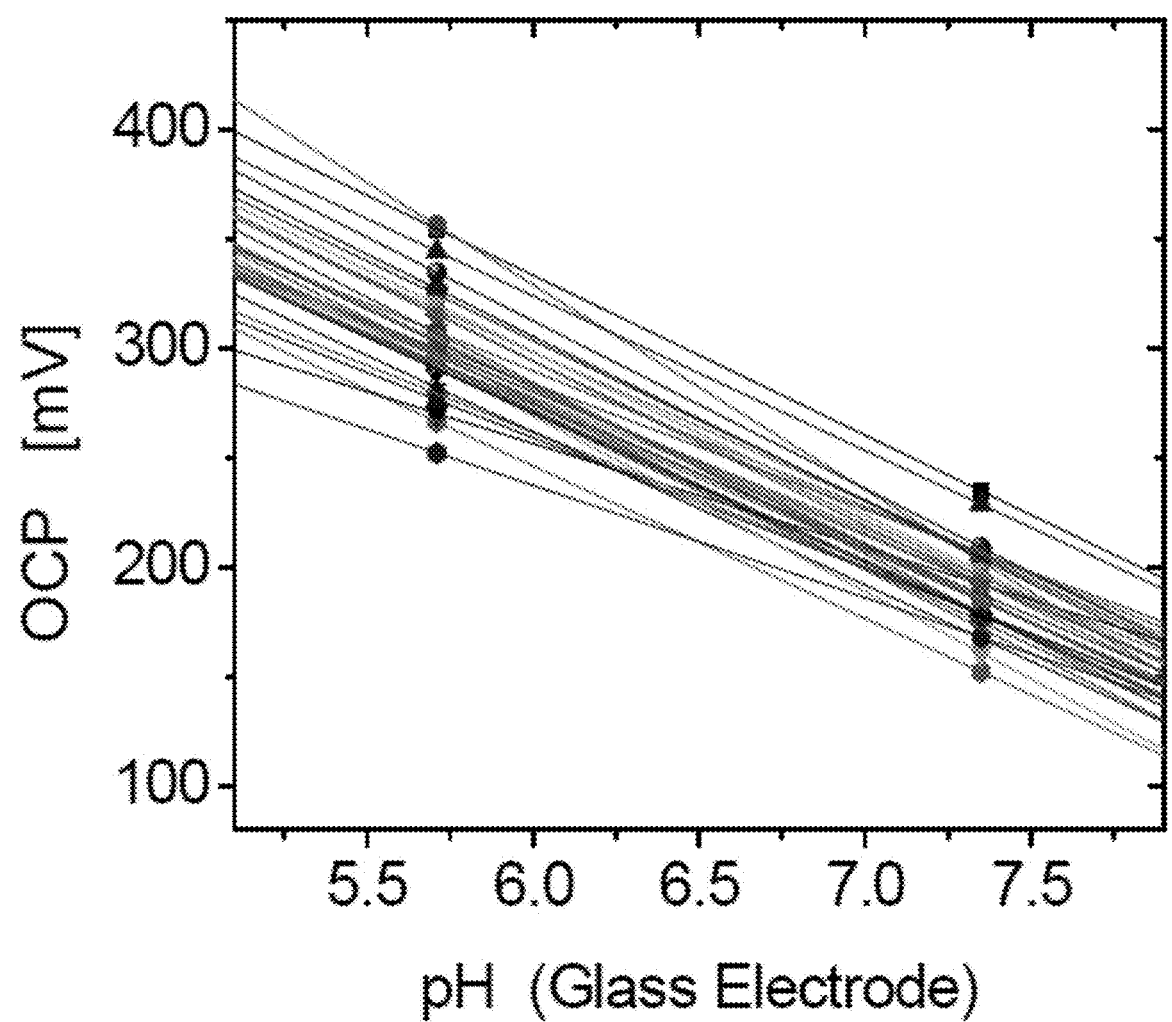
FIG. 13 provides data showing calibration of pH sensors.

Mapping of changes in pH provides useful information on the metabolic state of the heart. Here, iridium oxide (IrO$_x$), a well-established material for pH sensing, enables the measurement. Electrodeposited IrO$_x$ on Au electrodes provides pH sensors with open circuit potential (OCP) responses of 68.9±8.6 mV/pH at 37° C. in Tyrode's solution (FIG. 13). Such pH sensors, along with optical mapping techniques, enable acquisition of maps of pH, transmembrane potential (Vm), and calcium transient (CaT) signals during global no-flow ischemia-reperfusion. The pH sensors cover the left anterior and posterior surface of the rabbit heart (FIG. 5A). At baseline, all pH sensors record values between 7.34 and 7.40. The responses of two pH sensors (highlighted by grey and charcoal colors) are plotted (FIG. 5B) throughout the protocol. Complete spatial pH maps at time points $t_1$ (baseline), $t_2$ (10 minutes into ischemia), and $t_3$ (20 minutes into reperfusion) appear in FIGS. 5D-5E (left). Turning off the perfusion pump immediately reduced coronary pressure to 0 mm Hg and led to an approximately linear decrease in pH to minimum values of 6.40 (grey) and 6.22 (charcoal). Upon reperfusion, the pH rapidly increased until initiation of ventricular tachycardia (VT) where the pH stabilized at levels somewhat below baseline values. A sample far-field ECG of reperfusion-induced VT appears in FIG. 5C. After spontaneous conversion back to sinus rhythm, the pH values increased again to pre-ischemic values. FIGS. 5D-5F shows pH maps (left), representative optical signals (Vm—black and CaT—grey; middle) and side-by-side action potential duration at 70% repolarization (APD70) and calcium transient duration at 70% return to baseline (CaT70) maps. At the baseline, pH, APD70, and CaT70 maps highlight that the pH and electrophysiological parameters were initially uniform over the surface of the heart. After 10 minutes of ischemia, pH, APD70, CaT70 changed, though not in a spatially uniform manner. After 20 minutes of reperfusion, parameters returned to values close to the baseline levels. This experiment demonstrates possibilities in multiparametric mapping during ischemia/reperfusion. The information establishes anatomical relationships between metabolism and excitation-contraction coupling.

Figure 14:
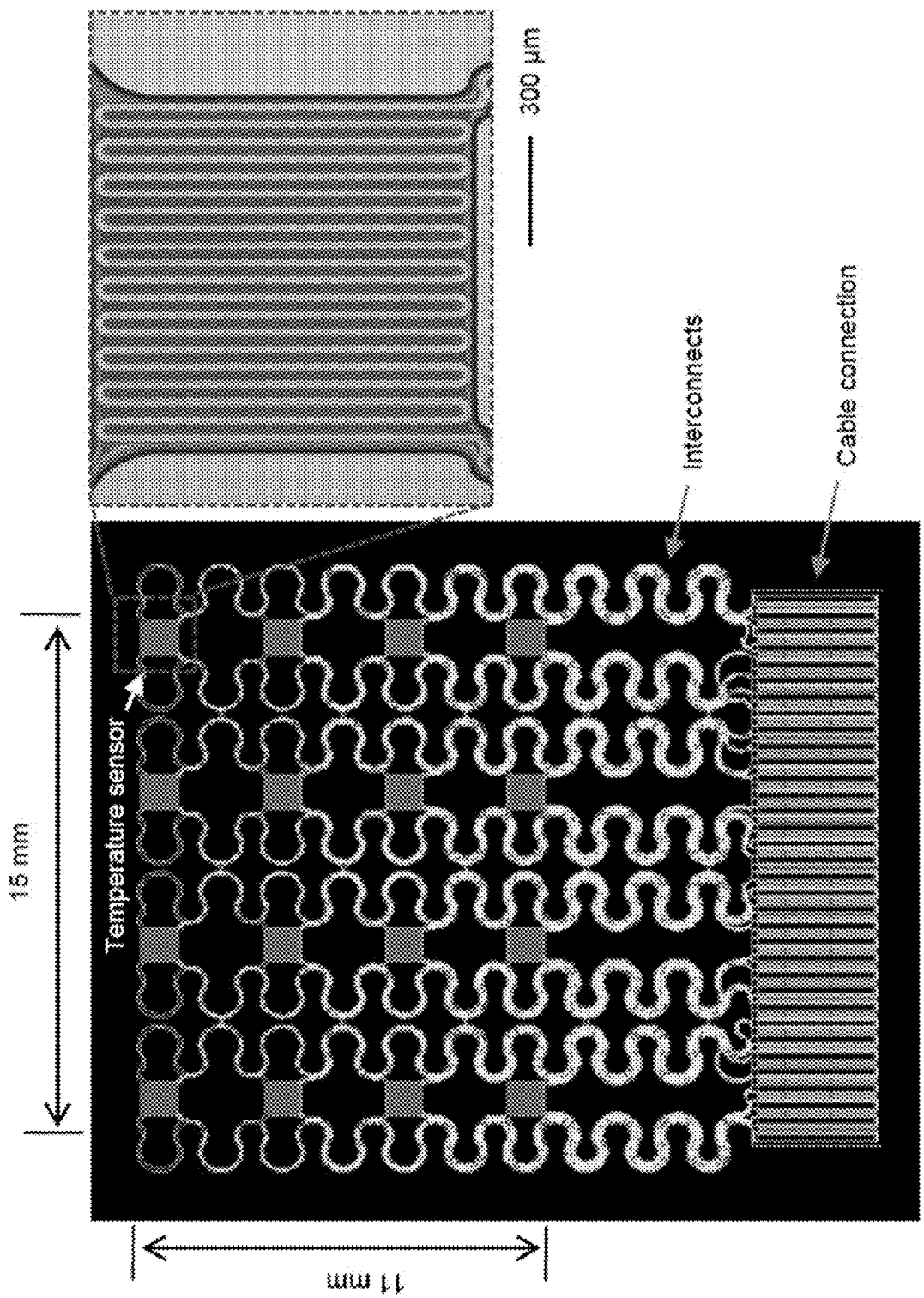
FIG. 14 provides an overview of the design of a temperature sensor array. The inset shows the magnified view of a gold serpentine trace for temperature sensing.
Figure 15:
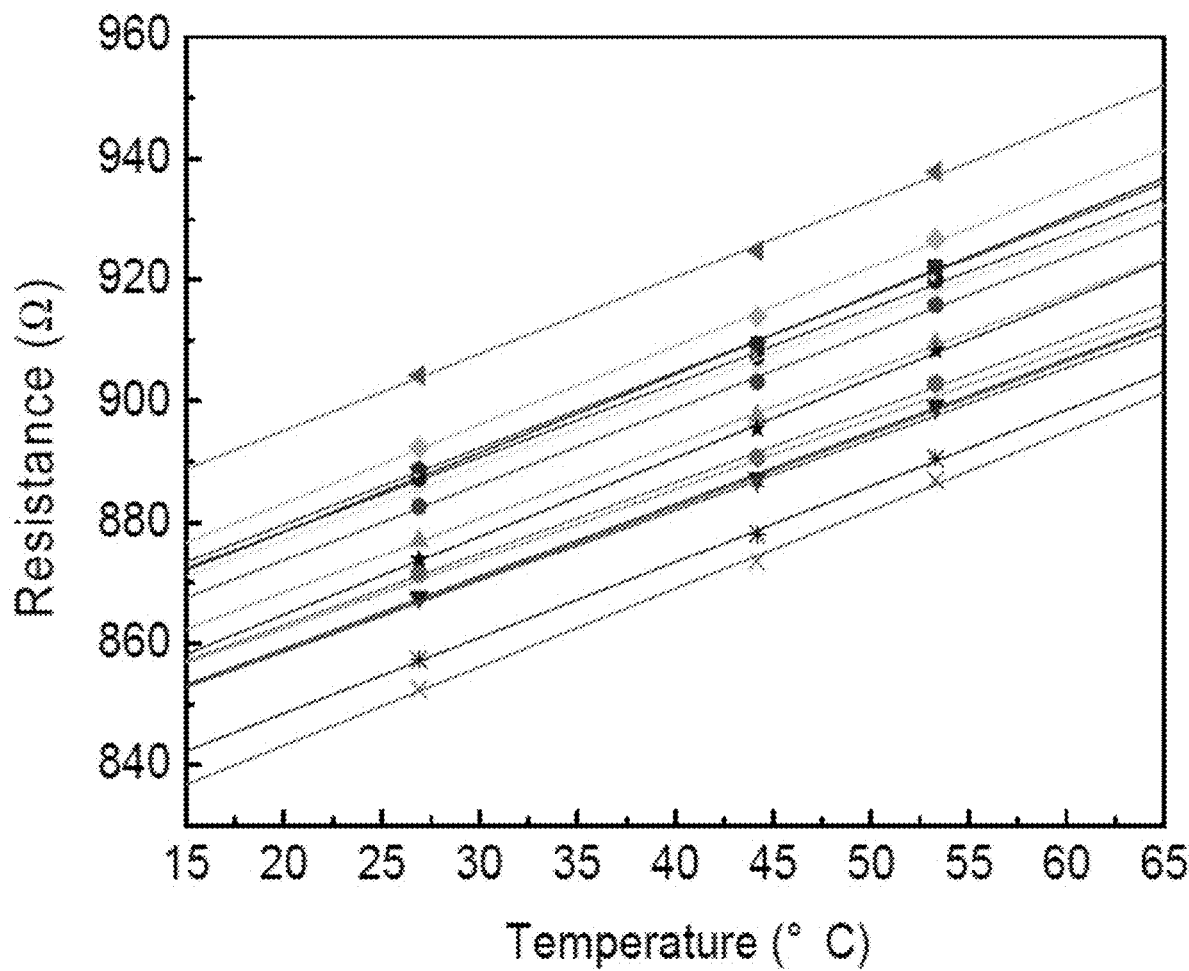
FIG. 15 provides data showing calibration of temperature sensors.

A 3D-MIM with arrays of temperature sensors illustrates capabilities in monitoring spatial distributions of cardiac temperature. The temperature sensor elements use designs established previously, consisting of serpentine traces of gold (20 μm wide, 50 nm thick) (FIG. 14) in which changes in resistance correlate to changes in temperature. The temperature sensors exhibit linear responses over physiological range, with a measurement precision of ~23 mK when sampled at 2 Hz in typical hospital settings. FIG. 6A shows a 3D-MIM with 16 integrated temperature sensors during use on a beating heart. The sensors are calibrated in temperature controlled water bath before the animal experiments, exhibiting responses of 1.23±0.05 Ω/° C. over 16 sensors across the array (FIG. 15). In one experiment, the temperature of the heart was changed by altering the temperature of the perfusion. As shown in FIG. 6A, the measured epicardial temperature gradually decreased by ~7° C. during cooling of the perfusate, with a uniform distribution of temperature across the heart. The heart rate, determined from the far-field electrogram, decreased with decreasing temperature and recovered to the original value as the temperature returned to physiological levels, indicating temperature controlled rate of myocardial metabolism. In a second experiment, a cautery pen was used to acutely burn a small region of the epicardium. The associated temperature map (FIG. 6B) shows localized elevation of temperature near the point of ablation. Such information can be used as feedback for clinical control of ablation time and size of affected area. In combination with electrical sensors, such device could provide real-time relation between temperature and excitation.

Figure 17:
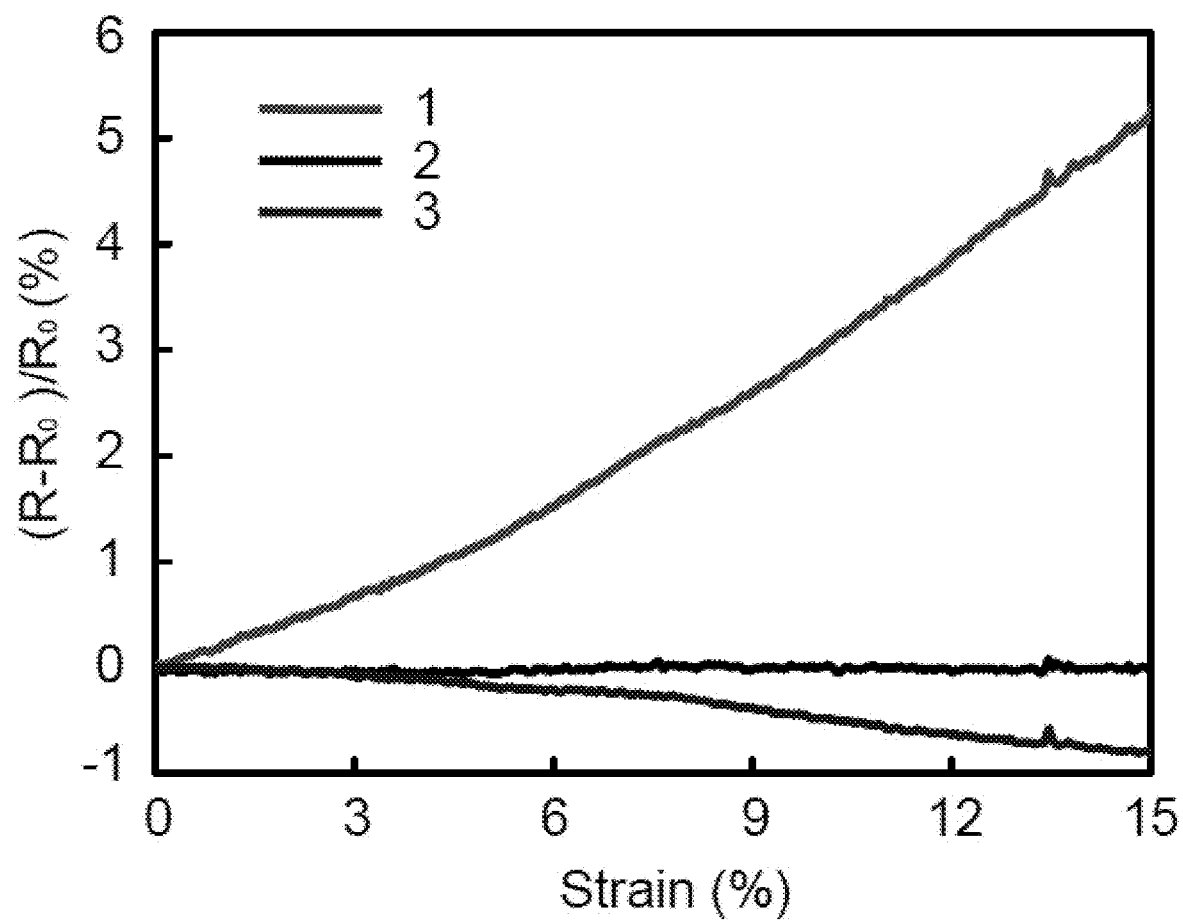
FIG. 17 provides data showing tensile test of Si strain sensors.

In addition to electrical and chemical evaluation, mechanical characteristics can be determined. Here, strain sensors based on piezoresistive effects in nanomembranes of Si allow monitoring of the mechanics of contractions of the heart during a variety of propagation states. Careful mechanical design of the serpentine interconnect structures allow accurate measurement in spite of the fact that typical epicardial strains greatly exceed the fracture threshold of Si, as described in previously reported small-scale 2D devices. In the present design, the 3D-MIM strain sensors include three p-doped Si piezoresistors in a rosette configuration (FIGS. 16A AND 16B). Two of the piezoresistors, with longitudinal axes perpendicular to each other, are aligned to the <110> crystalline directions of the Si, offering effective longitudinal gauge factor of ~0.33 and effective transverse gauge factor of ~−0.06 for each piezoresistor (FIG. 17). The other piezoresistor is aligned to the <100> crystalline direction and exhibit relatively small changes in resistance under strain, due to the intrinsic sensitivity associated with the crystalline direction as well as the overall device geometry. The piezoresistors aligned to the <110> directions provide maximum sensitivity for characterization of mechanical rhythms of the heart while the piezoresistor aligned to the <100> direction can be used to calibrate for effects of temperature. Experiments revealed the mechanical behaviors during sinus rhythm, ventricular pacing, and pharmacologically induced ventricular fibrillation (VF) with Pinacidil. Bath electrodes allowed simultaneously recording of far-field ECG to establish the temporal correlation between the electrical and mechanical behavior. FIG. 6C shows the response of a representative piezoresistor aligned to the <110> direction. The measurements reveal mechanical rhythms of the cardiac cycles, with a timing consistent with ECG recordings. Under VF condition, both the strain gauges and ECG show that the waveform lost normal rhythm and displayed random pattern typical for VF.

A final demonstration exploits arrays of μ-ILEDs, to illustrate the capacity for advanced semiconductor integration and optical mapping/stimulation. Here, nine ultrathin (3 μm), microscale (300×300 μm$^2$) light emitting diodes (LEDs) based on aluminum gallium indium phosphide (AlInGaP) with peak emission wavelengths of 670 nm (FIG. 18 and FIGS. 19A, 19B and 19C) served as local light sources for excitation of voltage sensitive dyes. Changes in fluorescence associated with these dyes allowed measurement of the cardiac action potential. FIG. 6D compares signals obtained with an external light source (Prizmatix, 630 nm) and with the integrated μ-ILEDs. In spite of their small sizes, the LEDs enable recording of clear action potentials, with waveform shapes consistent with external light. The results demonstrate the possibility of an in vivo optical mapping and/or stimulation system in a 3D integration format.

The results described in this example suggest routes for integrating active electronic materials and sensors in 3D, organ-specific designs, with potential utility in both biomedical research and clinical applications. With attention to materials, engineering mechanics and functional devices, these systems can establish conformal interfaces with the epicardium, and perform a variety of high density, large area physiological multiparametric mapping and stimulation. The devices can provide local information on the metabolic, excitable, ionic, contractile, and thermal state for investigations of both the spatial and temporal responses to a variety of insults, diseases, and therapies. The devices could be used to identify critical regions that indicate the origin of pathophysiological conditions such as arrhythmias, ischemia, hypoxia, ablation-induced trauma or heart failure. These regions could then be used to guide therapeutic interventions. These approaches present a promising opportunity to design and implement high definition implantable devices for diagnostics and therapy of lethal heart diseases.

Methods.

Figure 20:
FIG. 20 provides a photograph showing fixtures for maneuvering the 3D-MIM for Langendorff-perfused rabbit heart experiments.

Fabrication of 3D-MIMs:

The process, detailed below, starts with standard planar processing of inorganic semiconductor materials (Si, InGaN or AlInGaP) followed by transfer printing onto substrates coated either with a bilayer of polyimide (PI) on poly (methyl methacrylate) (PMMA) or poly(ethylene terephthalate) (PET) on poly(dimethylsiloxane) (PDMS). Dissolution of the PMMA or delamination from the PDMS allows release of the devices. Metal layers (Cr/Au) are vacuum deposited and patterned to form interconnects, resistors and electrodes. Application and patterning of a polymer encapsulation layer (PI or a photosensitive epoxy, SU8) on top of the devices completes their fabrication. Transfer printing delivers the resulting structures to a thin film of a low modulus silicone elastomer (Ecoflex, Smooth-on). A flexible conductive cable (Elform) bonded to contact pads at the periphery provides an interface to external hardware. A lamination process attaches the devices to a desired 3D printed model of the heart, with the sensors in direct contact with the surface. Casting and curing another layer of the same type of elastomer defines the overall 3D geometry of the system. In some cases, elastomer straps enhanced the maneuverability for use in Langendorff-perfused heart experiments (FIG. 20). Additional openings in the membrane can be included to prevent fluid build-up associated with flow in the supporting bath. Removal from the model allows electrodeposition of IrO$_x$ to yield pristine surfaces for precision pH sensing.

Figure 21:
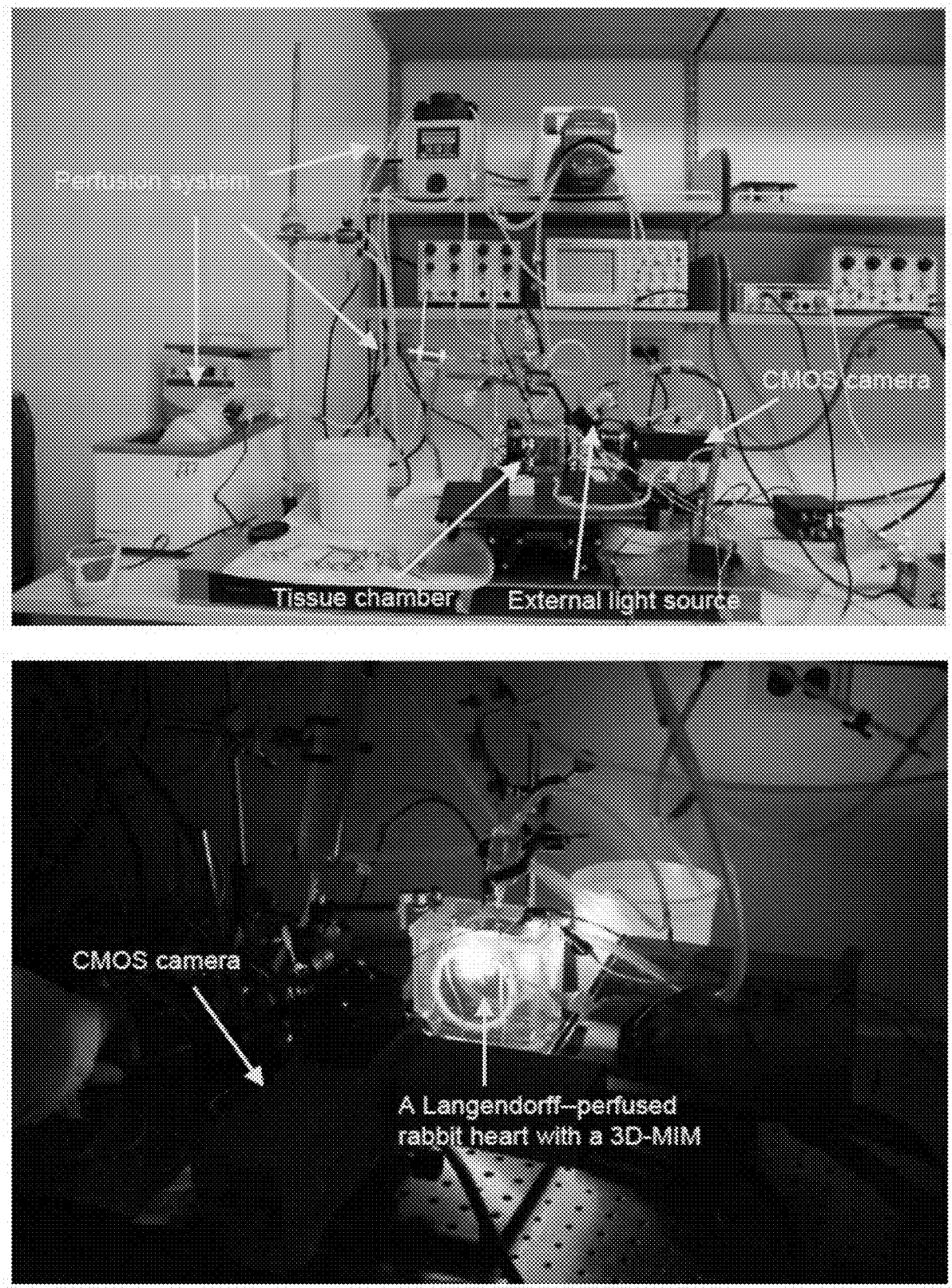
FIG. 21 provides photographs of the experimental setup for Langendorff-perfused rabbit heart experiments and optical mapping.

Animal Experiments:

Experiments were conducted in accordance with the ethical guidelines of the National Institutes of Health and with the approval of the Institutional Animal Care and Use Committee of Washington University in St Louis. The optical mapping procedure on Langendorff-perfused rabbit hearts was performed as previously reported in the literature. FIG. 21 illustrates representative experimental settings. Briefly the heart is removed via a thoracotomy and a cannula is placed in the aorta to allow retrograde perfusion of oxygenated Tyrode's solution. The perfusion mimics the electrolyte balance within the animal and provides an energy substrate for the heart to continue to function normally from an electrical perspective. The heart is submerged in a perfusion chamber maintained at 37° C. with a pH of 7.4±0.05. The optical signals of transmembrane potential (Vm) and calcium transients (CaT) rely on the collection of fluorescent signals from a potentiometric dye (di-4 ANEPPS or RH-237) or calcium indicator (Rhod-2a) added to the perfusate with a CMOS camera; when needed to avoid motion artifacts an excitation-contraction uncoupler (Blebbistatin) is also added to the perfusate.

Data Acquisition and Processing.

1. Electrophysiology: The electrical signals are recorded from the Au electrodes on the 3D-MIMs with a 240-channel unipolar electrogram acquisition system (Astrocard, Boston) and a custom-built interface. Both the optical and electrical signals are collected at a sampling frequency of 1 kHz, aligned with a trigger TTL pulse and post-processed separately in custom MATLAB software. Post-processing: The electrical signals acquired from the 3D-MIMs are first filtered with a 60 Hz notch filter internal to the acquisition software, then the electrophysiological parameter of interest activation time is calculated (FIG. 4C) and aligned to the spatial coordinates of the electrodes based on the optical background file. The optical signals are binned, filtered and normalized. The electrophysiological parameters are calculated for the complete field of view. To create the spatial maps, the activation times are interpolated using MATLAB's internal function for cubic interpolation of scattered data. The optical map is also sampled at the coordinates of the electrodes and the same interpolation method is applied to compare the full resolution optical pattern with the sampled optical map and the electrical map.

2. pH data is acquired using measurement of open circuit potential of each sensor referenced to an Ag/AgCl electrode.

3. Data for temperature and strain sensors is acquired with measurements of resistance of each sensor using a custom built system based on National Instruments PXI-6289 board.

Figure Descriptions.

Figure 2C:
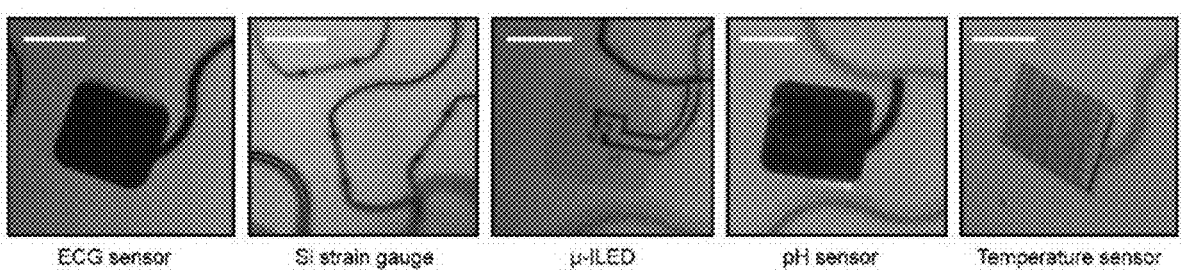

FIGS. 2A, 2B and 2C: 3D multifunctional integumentary membranes (3D-MIMs) for spatiotemporal measurement/stimulation across the entire epicardial surface. FIG. 2A: Graphical depiction of the key steps in device design and fabrication. Scale bar: 2 cm. FIG. 2B: Images of a representative 3D-MIM integrated on a Langendorff-perfused rabbit heart. The white arrows highlight various function elements in this system. The electronics can cover both anterior and posterior surfaces of the heart (inset). Scale bars: 6 mm. FIG. 2C: Magnified views of the functional elements in conformal contact with the epicardium. The images are recorded from the back side of the devices. Scale bars: 500 μm.

FIGS. 3A and 3B: Analysis of pressures on the epicardium associated with integration of a 3D-MIM. FIG. 3A: Calculated pressure distribution induced by a device with total thickness of 150 μm and effective Young's modulus of 60 kPa under various conditions of volume expansion of a heart's geometry. FIG. 3B: FEM and analytical results of average pressure as functions of volume expansion (left), thickness (middle) and Young's modulus (right) of the membrane.

FIGS. 4A, 4B, 4C and 4D: Demonstration of high-density electrical mapping. FIG. 4A: Representative optical and electrical signals acquired simultaneously from the corresponding colored electrode locations on a Langendorff-perfused rabbit heart. Scale bar: 7 mm. FIG. 4B: Top: schematic illustration of a representative optical action potential (OAP), unipolar electrogram (EG) and position of the activation time, defined as $$\frac{dV}{\partial t}\max$$

for the OAP and $$\frac{-dV}{\partial t}\max$$

for the EG. Bottom: correlation of electrical and optical activation times for hearts tested in a variety of states. FIG. 4C: Interpolated spatial activation maps determined from the electrical and optical measurements. Top: heart paced by the red pair of electrodes on the membrane. Bottom: sinus rhythm. FIG. 4D: 3D mapping of electrical signaling from both the anterior and posterior surfaces of the heart. Interpolated spatial maps of electrical activation time are projected on a representative rabbit heart geometry, for purposes of visualization. Scale bar: 7 mm.

FIGS. 5A, 5B, 5C, 5D, 5E and 5F: Demonstration of high-density pH mapping with simultaneous optical mapping of transmembrane potential and calcium transients. FIG. 5A: 3D-MIM with pH sensor array integrated on a Langendorff-perfused rabbit heart with 2 pH sensors highlighted and values displayed in FIG. 5B. Scale bar: 7 mm. FIG. 5B: Temporal change in pH during 30 minutes of no-flow ischemia followed by 30 minutes of reperfusion. Three times starred as $t_1$, $t_2$, and $t_3$ correspond to spatial pH maps in FIGS. 5D-5F. FIG. 5C: Representative far-field ECG during baseline and reperfusion induced VT. FIGS. 5D-5F: pH map of 32 sensors (left), representative transmembrane potential and calcium transient signals (middle), and APD70-CaT70 maps (right) at baseline (FIG. 5D), 10 minutes of no-flow ischemia (FIG. 5E), and 20 minutes of reperfusion (FIG. 5F). VT, ventricular tachycardia; Vm, transmembrane potential; CaT, calcium transient; APD70, action potential duration at 70% repolarization; CaT70, calcium transient duration at 70% relaxation.

FIGS. 6A, 6B, 6C and 6D: Demonstration of high-density temperature and strain sensing, and imaging using integrated μ-ILEDs. FIG. 6A: Application of a 3D-MIM for temperature monitoring during cold perfusion. Left: image of a 3D-MIM with 4×4 temperature sensor array integrated on a Langendorff-perfused rabbit heart. Middle: temperature recordings from a representative sensor illustrated in the left inset. Right: temperature maps at representative time points in the middle inset with corresponding heart rate calculated from ECG. Each pixel in the color map corresponds to recording from one temperature sensor. Scale bar: 1 cm. FIG. 6B: Temperature measurements during an ablation experiment. Positions of the sensor array and cautery pen are shown in the left inset. Temperature map during ablation (upper right) and recordings from representative sensors (bottom right) are shown respectively. Scale bar: 7 mm. FIG. 6C: Responses of a Si strain sensor under representative physiological conditions, compared with simultaneous ECG recordings. FIG. 6D: Left: image of a 3D-MIM with µ-ILEDs array in optical mapping experiments. Inset shows a magnified view of area around a representative µ-ILED. Right: comparison of optical signals from a representative pixel (blue dot on the left inset) recorded during excitation using µ-ILEDs on 3D-MIM and external optical excitation, respectively. Scale bar: 3 mm.

Mechanics Analysis of the 3D-MIM.

I. Numerical Analysis by 3D FEM.

The 3D FEM is used to study the pressure between the 3D multifunctional integumentary membrane (3D-MIM) and the heart for a wide range of device parameters and the expansion of the heart. The 3D geometric model of the heart is reconstructed by optical segmentations obtained from the medical scan. The geometric model is imported into the pre-processor in the ABAQUS finite element program. The heart and the 3D-MIM are modeled by the 4-node, linear tetrahedron solid element C3D4 and the 4-node quadrilateral membrane element M3D4 in ABAQUS, respectively. The total number of elements exceeds 60,000, and mesh refinement ensures the accuracy of the numerical results. For the prescribed expansion of the heart, FEM gives the pressure distribution at the interface between the 3D-MIM and the heart. The average pressure is then obtained over the contact area between the 3D-MIM and the heart, i.e. the ventricles of the heart as in the experiment, as shown in FIG. 3A.

II. The Pressure.

Figure 7A:
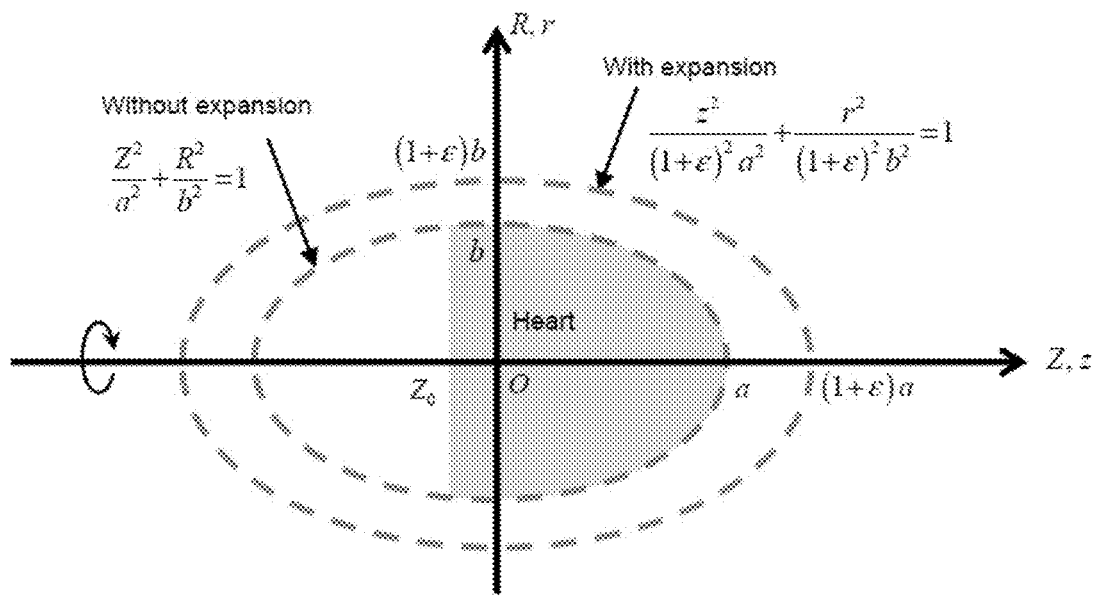
FIG. 7A and FIG. 7B describe the mechanical analysis of a device embodiment.
Figure 7B:
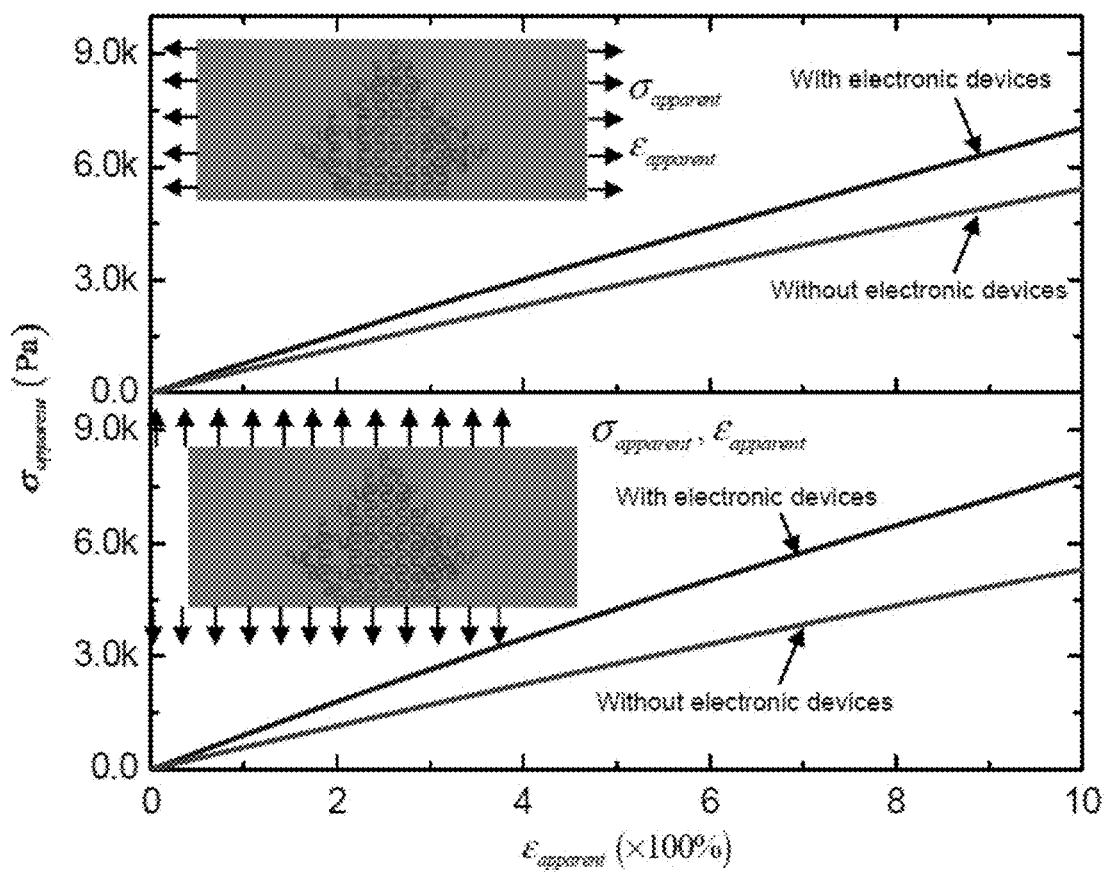

The part of the heart that is covered by the 3D-MIM (FIG. 3A) is approximately a partial axisymmetric ellipsoid with the lengths a and b of semi-principal axes, as shown in FIGS. 7A and 7B. The 3D-MIM on the heart surface is modeled as a membrane, which deforms from $Z^2/a^2 + R^2/b^2 = 1$ when being fabricated on the model to $z^2/[(1+\varepsilon)^2 a^2] + r^2/[(1+\varepsilon)^2 b^2] = 1$ due to the linear expansion E of the heart, where (Z, R) and $(z,r) = [(1+\varepsilon)Z, (1+\varepsilon)R]$ are axial and radial coordinates of the 3D-MIM without and with expansion in the axisymmetric coordinates, respectively. The plane stress state of the 3D-MIM with biaxial linear strain c gives the biaxial stress as $E\varepsilon/(1-v)$, where E and v are the Young's modulus and the Poisson's ratio of the 3D-MIM, respectively. The membrane force, accounting for the change of length due to linear expansion, is $$T = \frac{Et\varepsilon}{(1-v)(1+\varepsilon)},$$

where t is the thickness of the 3D-MIM. For a planar curve $r=r(z)$, the principal curvature along the meridional direction is $-(dr^2/dz^2)/[1+(dr/dz)^2]^{3/2}$ at any point (z, r) on the surface. The other principal curvature along the circumferential direction is given by $r\sqrt{1+(dr/dz)^2}$. For $z=(1+\varepsilon)Z$ and $r=(1+\varepsilon)R$, the two principal curvatures are given by $$\begin{cases} \kappa_1 = \dfrac{a^4 b}{(1+\varepsilon)(a^4 - a^2 X^2 + b^2 X^2)^{3/2}} \\ \kappa_2 = \dfrac{a^2}{(1+\varepsilon)b\sqrt{a^2 + a^2 X^2 + b^2 X^2}} \end{cases}.$$

The pressure on the heart is obtained in terms of the membrane tension and curvatures as $$P = T(\kappa_1 + \kappa_2).$$

Its average over the part of ($Z_0 \leq Z \leq a$, FIG. 7A) of the ellipsoid surface that is in contact with the heart is by $$P_{average} = \frac{\int_{z_0}^{a} P \cdot 2\pi R \sqrt{1 + \left(\frac{dR}{dZ}\right)^2} \, dZ}{\int_{z_0}^{a} 2\pi R \sqrt{1 + \left(\frac{dR}{dZ}\right)^2} \, dZ}.$$

This gives Eq. (1) above, and $$C = \frac{\int_{z_0}^{a} \frac{a^2[(a^2+b^2)a^2 - (a^2-b^2)z^2]}{b(a^4 - a^2 z^2 + b^2 z^2)^{3/2}} R \sqrt{1 + \left(\frac{dR}{dZ}\right)^2} \, dZ}{\int_{z_0}^{a} R \sqrt{1 + \left(\frac{dR}{dZ}\right)^2} \, dZ}.$$

For a=15 mm, b=10 mm and 0 X=−5.5 mm, which best fit the geometric model of the heart, the average pressure in Eq. (1) agrees well with the 3D FEM results, as shown in FIG. 3B.

The analysis above does not account for the effect of electronic devices on the pressure between the 3D-MIM and heart. Such an effect can be estimated from Eq. (1) by replacing the tensile stiffness Et of the 3D-MIM with the effective tensile stiffness of the 3D-MIM with the electronic devices. The inset in FIG. 7B shows an electronic device on a sheet of the membrane material (62.8×24.3×0.15 mm$^3$), consisting of the interconnects and electrodes. All of the interconnects consist of the Au: 120 nm/Cr: 2 nm composite layer sandwiched by 1.2 µm-thick polyimide (PI) layers on each side. The cross section of the electrodes is similar to that of interconnects but without the top 1.2 µm-thick PI layer to expose Au. The sheet is modeled by the 8-node solid element C3D8R, and interconnects and electrodes are modeled by the 4-node shell element S4R in ABAQUS, respectively. FEM gives its tensile stiffness to be approximately 1.5 times that without the electronic devices, as shown in FIG. 7B.

Fabrication Procedures for the 3D-MIM.

I. 3D-MIM with Various Electronics Components Array Appearing in FIG. 2.

p-Doping of Si Nanomembrane.

1. Clean a silicon on insulator (SOI) wafer (320 nm Si on 150 nm buried oxide) with acetone, isopropyl alcohol (IPA) and deionized (DI) water, dehydrate at 110° C. for 5 min.

2. Clean with buffer oxide etch (BOE) 6:1 for 1 min.

3. Expose to diffusive boron source at 1,000° C. for 10 min.

4. Clean the processed wafer with HF for 1 min, RCA 1 for 10 min, RCA 2 for 10 min, and BOE for 1 min.

Preparation of InGaN µ-ILEDs.

5. Spin coating and patterning of photoresist (PR) (AZ 5214 E), for n-contact, on a GaN/Si (111) epi-wafer (Azzurro Semiconductor, GaN: Mg (110 nm)//five repeats of InGaN (3 nm), GaN: Si (10 nm)//GaN: Si (1,700 nm)//AlN: Si/GaN: Si (1,900 nm)//GaN (750 nm)//AlN/AlGaN (300 nm)//Si (111)).

6. Inductively coupled plasma reactive ion etching (ICP-RIE): (a). 3 mTorr, 15 sccm of BCl$_3$, with RF power of 300 W and parallel plate DC voltage of 100 V for 90 s, then (b). 3 mTorr, 15 sccm of Cl$_2$, with RF power of 300 W and parallel plate DC voltage of 100 V for 120 s.

7. Remove native oxide with BOE 10:1 for 120 s.

8. Deposit Ti: 15 nm/Al: 60 nm/Mo: 20 nm/Au: 100 nm with e-beam evaporator.

9. Lift-off (ultrasonic with acetone for 120 s).

10. Annealing at 860° C. for 30 s in N2 ambient.

11. PR patterning for µ-spreading layer.

12. Immerse in HCl:DI=3:1 for 5 min

13. Deposit Ni: 10 nm/Au: 10 nm via e-beam evaporator.

14. Lift-off.

15. Annealing at 500° C. for 10 min in air ambient.

16. PR patterning for p-contact pad.

17. Deposit Ti: 10 nm/Au: 120 nm via e-beam evaporator.

18. Lift-off.

19. Deposit $Si_3N_4$: 300 nm via plasma enhanced chemical vapor deposition (PECVD).

20. PR patterning for anchors.

21. Deposit Ti: 50 nm/Ni: 450 nm via e-beam evaporator.

22. Lift-off.

23. Etching for $Si_3N_4$ mask with reactive ion etching (RIE) ($SF_6$ 40 sccm, pressure 35 mTorr, and RF power 100 W, etch time >3 min).

24. Etching of $Si_3N_4$ and GaN/InGaN/AlN/AlGaN epi-layers with ICP-RIE: (a). 5 mTorr, 25° C., 10 sccm of $BCl_3$, 16 sccm of $Cl_2$, 4 sccm of Ar, 500 W, 300 V, 1 min (b). 5 mTorr, 25° C., 20 sccm of $Cl_2$, sccm of Ar, 500 W, 260 V, 8 min.

25. Immerse in KOH (PSE-200, Transene) with 100° C. for 45 min (100*100 µm), for anisotropic undercut of Si.

26. Ni etching (Transene TFB) for ~200 s (etch rate 3 nm/s at room temp).

27. Etching of $Si_3N_4$ with RIE.

PET Base Layer Preparation.

28. Spin cast poly(dimethylsiloxane) (PDMS) (Sylgard 184, Dow Corning) on glass slide (3,000 rpm, 30 s).

29. Cure PDMS at 70° C. for 2 hours.

30. Laminate poly(ethylene terephthalate) (PET) film with thickness of 2.5 µm on the surface of PDMS.

Transfer Printing of Si Nanomembrane onto PET Base Layer.

31. Pattern PR (S1805, Microposit) with 3 µm pitch dot patterns.

32. Etch silicon by RIE (50 mTorr, 40 sccm $SF_6$, 100 W, 1 min).

33. Undercut buried oxide layer of SOI wafer via dot patterns in HF for 30 min.

34. Spin coat SU-8 2 epoxy (Microchem) on the PET film (3,000 rpm, 30 s).

35. Bake at 65° C. for 30 s.

36. Pick up Si nanomembrane with PDMS stamp from SOI wafer.

37. Print Si layer onto SU-8 layer.

38. Cure SU-8 layer with ultraviolet (UV) light exposure from the back side of the glass slide.

39. Bake at 95° C. for 30 s and remove the stamp.

40. Bake at 150° C. for 15 min.

41. Strip PR with acetone, IPA and DI water.

Si Patterning.

42. Patterning of PR (S1805).

43. Etch silicon by RIE (50 mTorr, 40 sccm SF6, 100 W, 1 min).

44. Strip PR with acetone, IPA and DI water.

1st Metallization.

45. Deposit Cr: 10 nm/Au: 300 nm with e-beam evaporator.

46. Pattern PR.

47. Wet etch Cr/Au.

48. Strip PR with acetone, IPA and DI water.

Transfer Printing of InGaN µ-ILEDs onto PET Planar Substrate.

49. Spin coat SU-8 2 (4,000 rpm, 30 s).

50. Pre-bake at 65° C. for 1 min and 95° C. for 2 min.

51. Print the LEDs with PDMS stamp.

52. Apply UV 365 nm exposure with 150 mJ/cm².

53. Post-bake at 65° C. for 1 min and 95° C. for 2 min.

Passivation for the Printed InGaN µ-ILEDs.

54. Surface modification removal of Si3N4 on top of the LEDs with RIE (40 mTorr, 19.6 sccm $O_2$, 40 sccm $SF_6$, 100 W for 3 min).

55. Spin cast benzocyclobutene (BCB) (Cyclotene 4024-40, Dow) (2,000 rpm, 30 s).

56. Pre-bake at 70° C. for 90 s.

57. Expose with UV from the back side of the sample (123 mJ/cm², 405 nm).

58. Post-bake at 70° C. for 30 s.

59. Develop in developer DS2100 for 70 s.

60. Cure BCB in oxygen-free environment at 210° C. for 120 min.

61. Descuum process using RIE (200 mTorr, 18 sccm $O_2$, 2 sccm $CF_4$, 150 W RF power, 30 s).

2nd Metallization.

62. Deposit Cr: 10 nm/Au: 300 nm with e-beam evaporator.

63. Pattern PR.

64. Wet etch Cr/Au.

65. Strip PR with acetone, IPA and DI water.

66. Dehydrate for 5 min at 150° C.

Encapsulation and Polymer Patterning.

67. Spin coat polyimide (PI) precursor (poly(pyromellitic dianhydride-co-4,4'-oxydianiline), amic acid solution, Sigma-Aldrich) (4,000 rpm, 30 s).

68. Cure PI in oxygen-free environment at 210° C. for 120 min.

69. Deposit Cu: 600 nm via e-beam evaporator.

70. Pattern PR for Cu mask.

71. Wet etch of Cu.

72. Etch polymer with RIE (200 mTorr, 3 sccm $CF_4$ and 19.6 sccm $O_2$, 175 W for 30 min).

73. Wet etch Cu.

Preparation of Elastomer Substrates.

74. Silanize glass slides with tridecafluoro-1,1,2,2-tetrahydrooctyl trichlorosilane (UCT Specialties, LLC).

75. Spin coat silicone elastomer (Ecoflex 00-30, Smooth-on) on the glass slides (500 rpm, 60 s).

76. Cure at room temperature for 3 h.

Transfer Printing onto Elastomer Substrates and Cable Bonding.

77. Release the electronics components array with polymer base and encapsulation layers from the PDMS coated glass slide, using water soluble tape (3M).

78. Deposit Ti: 3 nm/$SiO_2$: 30 nm on the back side of PET, using e-beam evaporator.

79. UV/ozone treatment of the elastomer substrate for 4 min.

80. Print the PET with the electronics components array onto the elastomer substrate.

81. Dissolve the water soluble tape with DI water.

82. Bond thin, flexible heat-seal conductive cable (Elform, HST-9805-210) to the electronics components array using hot iron with firm pressure.

Formation of the 3D Geometry.

83. Prepare the heart model using 3D imaging and 3D printing.

Figure 22:
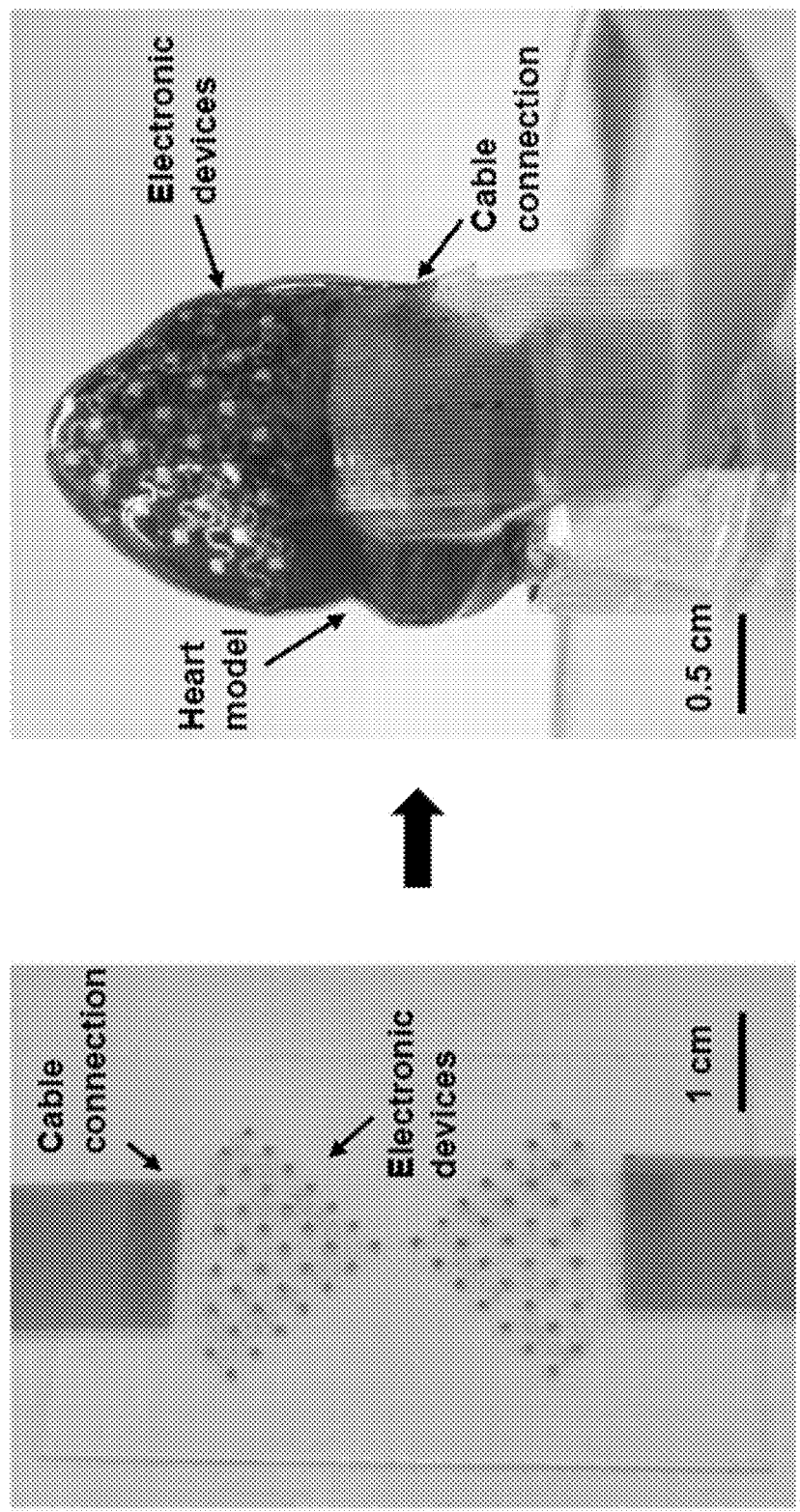
FIG. 22 provides photographs of the equipment used in the lamination process for formation of the 3D geometry.

84. Attach the electronics components arrays with elastomer substrates to the heart model with the front of the electronics components in contact with the heart model (FIG. 22).

85. Additional silicone elastomer structures could be integrated (FIG. 20).

86. Cast silicone elastomer (Ecoflex 00-30, Smooth-on) on top.

87. Cure at room temperature for 24 h.

88. Additional holes could be punched through the passive region of the membrane to allow fluid drainage.

89. Remove the 3D-MIM from the model.

Electrochemical Processes for $IrO_x$ pH Sensors.

90. Dissolve 300 mg of iridium tetrachloride in 200 ml DI water, stir for 15 min.

91. Add 2 ml of aqueous hydrogen peroxide (30%), stir for 10 min.

92. Add 1,000 mg of oxalic acid dehydrate, stir for 10 min.

93. Adjust the pH to 10.5, by adding small amount of anhydrous potassium carbonate.

94. Store at room temperature for 2 days. Successfully prepared solution undergo a color change from yellow to light-violet during the period. Then store the solution in a dark bottle at 4° C. in a refrigerator.

95. Electroplate $IrO_x$ on selected electrodes on the 3D-MIM with a potentiostat (VMP-3, BioLogic Inc.) in constant current mode, using the prepared solution. The voltage across the working and the counter electrodes was maintained around 0.7 V during electroplating. Time duration: 20 min.

II. Electrodes Array for High Precision ECG/pH Mapping.

PI Base Layer Preparation.

1. Clean Si wafer with acetone, IPA and DI water, dehydrate for 5 min at 110° C.
2. Spin coat with poly(methyl methacrylate) (PMMA 495 A2, Microchem) (3,000 rpm, 30 s).
3. Bake at 180° C. for 1 min.
4. Spin coat with PI precursor (4,000 rpm, 30 s).
5. Bake at 110° C. for 30 s.
6. Bake at 150° C. for 5 min.
7. Cure PI in oxygen-free environment at 250° C. for 60 min.

Metallization.

8. Deposit Cr: 10 nm/Au: 300 nm with e-beam evaporator.
9. Pattern PR.
10. Wet etch Cr/Au.
11. Strip PR with acetone, IPA and DI water.
12. Dehydrate for 5 min at 150° C.

Encapsulation and Polymer Patterning.

13. Spin coat PI precursor (4,000 rpm, 30 s).
14. Cure PI in oxygen-free environment at 250° C. for 60 min.
15. Spin coat PR (AZ 4620) (1000 rpm, 60 s).
16. Pattern PR for polymer etching.
17. Etch polymer with RIE (200 mTorr, 20 sccm O2, 150 W for 20 min).
18. Strip PR with acetone, IPA and DI water.

Transfer printing onto elastomer substrates and cable bonding.

19. Partially dissolve PMMA with boiling acetone.
20. Release the electrodes array with PI base and encapsulation layers from the Si wafer, using water soluble tape.
21. Deposit Ti: 3 nm/$SiO_2$: 30 nm on the back side of the PI base layer.
22. UV/ozone treatment of the elastomer substrate for 4 min.
23. Print the electrodes array with PI base and encapsulation layers onto the elastomer substrate.
24. Dissolve the water soluble tape with DI water.
25. Bond thin, flexible heat-seal conductive cable (Elform, HST-9805-210) to the array using hot iron with firm pressure.

Integration to 3D-MIMs and Electroplating of Ira, on Selected Electrodes Complete the Fabrication.

III. Temperature Sensors Array.

PI Base Layer Preparation.

1. Clean Si wafer with acetone, IPA and DI water, dehydrate for 5 min at 110° C.
2. Spin coat with PMMA 495 A2 (3,000 rpm, 30 s).
3. Bake at 180° C. for 1 min.
4. Spin coat with PI precursor (4,000 rpm, 30 s).
5. Bake at 110° C. for 30 s.
6. Bake at 150° C. for 5 min.
7. Cure PI in oxygen-free environment at 250° C. for 60 min.

1st Metallization.

8. Deposit Cr: 5 nm/Au: 40 nm with e-beam evaporator.
9. Pattern PR.
10. Wet etch Cr/Au.
11. Strip PR with acetone, IPA and DI water.
12. Dehydrate for 5 min at 150° C.

Isolate 1st Metal and Pattern Via Holes.

13. Spin coat with PI precursor.
14. Bake at 110° C. for 30 s.
15. Bake at 150° C. for 5 min.
16. Cure PI in oxygen-free environment at 250° C. for 60 min.
17. Spin coat (3000 rpm, 30 s) and pattern PR (AZ4620).
18. RIE (50 mTorr, 20 sccm $O_2$, 150 W, 35 min).

2nd Metallization.

19. Deposit Cr: 5 nm/Au: 200 nm with e-beam evaporator.
20. Pattern PR.
21. Wet etch Cr/Au.
22. Strip PR with acetone, IPA and DI water.
23. Dehydrate for 5 min at 150° C.

Encapsulation and polymer patterning.

24. Spin coat with PI precursor.
25. Bake at 110° C. for 30 s.
26. Bake at 150° C. for 5 min.
27. Cure PI in oxygen-free environment at 250° C. for 60 min.
28. Pattern PR AZ4620.
29. RIE (50 mTorr, 20 sccm O2, 150 W, 35 min).

Transfer Printing onto Elastomer Substrates and Cable Bonding.

30. Partially dissolve PMMA with boiling acetone.
31. Release the temperature sensors array with PI base and encapsulation layers from the Si wafer, using water soluble tape.
32. Deposit Ti: 3 nm/$SiO_2$: 30 nm on the back side of the PI base layer.
33. UV/ozone treatment of the elastomer substrate for 4 min.
34. Print the temperature sensors array with PI base and encapsulation layers onto the elastomer substrate.
35. Dissolve the water soluble tape with DI water.
36. Bond thin, flexible heat-seal conductive cable (Elform, HST-9805-210) to the array using hot iron with firm pressure.

Integration to 3D-MIMs Completes the Fabrication.

IV. Si Strain Sensors Array.

p-Doping of Si Nanomembrane.

1. Clean a SOI wafer with acetone, isopropyl alcohol (IPA), deionized (DI) water, dehydrate at 110° C. for 5 min.
2. Clean with BOE (6:1) for 1 min.
3. Expose to diffusive boron source at 1,000° C. for 10 min.
4. Clean the processed wafer with HF for 1 min, RCA 1 for 10 min, RCA 2 for 10 min, and BOE for 1 min.

PI Base Layer Preparation and Transfer Printing of Si Nanomembrane.

5. Pattern PR (S1805, Microposit) with 3 μm pitch dot patterns.
6. Etch silicon by RIE (50 mTorr, 40 sccm $SF_6$, 100 W, 1 min).
7. Undercut buried oxide layer of SOI wafer via dot patterns in HF for 30 min.
8. Clean a bare Si wafer with acetone, IPA and DI water, dehydrate for 5 min at 110° C.
9. Spin coat with PMMA, (3,000 rpm, 30 s).
10. Bake at 180° C. for 1 min.
11. Spin coat with PI precursor (4,000 rpm, 30 s) and anneal at 110° C. for 40 s.
12. Pick up Si nanomembrane with PDMS stamp from SOI wafer.
13. Print Si layer onto PI layer.
14. Bake at 110° C. for 30 s and release the stamp.
15. Bake at 150° C. for 15 min.
16. Strip PR with acetone, IPA and DI water.
17. Cure PI in oxygen-free environment at 250° C. for 60 min.

Si Patterning.

18. Patterning of PR (S1805).
19. Etch Si by RIE (50 mTorr, 40 sccm SF6, 100 W, 1 min).
20. Strip PR with acetone, IPA and DI water.

Metallization.

21. Deposit Cr: 10 nm/Au: 300 nm with e-beam evaporator.
22. Pattern PR.
23. Wet etch Cr/Au.
24. Strip PR with acetone, IPA and DI water.
25. Dehydrate for 5 min at 150° C.

Encapsulation and Polymer Patterning.

26. Spin coat PI precursor (4,000 rpm, 30 s).
27. Cure PI in oxygen-free environment at 250° C. for 60 min.
28. Spin coat PR (AZ 4620) (1000 rpm, 60 s).
29. Pattern PR for polymer etching.
30. Etch polymer with RIE (200 mTorr, 20 sccm $O_2$, 150 W for 20 min).
31. Strip PR with acetone, IPA and DI water.

Transfer Printing onto Elastomer Substrates and Cable Bonding.

32. Partially dissolve PMMA with boiling acetone.
33. Release the strain sensors array with PI base and encapsulation layers from the Si wafer, using water soluble tape.
34. Deposit Ti: 3 nm/$SiO_2$: 30 nm on the back side of the PI base layer.
35. UV/ozone treatment of the elastomer substrate for 4 min.
36. Print the strain sensors array with PI base and encapsulation layers onto the elastomer substrate.
37. Dissolve the water soluble tape with DI water.
38. Bond thin, flexible heat-seal conductive cable (Elform, HST-9805-210) to the array using hot iron with firm pressure.

Integration to 3D-MIMs Completes the Fabrication.

V. μ-ILEDs Array for Optical Experiments

Preparation of AlInGaP μ-ILEDs.

1. Prepare epitaxial stacks of p-GaAs:C (50 nm)//$Al_{0.45}Ga_{0.55}As$:C (800 nm)//$In_{0.5}Al_{0.5}P$:Zn (200 nm)//$Al_{0.25}Ga_{0.25}In_{0.5}P$ (6 nm)//four repeats of $In_{0.56}Ga_{0.44}P$ (6 nm), $Al_{0.25}Ga_{0.25}In_{0.5}P$ (6 nm)//$In_{05}Al_{0.5}P$:Si (200 nm)//$Al_{0.45}Ga_{0.55}As$:Si (800 nm)//n-GaAs:Si (500 nm)//$Al_{0.96}Ga_{0.04}As$ (500 nm) on a GaAs wafer.
2. Deposit $SiO_2$ with PECVD.
3. Pattern PR for mesa etch.
4. Etch $SiO_2$ with BOE.
5. Etch with ICP-RIE (2 mTorr, 4 sccm of $Cl_2$, 2 sccm of $H_2$, 4 sccm of Ar, RF1:100 W, RF2: 500 W, ~5 min) to expose n-GaAs.
6. Strip PR with acetone, IPA and DI water.
7. Pattern PR for n-GaAs etch.
8. Wet etch with $H_3PO_4$:$H_2O_2$:$H_2O$ (1:13:12) (~10 s).
9. Strip PR with acetone, IPA and DI water.
10. Pattern PR for n-contact.
11. Clean the surface of n-GaAs with HCl:DI water (1:1) for 30 s.
12. Deposit Pd: 5 nm/Ge: 35 nm/Au: 70 nm with e-beam evaporator.
13. Lift-off.
14. Anneal at 175° C. for 60 min under $N_2$ ambient.
15. Pattern PR for p-contact.
16. Etch with BOE for 30 s.
17. Clean the surface of p-GaAs with HCl:DI water (1:1) for 30 s.
18. Deposit Pt: 10 nm/Ti: 40 nm/Pt: 10 nm/Au: 70 nm with e-beam evaporator.
19. Lift-off.
20. Pattern PR for protective anchors.
21. Dip in diluted HF (49%, diluted 100:1) for ~2 hrs to remove the $Al_{0.96}Ga_{0.04}As$ (sacrificial layer) underneath the μ-ILEDs.

Polymer Base Layer Preparation and Transfer Printing of AlInGaP μ-ILEDs.

22. Deposit Cr: 10 nm on glass slide.
23. Pattern PR for Cr marker.
24. Wet etch Cr.
25. Strip PR with acetone, IPA and DI water.
26. Spin coat PMMA 495 A2 (3000 rpm, 30 s).
27. Bake at 180° C. for 1 min.
28. Spin coat SU-8 2 (4,000 rpm, 30 s).
29. Pre-bake at 65° C. for 1 min and 95° C. for 2 min.
30. Print μ-ILEDs with PDMS stamp.
31. Apply UV 365 nm exposure with 150 mJ/$cm^2$.
32. Post-bake at 65° C. for 1 min and 95° C. for 2 min and remove the PDMS stamp.
33. Strip PR with acetone, IPA and DI water.

Passivation for the AlInGaP μ-ILEDs.

34. Spin coat SU-8 2 (2,000 rpm, 30 s).
35. Pre-bake at 65° C. for 2 min and 95° C. for 3 min.
36. Expose with UV 365 nm with 150 mJ/$cm^2$ for making via hole.
37. Post-bake at 70° C. for 40 s.
38. Develop in SU 8 developer for 30 s.
39. Bake at 150° C. for 30 min.

Metallization.

40. Deposit Cr: 10 nm/Au: 300 nm with e-beam evaporator.
41. Pattern PR.

Figure 8A:
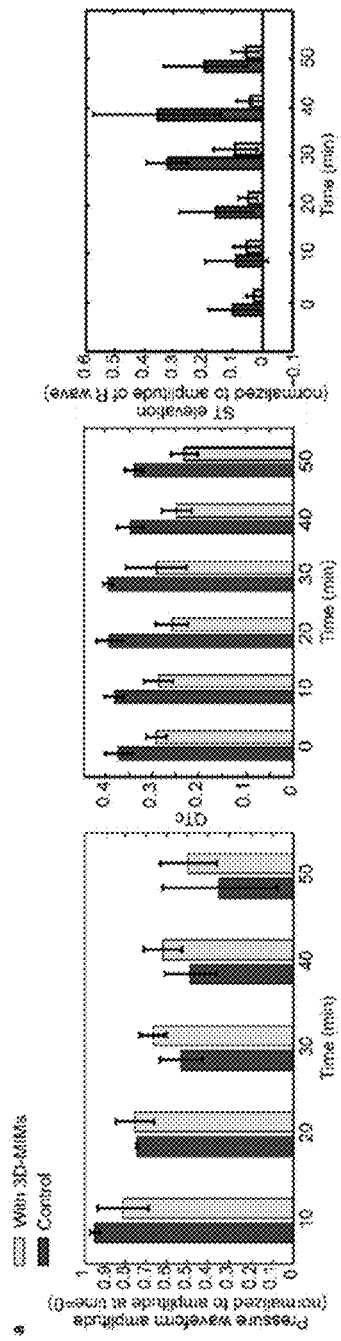
FIG. 8A and FIG. 8B illustrate the stability of a working heart with the 3D-MIMs applied.
Figure 8B:
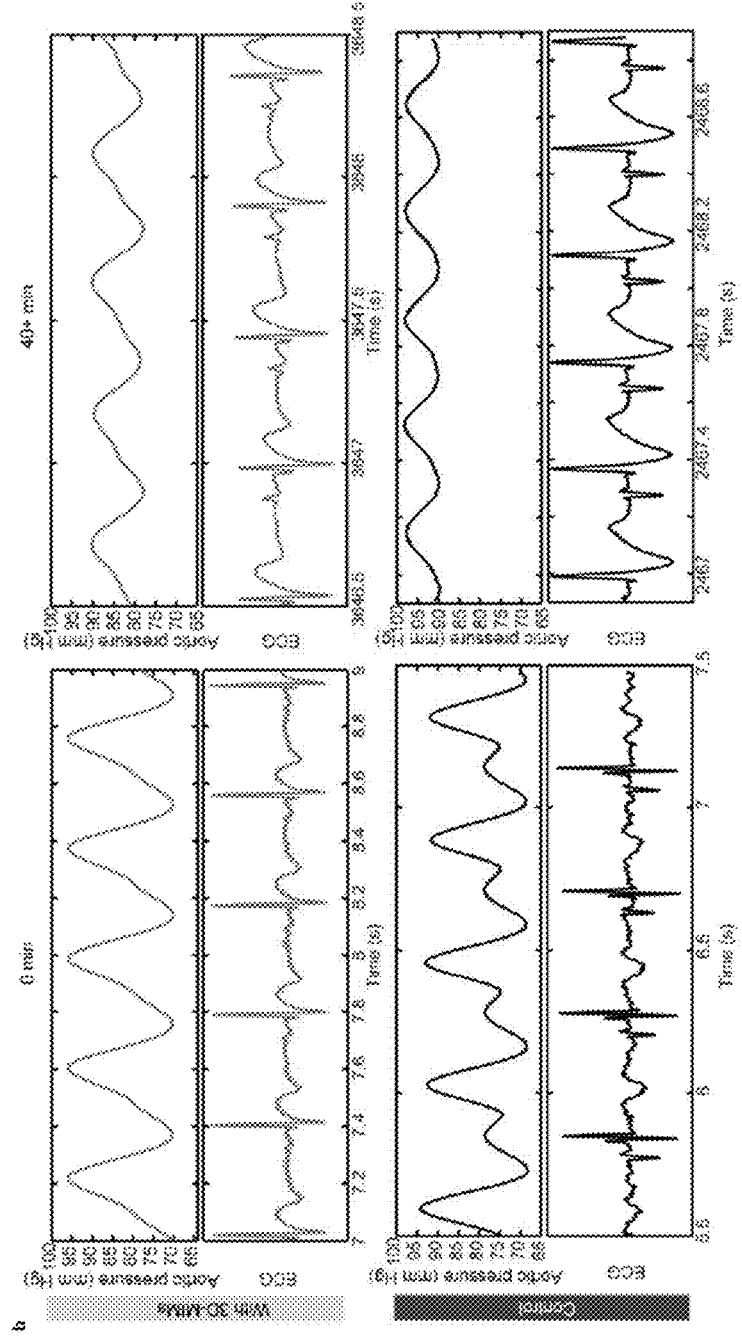
Figure 18:
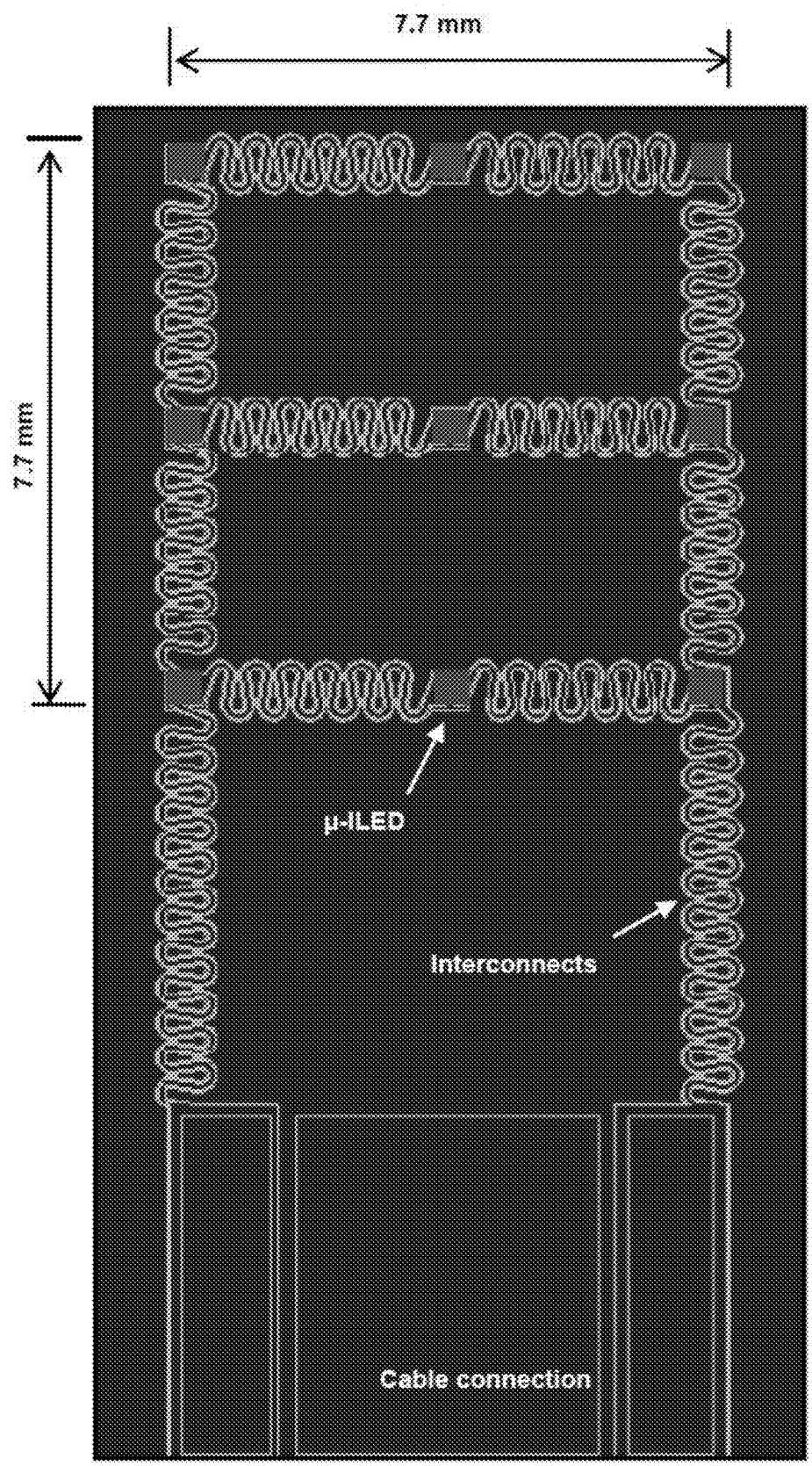
FIG. 18 provides an overview of the design of µ-ILEDs array for optical mapping experiments.
Figure 19A:
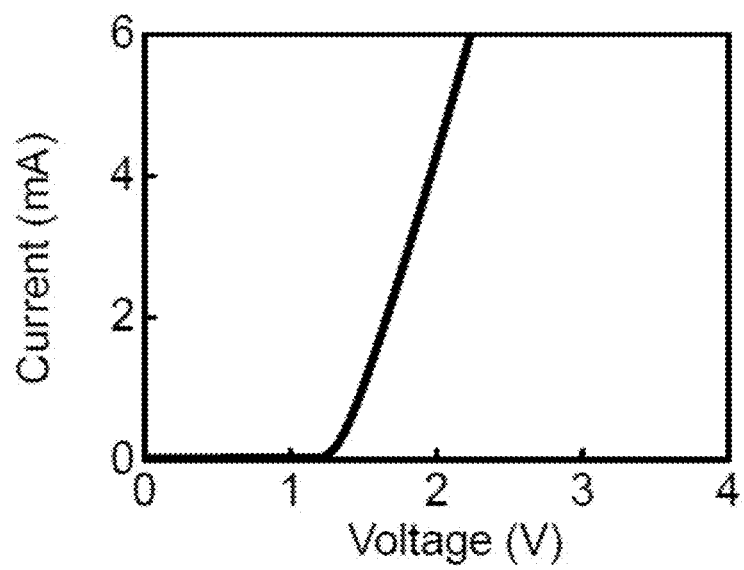
FIG. 19A, FIG. 19B and FIG. 19C provide data showing characteristics of the µ-ILEDs for optical mapping experiments. I-V characteristics (FIG. 19A), emission spectrum (FIG. 19B) and optical output power (FIG. 19C) of a representative µ-ILED integrated on 3D-MIM for optical mapping experiments.
Figure 19B:
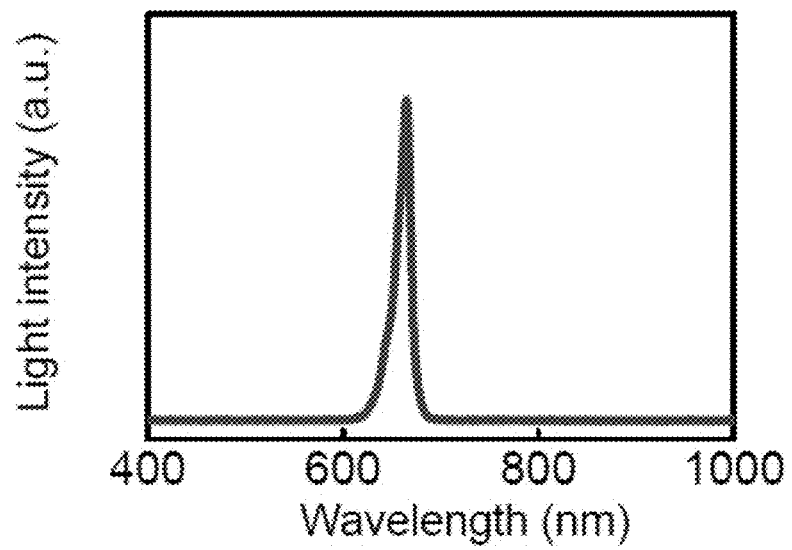
Figure 19C:
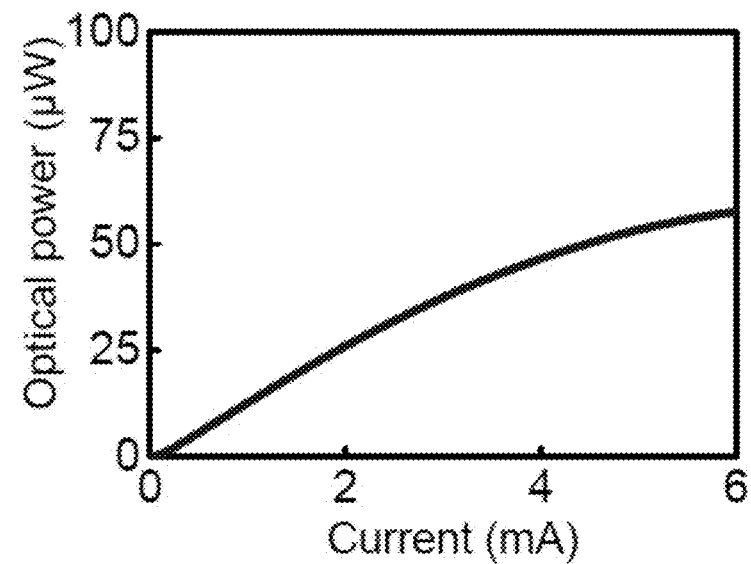

42. Wet etch Cr/Au.
43. Remove PR with AZ 400T.
Encapsulation and Polymer Patterning.
44. Dehydrate for 5 min at 150° C.
45. Spin coat SU8-2 (2000 rpm, 30 s).
46. Bake at 65° C. for 1 min and 95° C. for 2 min.
47. Blow with $N_2$ gas.
48. Spin coat PI precursor (3,000 rpm, 30 s).
49. Cure PI in oxygen-free environment at 250° C. for 60 min.
50. Spin coat PR (AZ 4620) (1000 rpm, 60 s).
51. Pattern PR for polymer etching.
52. Etch polymer with RIE (200 mTorr, 20 sccm $O_2$, 150 W for 20 min).
53. Strip PR with acetone, IPA and DI water.
Transfer Printing onto Elastomer Substrates and Cable Bonding.
54. Partially dissolve PMMA with boiling acetone.
55. Release the μ-ILEDs array with polymer base and encapsulation layers from the Si wafer, using water soluble tape.
56. Deposit Ti: 3 nm/$SiO_2$: 30 nm on the back side of the PI base layer.
57. UV/ozone treatment of the elastomer substrate for 4 min.
58. Print the μ-ILEDs array with polymer base and encapsulation layers onto the elastomer substrate.
59. Dissolve the water soluble tape with DI water.
60. Bond thin, flexible heat-seal conductive cable (Elform, HST-9805-210) to the electronics components array using hot iron with firm pressure.
Integration to 3D-MIMs Completes the Fabrication.
Figure Captions.
FIGS. 7A and 7B: Mechanical analysis of the devices. FIG. 7A: Schematic illustration of the partial axisymmetric ellipsoid with the lengths a and b of semiprincipal axes for the analytic model. FIG. 7B: The comparison of the stiffness of the 3D-MIM with and without electronic devices along two directions.
FIGS. 8A and 8B: Stability of working heart with the 3D-MIMs applied. FIG. 8A: A chronological comparison of the pressure waveform at the aorta and electrophysiological indicators of ischemia during the working heart preparation with and without the 3D-MIMs on the heart. Signs of ischemia include a decrease in the pressure waveform, which is an indication of contractility, a decrease in the corrected QT interval of the far field electrogram and an elevation of the ST segment of the far-field electrogram. The temporal pattern for the control hearts indicates that the working heart preparation is not stable across the hour even without the 3D-MIM, however the pressure waveform and the ST elevation do not seem to indicate that the 3D-MIM is impairing functionality. The QTc is shortened in the 3D-MIMs group, which does suggest that there may be some impact on repolarization that could be investigated further. FIG. 8B: Example traces at the beginning and end of the stability hour for the 3D-MIM group and the control group.
FIG. 9: Design of the electrodes array for high precision ECG and pH mappings. The insets show magnified image of the Au electrode, electrode with electrodeposited $IrO_x$, and interconnects with PI base and encapsulation layers, respectively.
FIG. 10: Electrochemical impedance spectroscopy (EIS) data of a representative 3D-MIM Au electrode measured in phosphate buffered saline.
FIGS. 11A, 11B and 11C: Comparison of signal quality of 3D-MIMs electrophysiological measurements under beating and arrested heart conditions. Surface electrogram recordings under both beating (FIG. 11A) and arrested (FIG. 11B) conditions capture various morphologies of the QRS and T waves. FIG. 11C: Comparison of the signal to noise ratio (SNR) of the measurements.
FIGS. 12A, 12B and 12C: Demonstration of spatial mapping of repolarization p parameters with 3D-MIMs. FIG. 12A: Representative electrical trace from the device overlaid with a corresponding optical trace for validation defines activation recovery interval (ARI) from max −dV/dt to the max dV/dt after the QRS complex and defines action potential duration to 80% repolarization (APD80) from max dV/dt to 80% recovery. FIG. 12B: Correlation between the activation recovery interval from the electrograms and the corresponding optical action potential duration from a variety of conditions. FIG. 12C: Representative spatial reconstruction of repolarization parameters with the electrical device and the optical mapping.
FIG. 13: Calibration of pH sensors. Calibration between open circuit potential (OCP) (IrOx electrode vs. Ag/AgCl reference electrode) and pH (obtained from glass electrode) values showed responses of 68.9±8.6 mV/pH over 32 channels at 37° C. in Tyrode's solution.
FIG. 14: Design of the temperature sensor array. The inset shows the magnified view of a Au serpentine trace for temperature sensing.
FIG. 15: Calibration of the temperature sensors. Calibration is performed by submerging the 3D-MIM with 16 temperature sensors into a digital circulating water bath (Fisher Scientific 15-474-100). The resistance is measured with a custom built system based on National Instruments PXI-6289 board and the temperature is controlled and monitored through the water bath. Linear fit is applied to each sensor to obtain the relationship between resistance and temperature.
FIG. 16A and FIG. 16B provide images of devices incorporating a Si strain sensor array. FIG. 16A: Design and optical microscope image of the Si strain sensor array. Inset: optical microscope image of 3 p-doped Si piezoresistors arranged in a rosette configuration. Longitudinal axes of piezoresistor 1 and 3 correspond to <110> crystalline directions, longitudinal axis of piezoresistor 2 corresponds to <100> direction. FIG. 16B: Image of a 3D-MIM with Si strain sensors array integrated on a Langendorff-perfused rabbit heart.
FIG. 17: Tensile test of the Si strain sensors. Fractional resistance changes of the 3 Si piezoresistors showed in FIG. 16A, as functions of uniaxial tensile strain applied in direction parallel to the longitudinal axis of piezoresistor 1. The calculated effective longitudinal gauge factor is 0.33, and effective transverse gauge factor is ~−0.06, for piezoresistors aligned to <110> directions (1 and 3).
FIG. 18: Design of the μ-ILEDs array for optical mapping experiments.
FIGS. 19A, 19B and 19C: Characteristics of the μ-ILEDs for optical mapping experiments. I-V characteristics (FIG. 19A), emission spectrum (FIG. 19B) and optical output power (FIG. 19C) of a representative μ-ILED integrated on 3D-MIM for optical mapping experiments.
FIG. 20: Fixtures for maneuvering the 3D-MIM for Langendorff-perfused rabbit heart experiments. 6 silicone straps were integrated into the 3D-MIM to provide support and control of the opening of the device. Each strap is attached to a custom made fixture for independent control.
FIG. 21: Experimental setup for Langendorff-perfused rabbit heart experiments and optical mapping.

FIG. 22: Lamination process for formation of the 3D geometry. The electronic devices are attached to a desired 3D printed model of the heart, with the sensors in direct contact with the surface, followed by casting another layer of elastomer on top.

Example 2: Devices and Methods for Low-Energy Defibrillation

The biomedical devices and methods of the present invention support a broad range of therapeutic and diagnostic applications including multiparametric cardiac mapping and stimulation. This example provides experimental results demonstrating the efficacy of the present devices for use in low-energy defibrillation and thermal sensing via establishing a conformal interface with large areas of cardiac tissue.

Figure 23:
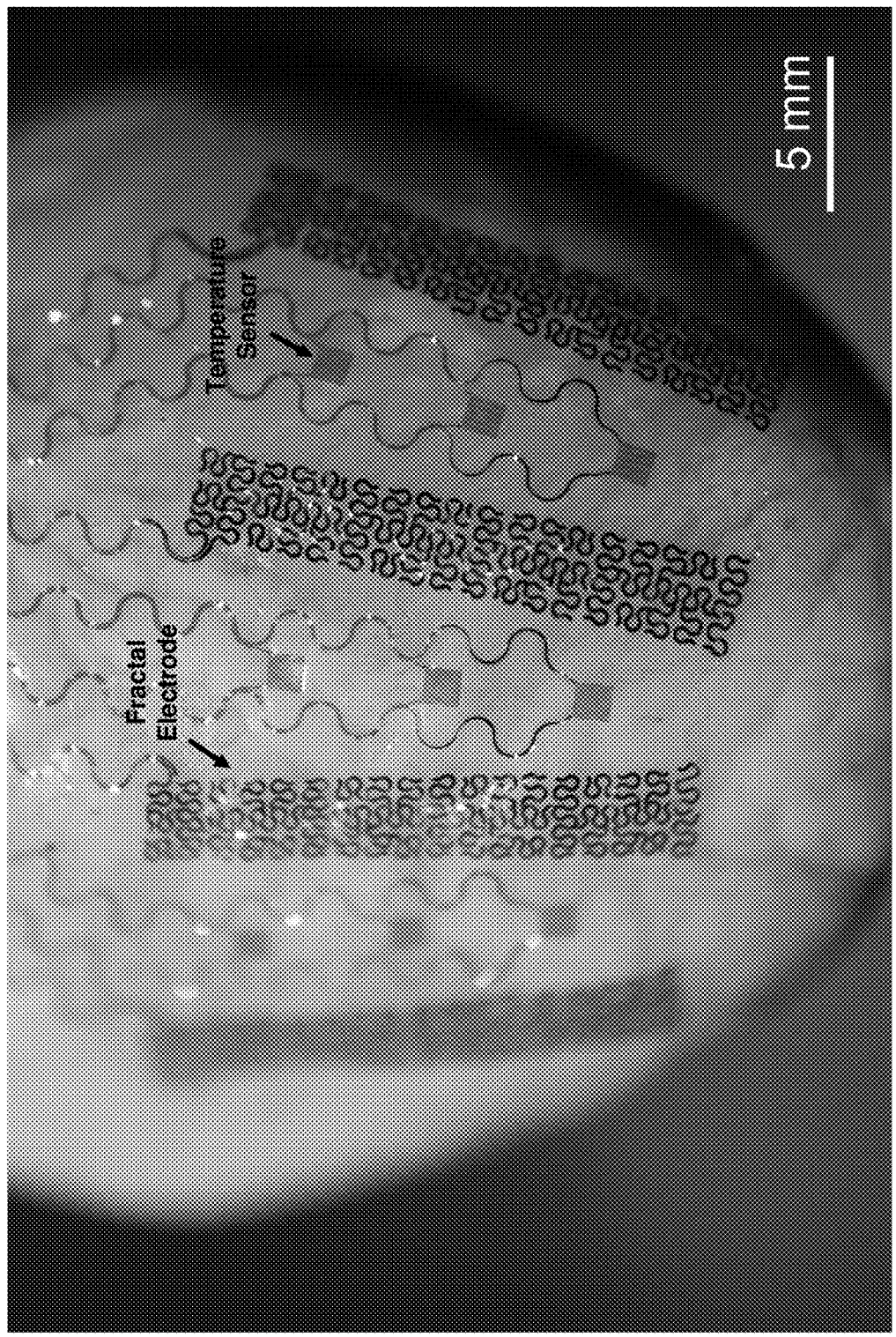
FIG. 23 provides an optical image of a device for delivering epicardial electro-therapy.
Figure 24:
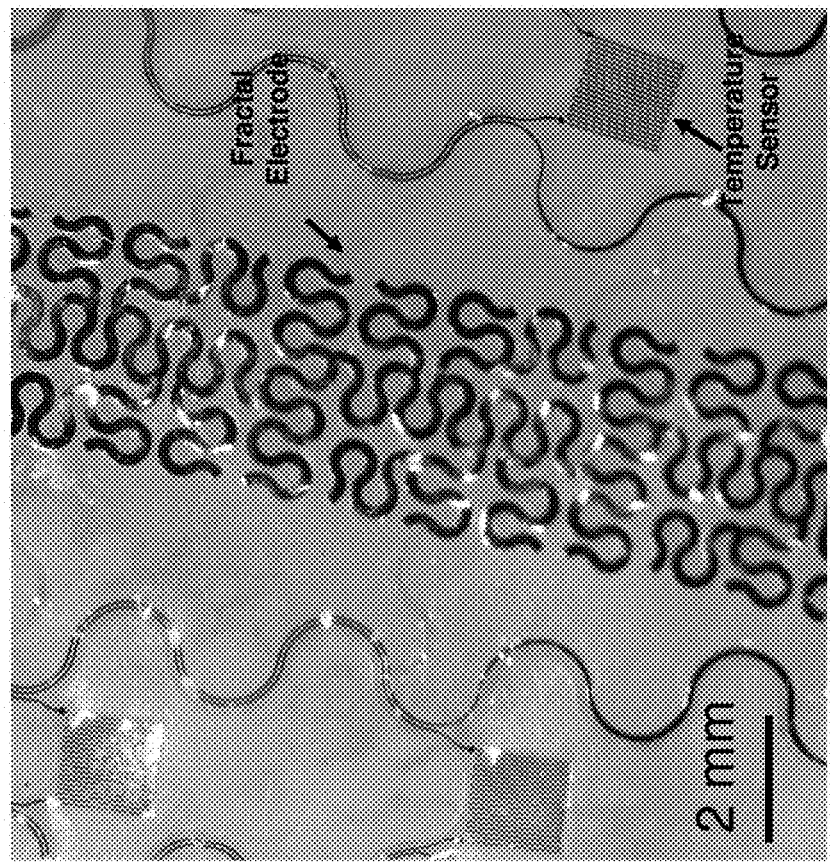
FIG. 24 provides optical images of a device for delivering epicardial electro-therapy.
Figure 24:
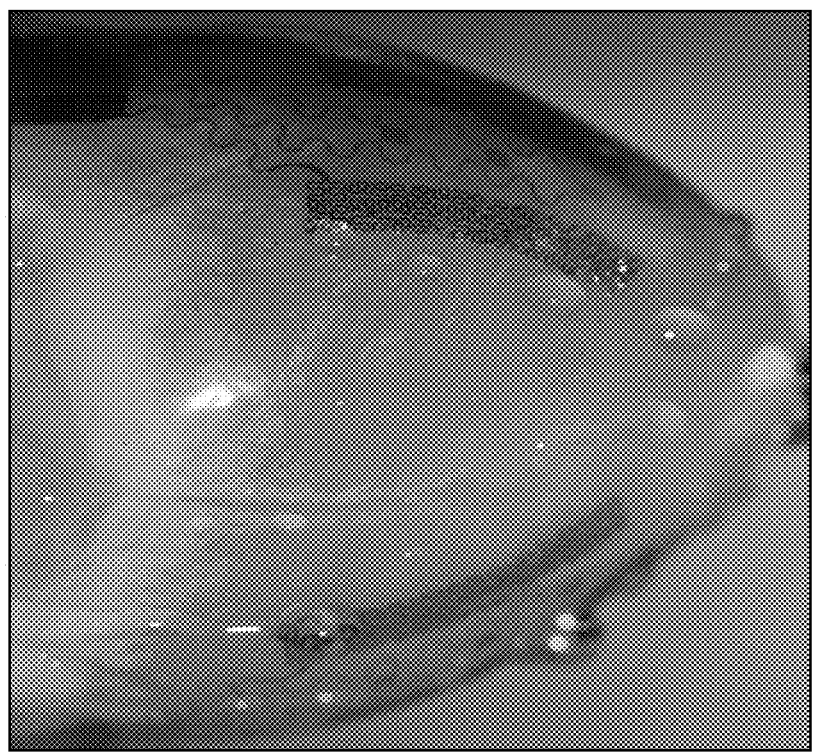

FIGS. 23 and 24 provide optical images of a 3D-multifunctional integumentary device of the invention. FIG. 23 shows the 3D-multifunctional integumentary device integrated with a rabbit heart demonstrating the ability to establish conformal contact with large areas of the heart surface. In this figure, the black arrows indicate the defibrillation electrodes having a fractal-based design and temperature sensor arrays. The defibrillation electrodes are for delivering epicardial electrotherapy and the temperature sensors provide for feedback of tissue response. The left panel of FIG. 24 provides an alternate view demonstrating that the 3D-multifunctional integumentary device is positioned to entirely envelop the rabbit heart wherein defibrillation electrodes and temperature sensors cover both anterior and posterior surfaces of the heart. The right panel of FIG. 24 provides a magnified view of the electronic devices wherein the black arrows indicate the defibrillation electrodes having a fractal-based design approximating the height of the ventricle and the temperature sensor arrays. The fractal electrodes provide a space filling structure for delivering epicardial electro-therapy to local tissue regions, and the temperature sensors are constructed as resistive structures for monitoring feedback of the tissue response.

Figure 25:
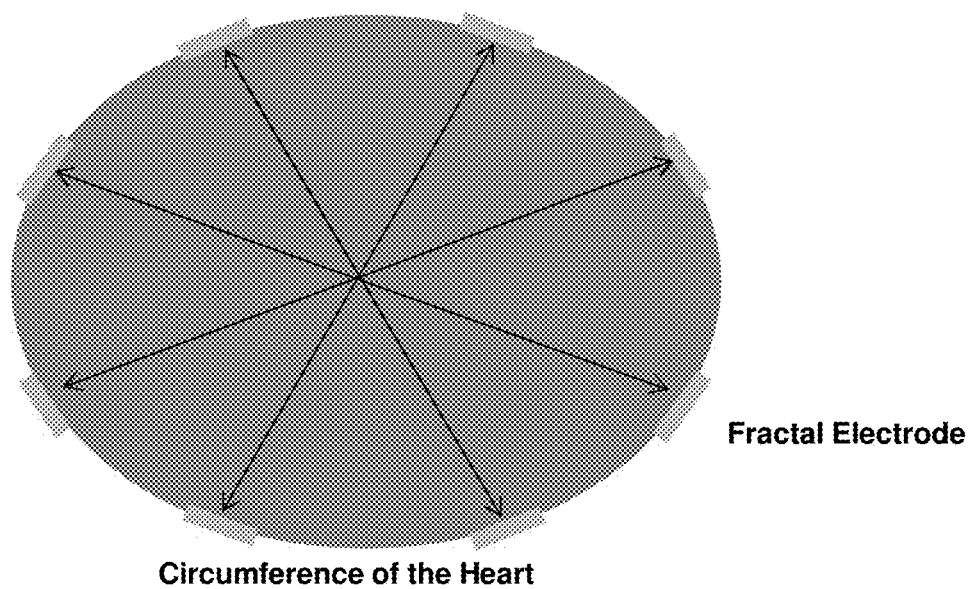
FIG. 25 illustrates an overview of strategies for low-energy defibrillation of cardiac tissue.

FIG. 25 illustrates a variety of approaches for low-energy defibrillation of cardiac tissue using the present devices and methods. FIG. 25 provides a schematic illustration of a multi-vector, rotating field electrical stimulation scheme for low-energy defibrillation of cardiac tissue.

Figure 26:
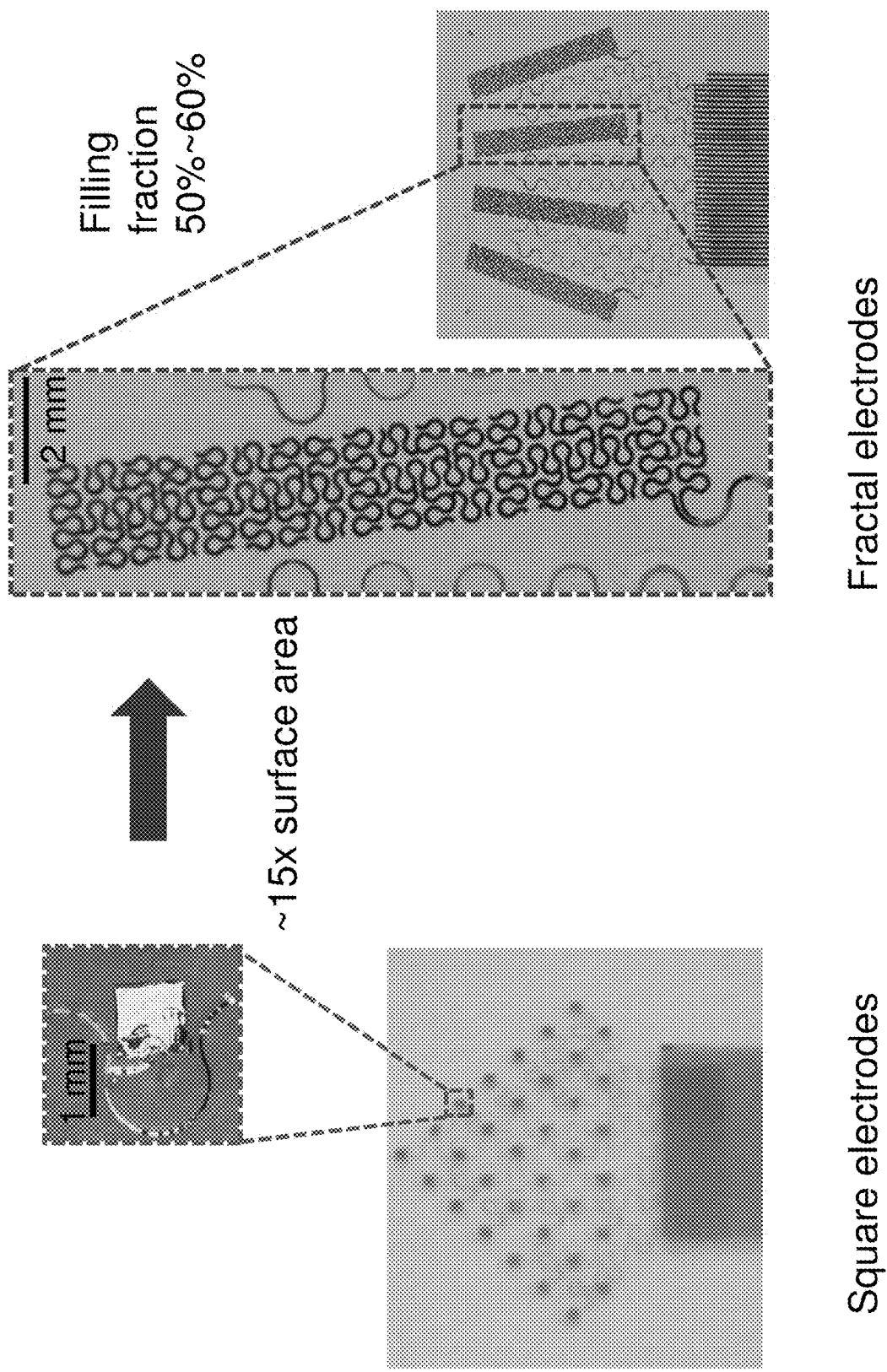
FIG. 26 provides optical images comparing electrode configurations of two device embodiments.

FIG. 26 provides optical images comparing defibrillation electrode geometries for 3D multifunctional integumentary devices of the present invention. The left panel of FIG. 26 shows a device incorporating defibrillation electrodes having a square geometry. The right panel of FIG. 26 shows a device incorporating defibrillation electrodes having fractal-based geometry providing a space filling configuration with a filling fraction between 50% and 60%. As shown in these figures, the defibrillation electrodes having fractal-based geometry provide an approximate 15-fold increase in surface area as compared to the electrodes having a square geometry.

Figure 27:
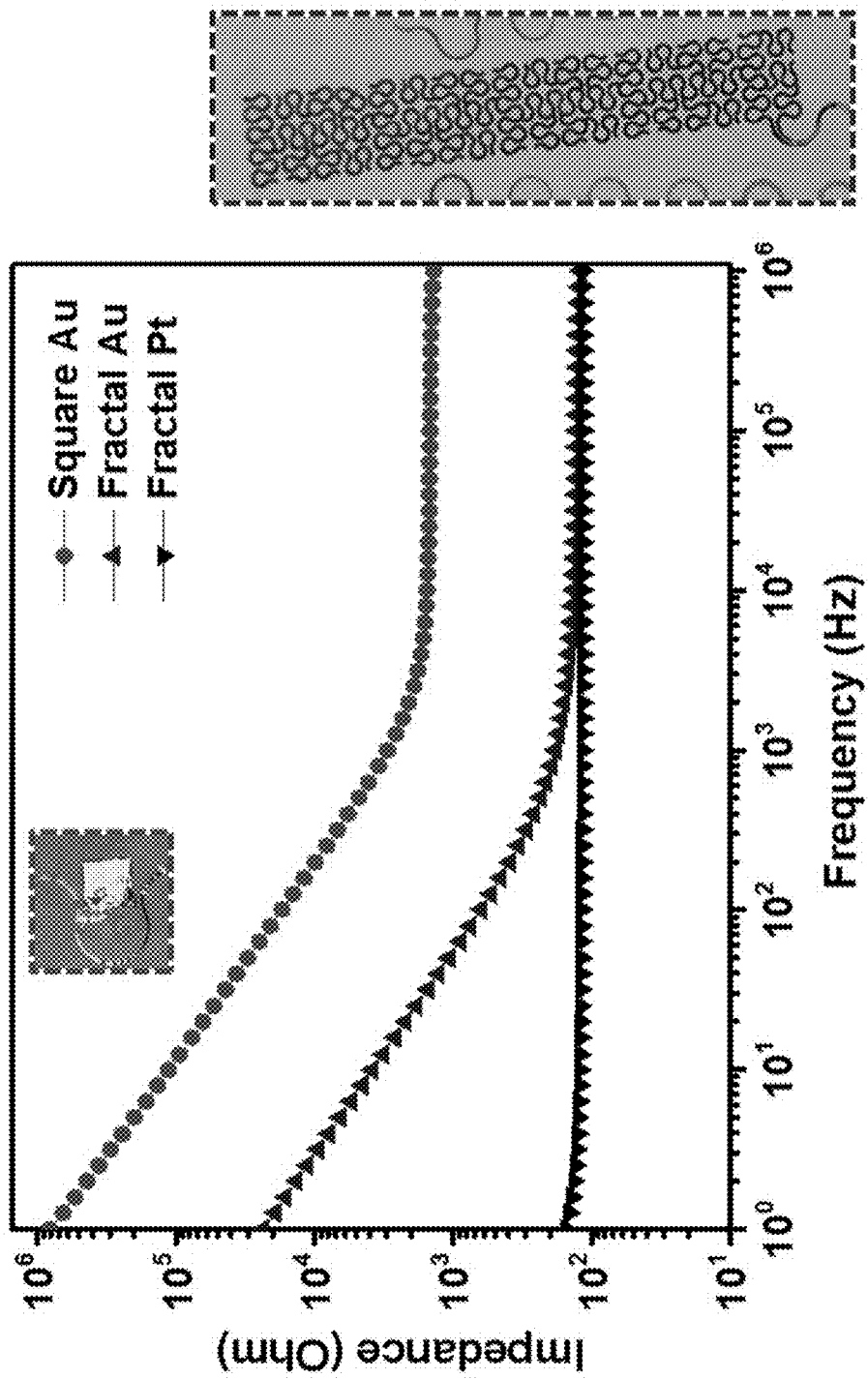
FIG. 27 provides data showing a comparison of electrical impedance between gold square electrodes, gold fractal-like electrodes and platinum fractal-like electrodes.

FIG. 27 provides experimental results showing a comparison of electrochemical impedance spectra for three types of defibrillation electrodes: gold square electrodes (Square Au), gold fractal-based electrodes (Fractal Au) and fractal-based electrodes with electroplated platinum surfaces (Fractal Pt). In FIG. 27, impedance (Ohm) is plotted as a function of frequency (Hz) for the three defibrillation electrode geometries evaluated. The platinum was electrodeposited on a gold surface using 5 mM $H_2PtCl_6$ + 1.2 mM HCl, −0.1 V vs Ag/AgCl, for 30 min. [See, e.g., *J. Phys. Chem. C* 117, 18957 (2013)]

$$Pt^{IV}Cl_6^{2-} + 2e^- \rightarrow Pt^{II}Cl_4^{2-} + 2Cl^-$$

$$E^c = 0.529 V_{Ag/AgCl} \quad (i)$$

$$Pt^{IV}Cl_6^{2-} + 4e^- \rightarrow Pt^0 + 3Cl^- \quad E^c = 0.547 V_{Ag/AgCl} \quad (ii)$$

$$Pt^{II}Cl_4^{2-} + 2e^- \rightarrow Pt^0 + 4Cl^- E^c = 0.561 V_{Ag/AgCl} \quad (iii)$$

Figure 28:
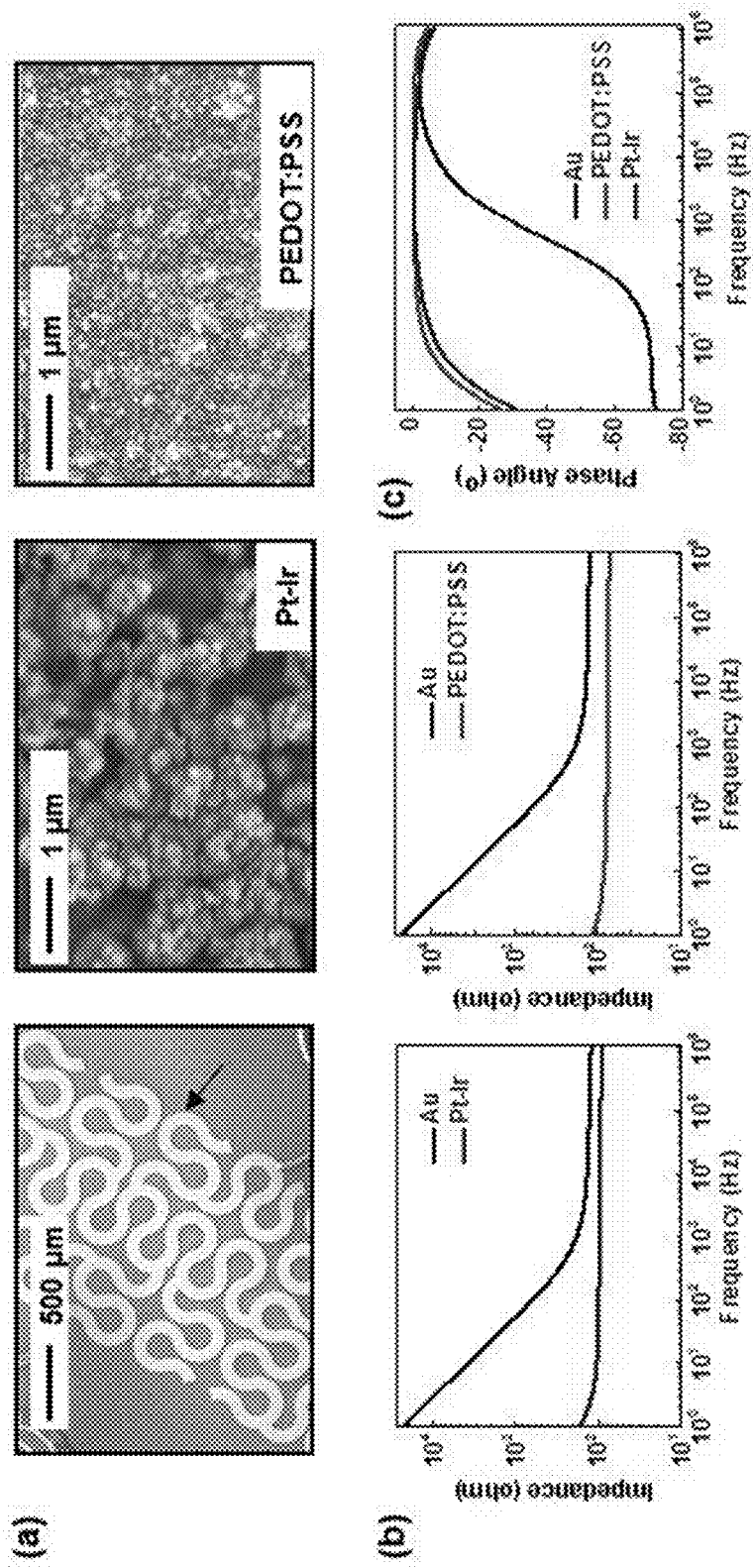
FIG. 28 provides micrographs of fractal-like gold electrodes coated with low impedance materials (Pt—Ir; poly (3,4-ethylenedioxythiophene)polystyrene sulfonate (PEDOT:PSS)) and corresponding electrochemical impedance spectroscopy data.
Figure 29:
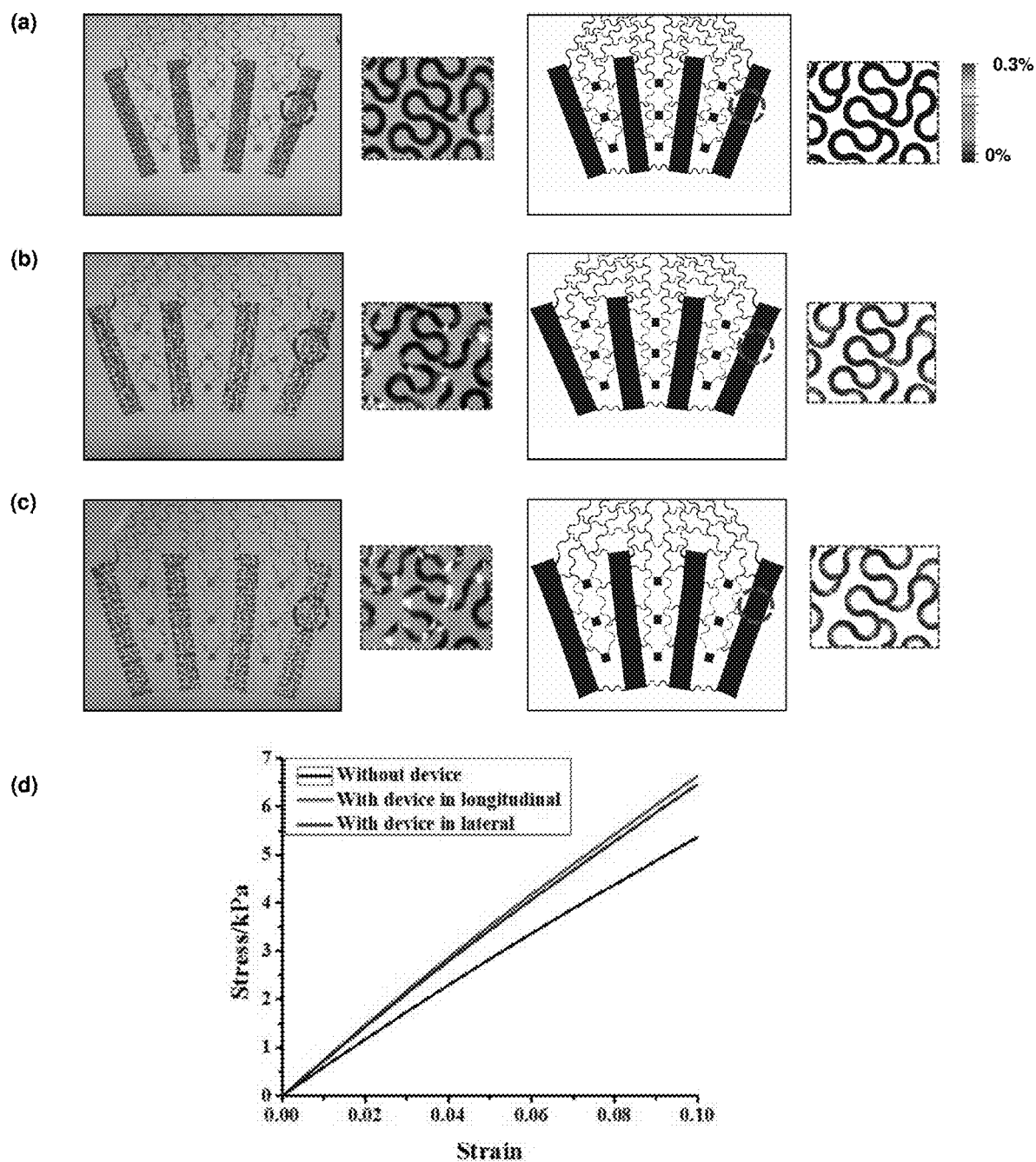
FIG. 29 provides mechanical stress versus strain data for the fractal-like electrodes.

As illustrated in FIG. 27, the defibrillation electrodes having the fractal-based geometry exhibit a significantly smaller impedance than the square electrodes. At low frequencies, the platinum-plated fractal-like electrodes exhibit an even smaller impedance than the gold fractal-like electrodes, while the impedance of the fractal-like electrodes at high frequencies approach each other. FIG. 28 provides micrographs of the fractal-like gold electrodes coated with low impedance materials (Pt—Ir, PEDOT:PSS) and corresponding electrochemical impedance spectroscopy data. FIG. 29 provides mechanical stress versus strain data for the fractal-like electrodes.

Figure 30:
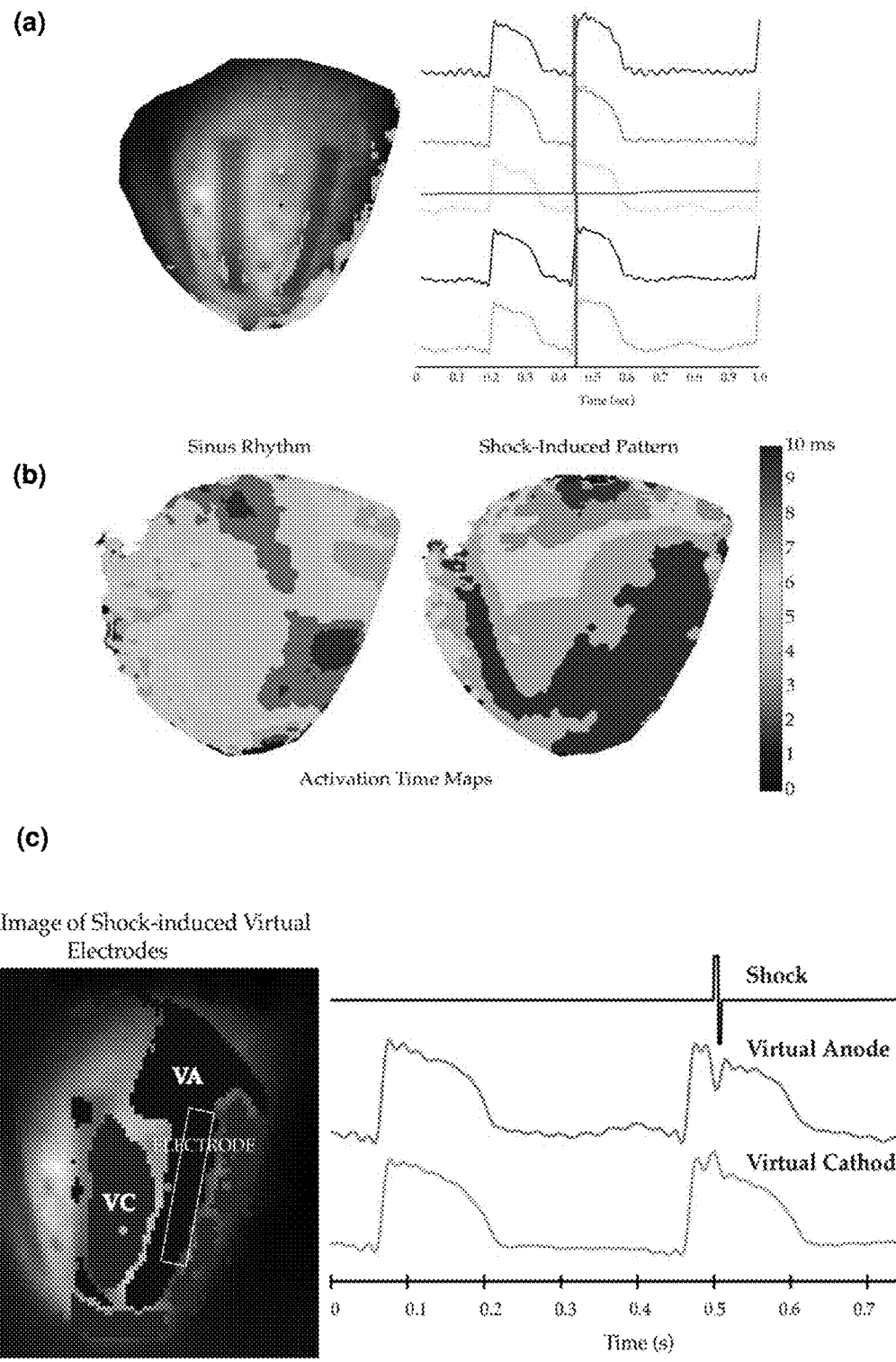
FIG. 30 provides animal experimental data obtained with a device detecting electrical shocks being applied to a Langendorff-perfused rabbit heart.

FIG. 30 provides animal experimental data obtained with a device detecting electrical shocks being applied to a Langendorff-perfused rabbit heart.

Figure 31:
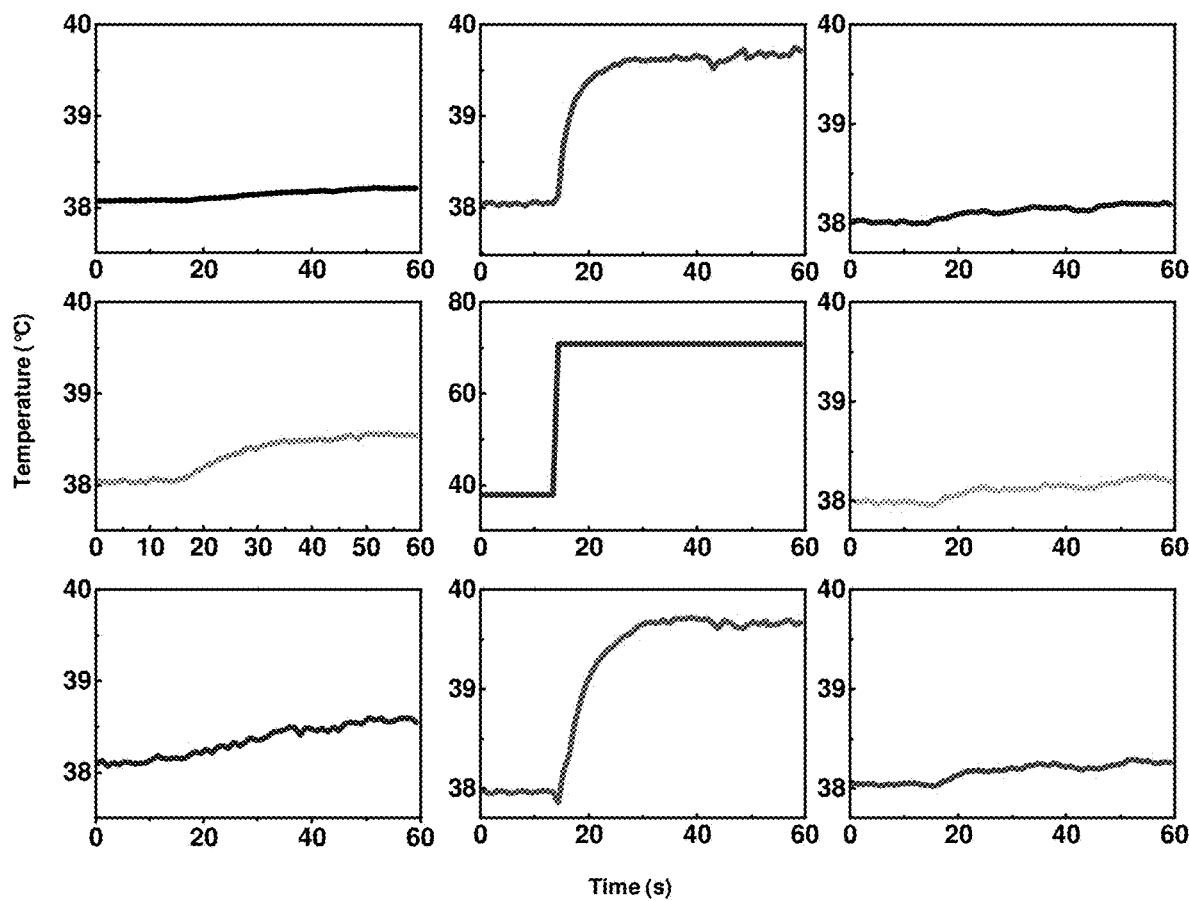
FIG. 31 provides animal experimental data obtained with a device detecting temperature changes in one or more electrodes when heat is applied by another of the device's electrodes.

FIG. 31 provides animal experimental data obtained with a device detecting temperature changes in one or more electrodes when heat is applied by another of the device's electrodes (e.g., a neighboring or nearby electrode).

This example illustrates the applicability of the disclosed tissue mounted devices for providing ablation therapy and substantially simultaneously monitoring temperature of a targeted tissue in order to detect and avoid thermal side-effects associated with ablation therapy.

Example 3: Devices and Methods for Detection of Extracellular Potassium and Hydrogen Ion Concentrations The biomedical devices and methods of the present invention support a broad range of therapeutic and diagnostic applications including multiparametric cardiac mapping and stimulation. This example provides experimental results demonstrating real-time detection of extracellular potassium and hydrogen ion concentrations in myocardial ischemia using a 3D-MIM device comprising intimately integrated ion selective electrodes.

Extracellular potassium (i.e. $K^+$) and hydrogen ion (i.e., pH) have been recognized as major determinants of changes in cardiac electrical activity and the occurrence of arrhythmias in myocardial ischemia. Thus, flexible and stretchable ion selective potentiometric sensors have been developed to monitor these ions quantitatively in situ, as well as to provide intimate bio-integration on a cardiovascular 3D-MIM device. The sensors were fabricated by photolithography and transfer printing technologies and used to monitor ischemic events in real-time by directly mounting the sensors on the surface of cardiac tissue.

Experimental Method and Design

Figure 36:
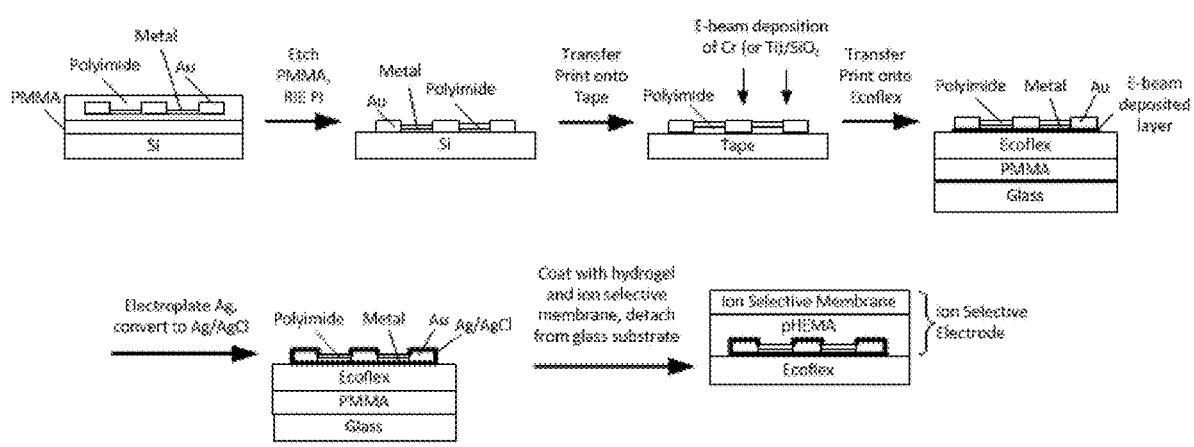
FIG. 36 provides a schematic of a method of making an ion selective electrode, according to an embodiment.

FIG. 36 provides a schematic of a method of making an ion selective electrode, according to an embodiment. The schematic shows steps of the following procedure.

Substrate Preparation.

The silicon wafers were (1) rinsed with acetone/isopropyl alcohol (IPA)/DI water/IPA, gently rubbing with tips of the brush for each chemical; (2) blow dried with $N_2$; and (3) placed under UV for 3 min.

Poly(methyl methacrylate) (PMMA; 495K molecular weight diluted in 2% anisole (A2)) was spin coated at 3,000 rpm (ramp 1,000 rmp/s) for 45 s, while avoiding impurities (e.g., dust and bubbles). The thickness of PMMA layer should be 100 nm and this layer will be used for sacrificial layer for transfer printing techniques.

The PMMA coated wafer was cured on a hotplate at 180° C. for 1 min.

Polyimide (PI) was spin coated above the PMMA layer at 3,000 rpm (1,000 rmp/s) for 45 s. The PI solution exhibits great viscosity, which may require evenly spreading solution out on the wafer using $N_2$ gun.

Prepared wafers were soft baked at 110° C. for 30 s and 150° C. for 5 min, subsequently, and hard baked at 250° C. under vacuum (~1 Torr) for 1 h (PI oven is located in Nano-side of clean room). The PI layer should be 1.2 μm.

Chrome and gold were deposit on the PMMA/PI coated wafer via e-beam deposition. Chrome: 0.5 Å/s rate, 50 Å thickness. Gold: 1.0 Å/s rate, 2,000 Å thickness, Metal Line Patterning.

The wafers were rinsed with acetone/isopropyl alcohol (IPA)/DI water/IPA and blow-dried with $N_2$.

Photoresist (PR) AZ 5214 was spin coated on the substrate at 3,000 rpm (1,000 rpm/s) for 30 s and soft baked at 110° C. for 1 min.

The metal line mask was aligned and exposed UV for 12 s (10.0 $mJ/cm^2$). The PR was developed in 917 MIF developer and then checked under optical microscopy.

Gold was etched with gold etchant (~45 s), checking the statues via optical microscopy.

Chrome was etched with chrome etchant for 12 s (DO NOT shake during this procedure).

The PR was removed by rinsing with acetone. Gently brushing with swipes may help to get better results. The wafers were washed with IPA and blow-dried with $N_2$.

PI Encapsulation.

Polyimide (PI) was spin coated above the patterned gold at 4,000 rpm (1,000 rpm/s) for 60 s. Again, the PI solution exhibits great viscosity, which may require evenly spreading out solution on the wafer using $N_2$ gun.

Prepared wafers were soft baked at 150° C. for 5 min, subsequently, and hard baked at 250° C. under vacuum (~1 Torr) for 1 h.

Serpentine Patterning and Electrode Site VIA Hole.

Photoresist (PR) AZ 4620 was spin coated on the substrate at 3,000 rpm (1,000 rpm/s) for 30 s. The samples were annealed at 110° C. for 3 min. The PR should be warmed up to room temperature before spin coating.

The 'serpentine' mask was aligned and exposed UV for 30 s. The PR was developed with 1:2=AZ 400K: water solution, checking the degree of development with optical microscopy.

The PI was patterned as a serpentine structure using March Reactive Ion Etch (RIE). March RIE parameters were set on as followings: (1) Press 200 Torr; (2) Power 150 W; (3) Time 600 s following with another 300 s if necessary; and (4) Gas $O_2$ 20 sccm.

It is highly recommended to check with optical microscopy for every step.

Transfer Printing.

The PMMA (495 A2) was spin coated on a glass slide at 2,000 rpm (1,000 rpm/s) for 30 s and annealed at 180° C. for 1 min.

The ecoflex A was poured into ecoflex B with 1:1 ratio and stirred. The ecoflex mixture was spin coated on a PMMA/glass slide at 200 rpm for 60 s. The prepared ecoflex substrate was cured at room temperature for 5 min and further hardened at 75° C. for 30 min.

The fabricated devices were released by soaking in boiling acetone (90° C.) clamped between glass slides and techwipes for 15 min.

The devices were dried thoroughly for 15 min and the techwipes removed with extra caution. The water-soluble tape was covered on the devices ironing thoroughly.

The devices were pick up fast with the sticky side of water-soluble tape, and Cr (or Ti)/$SiO_2$ was subsequently deposited on the sticky side of the tape and the devices using e-beam deposition. Chrome (or Titanium): 0.5 Å/s rate, 50 Å thickness. $SiO_2$: 1.0 Å/s rate, 500 Å thickness.

The ecoflex substrates were UV treated for 3 min. Then, transferred devices were placed on top of the ecoflex substrate. These devices were soaked in DI water overnight to remove the water-soluble tape.

The water soluble residue was removed very gently with wet techwipes.

Contact metals, not insulated with PI, were tested with a multimeter ensuring electrical connection.

Bonding ACF Cable.

The ACF cable was cut and placed on the pad area.

The ACF cable was bonded with straightener while placing a PDMS block and glass slide in between. All four directions of the bonding area should be held with straightener for 40 s with firm pressure.

The edge of ACF cable was secured with PDMS or epoxy.

Electroplating Silver Working Electrode.

Fabricated electrodes were immersed into 1 wt % potassium dicyanoargentate (aq.) while stirring the solution.

Electrode potential was applied at −1 V vs. Ag/AgCl for 15 min.

Electroplating charge was ~0.1 C/electrode (1×1 $mm^2$).

The silver electrodes were converted to silver chloride by soaking in 0.1 M $FeCl_3$ (aq.) for 5 min.

Potassium Ion Selective Membrane.

A layer of 2-hydroxyethyl methacrylate (HEMA) monomer containing 4% (w/v) photoinitiator (2,2-dimethoxy-2-phenylacetophenone) was cast onto Ag/AgCl electrode sites and polymerized on electrode area under exposure of 365 nm UV light for 3 min.

The HEMA monomer was removed by washing with methanol, leaving hydrogel over the electrodes sites. The electrodes coated with polyHEMA will be first soaked for >30 min in the 0.1 M KCl and dried at ambient condition.

Following a brief washing with distilled water and gentle blotting of the surface, ion selective membrane cocktail was applied via drop-casting. The ion selective membrane includes: (1) 1.00 wt % potassium ionophore I (i.e., valinomycin), (2) 65.50 wt % bis(2-ethylhexyl)sebacate (DOS) (3) 0.50 wt % potassium tetrakis(4-chlorophenyl)borate, and (4) 33.00 wt % poly(vinyl chloride) high molecular weight (PVC). The membrane solution cocktail will be prepared 240 mg of membrane compounds dissolved in 1 mL tetrahydrofuran (THF). This membrane solution was cast on the polyHEMA layer and dried at ambient. Fabricated ion selective electrodes were stored in 0.1 M NaCl solution until use.

Electrochemical Evaluation.

The sensor performance was evaluated as per pH sensor experiments published previously. The open circuit potential was monitored in real-time using an 8-channel potentiostat, which connected individually with the ISE electrode.

The sensors were calibrated by adding a known amount of analyte ions into either DI water or physiological solution (i.e., Tyrode solution).

As a general summary, an array of ion selective electrodes (ISE) was utilized for detecting extracellular potassium and hydrogen ion concentrations. Eight ultra thin gold electrodes ($1\times1$ mm$^2$ for each) encapsulated with poly(imide) (PI) were fabricated on a silicon wafer using photolithography technology and transfer printed to an elastomeric substrate (e.g., Ecoflex®) capable of stretching, bending and twisting, which provides biomechanical compatibility.

Each ion selective electrode comprised a silver/silver chloride (Ag/AgCl) reference electrode coated with a poly (hydroxyethyl methacrylate) (pHEMA) (i.e., hydrogel) and subsequently coated with an ion selective polymer membrane embedding a neutral carrier ionophore. The Ag/AgCl electrodes were galvanically generated by soaking silver electrodes in 1% ferric chloride (aq.) solution. The pHEMA membrane was photosynthesized with 2-hydroxyethyl methacrylate (HEMA) monomer containing 4 wt % photoinitiator (i.e., 2,2-diethoxy-2-phenylacetophenone) under 365 nm UV for 3 min. This membrane was soaked in 0.1 M KCl solution before modifying with the ion selective poly(vinylchloride) (PVC) membrane. The ion selective membrane comprised an ionophore (i.e., valinomycin and tridecylamine for potassium and hydrogen ion selective electrodes, respectively), bis(2-ethylhexyl)sebacate (DOS) as a plasticizer, potassium tetrakis(4-chlorophenyl)borate as a lipophilic additive, and high molecular weight poly(vinyl chloride) (PVC) as a membrane matrix. This ion selective membrane was drop casted onto the sensor and dried under ambient conditions. After conditioning the ion selective membrane in an ionic strength adjusting solution, the ISE was calibrated in both DI water and physiological buffered solution based on the standard addition method.

In addition, sensor performances were analytically determined for sensitivity, linear response range, response time, and selectivity. Owing to the membrane boundary equilibrium, the sensor response should be mainly dictated by membrane potential change—the sum of two-phase boundary potentials and diffusion potential within the membrane—as a function of ion activity corresponding to the Nernst equation. The fabricated ISE followed the Nernstian response (theoretical sensitivity of 59.2 mV/log [analyte ion]) with reliable selectivity against common interference ion species.

Experimental Results

The local and global ischemic events of ex vivo rabbit heart were evaluated by determining the spatiotemporal change of potassium and hydrogen ion concentrations using ISEs within a 3D-MIM device along with ECG and oxygen level monitoring. The cumulative increase of extracellular K$^+$ was observed in the range of 5-20 mM after interruption of myocardial perfusion triggering an ischemic event and confirmed by a decrease in pO$_2$. Real-time potassium ion concentration changes were observed while inducing local and global ischemia.

Figure 32:
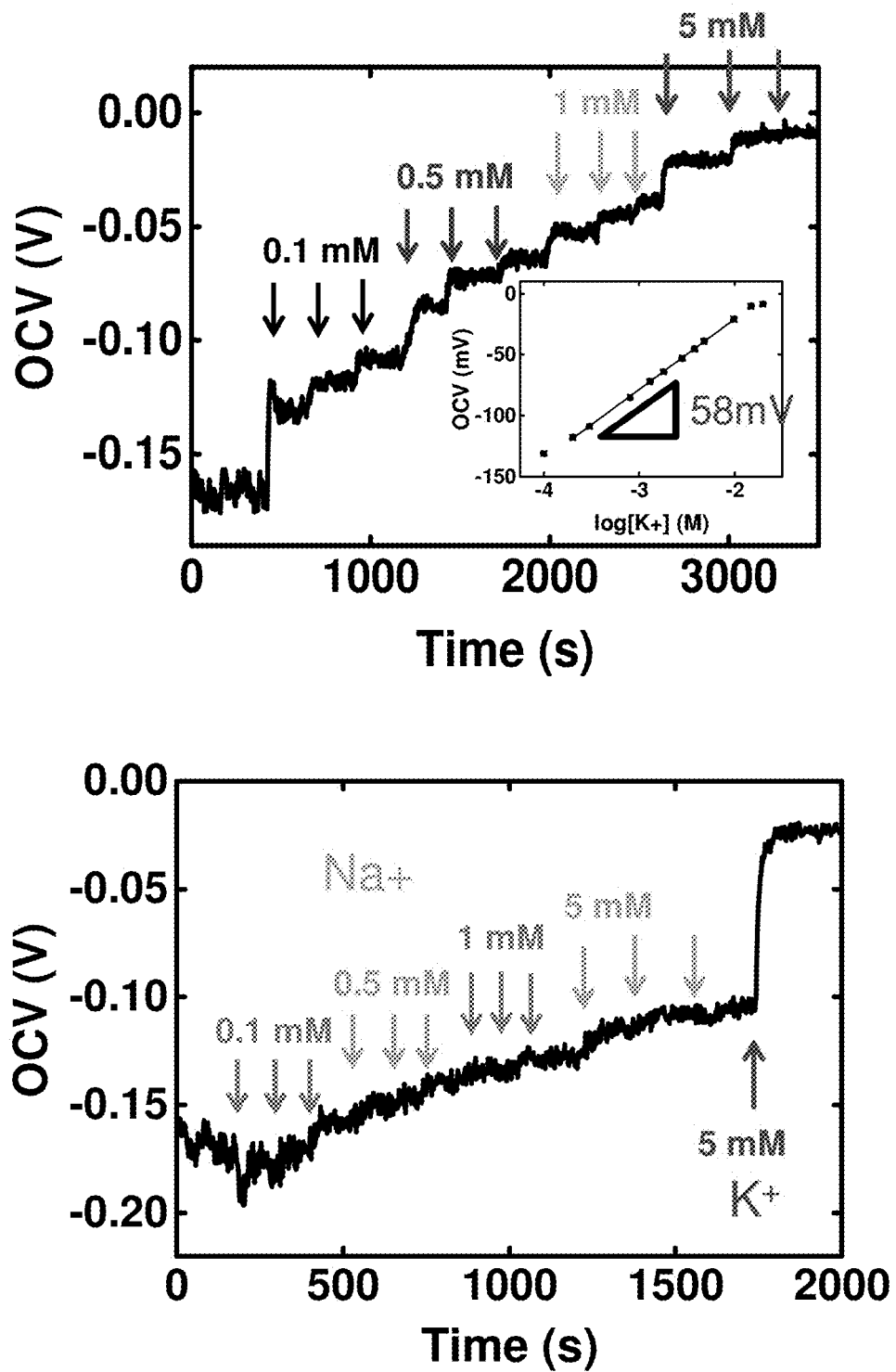
FIG. 32 shows open circuit voltages versus time for potassium ion selective electrodes (ISE) in DI water.

FIG. 32 shows open circuit voltages (OCV) versus time for the potassium ion selective electrodes (ISE) in DI water. The OCV showed an ideal response of 58 mV/log [K$^+$], and high selectivity against Na$^+$.

Figure 33:
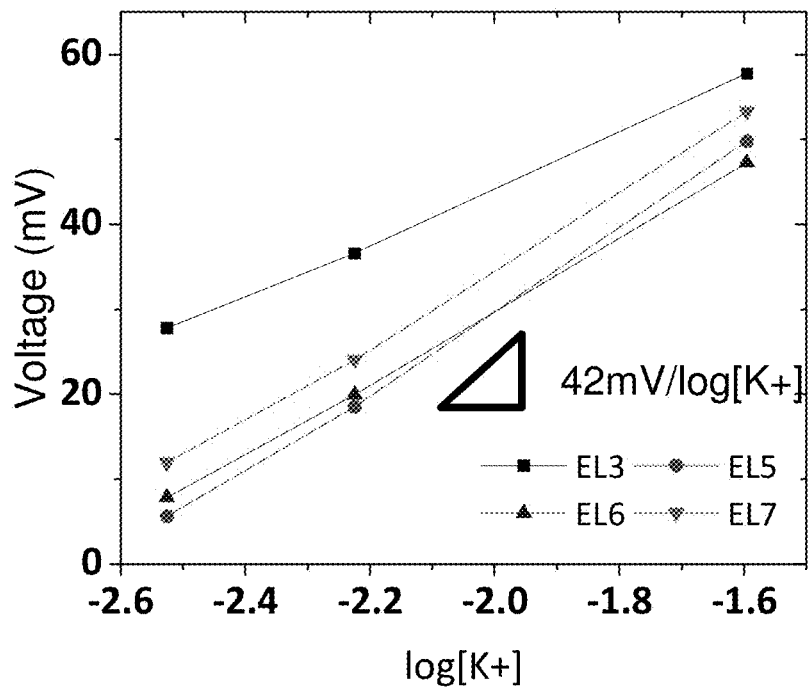
FIG. 33 shows open circuit voltages for potassium ion selective electrodes (ISE) in biological (Tyrode) solution.
Figure 33:
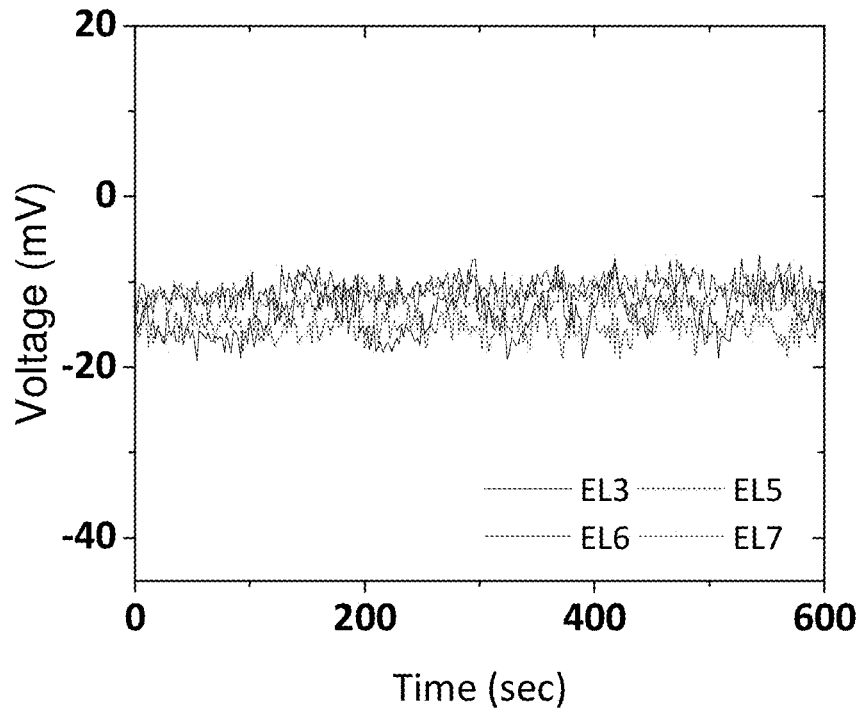

FIG. 33 shows open circuit voltages (OCV) for potassium ion selective electrodes (ISE) in biological (Tyrode) solution. The OCV showed a linear response of 42 mV/log [K$^+$], and a stable voltage against Tyrode.

Figure 34:
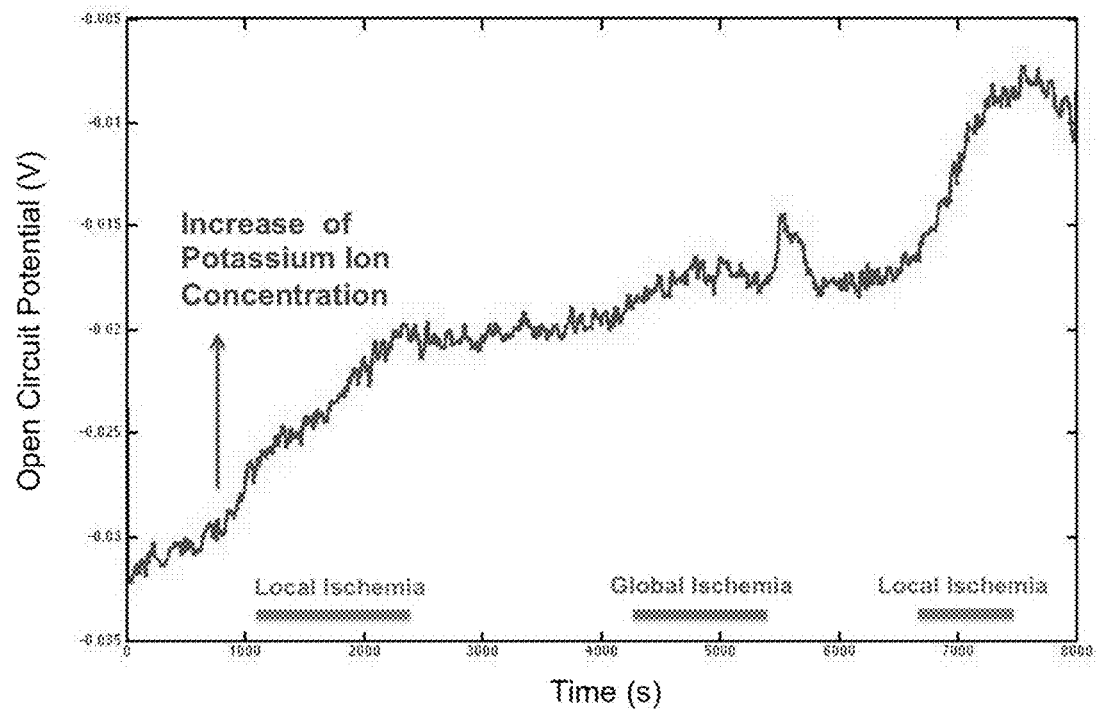
FIG. 34 shows results of a device applied to a Langendorff-perfused rabbit heart to monitor voltage in real-time within the left and right ventricles over the series of local and global ischemic events. A voltage profile over the time course of the experiment is provided. Extracellular potassium ion concentration is monitored during the series of mycyocardial ischemia. The increase of open circuit potential represents a potassium ion concentration change from 5 to 20 mM.

FIG. 34 shows results of a device applied to a Langendorff-perfused rabbit heart to monitor voltage within the left and right ventricles while inducing local and global ischemia. Extracellular potassium ion concentration is monitored during the series of mycyocardial ischemia. The increase of open circuit potential represents a potassium ion concentration change from 5 to 20 mM. The results represent one of four electrodes monitoring each ventricle. Local left side ischemia was induced, followed by reperfusion, then global ischemia was induced, followed by reperfusion, then local left side ischemia was induced, followed by reperfusion. Both ventricles were affected by the second local ischemia.

Figure 35:
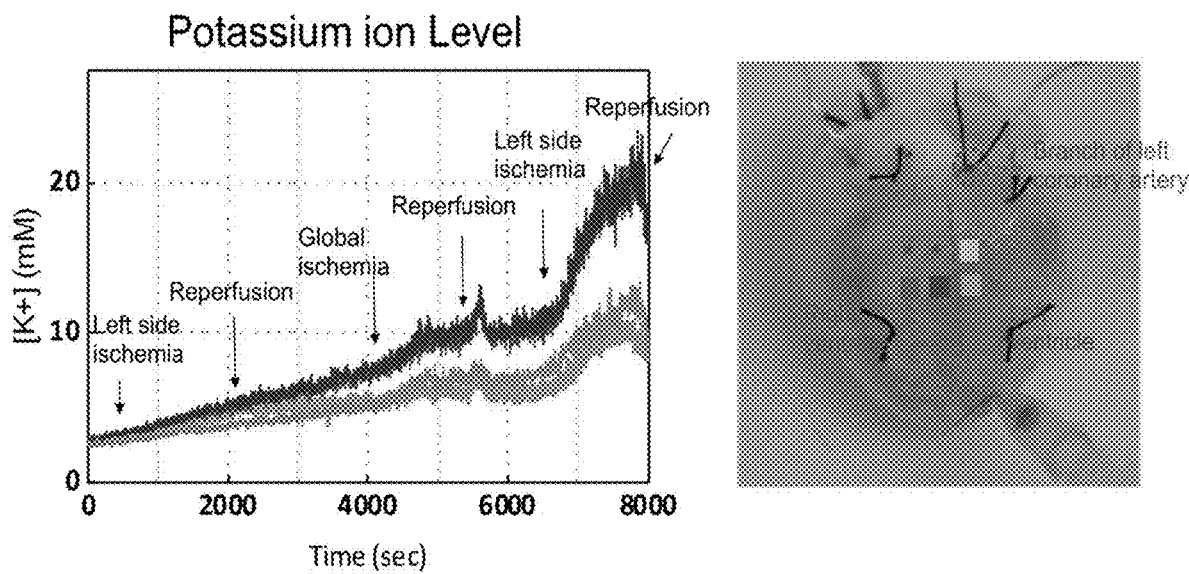
FIG. 35 shows a potassium ion concentration change (left) and image (right) of a device applied to a Langendorff-perfused rabbit heart.

FIG. 35 shows electrochemical results (left) and an image (right) of a device applied to a Langendorff-perfused rabbit heart measuring potassium ion concentration. Potassium level changes for individual ion selective electrodes (ISEs) mounted on Langendorff-perfused rabbit heart during the myocardial ischemia were monitored. The color on the graph is as same as the color of the representative electrode on the pictures. The ischemic events were confirmed by monitoring oxygen level. The potassium ion concentration gradually increased within a reasonable range (5-20 mM). Four ISEs marked with colored boxes measured extracellular potassium ion concentration throughout the ischemia/reperfusion protocol described with respect to FIG. 34. The second left side ischemia induced global ischemia. Electrodes on the right side (blue, red) showed larger changes than electrodes on the left side (green, pink).

REFERENCES

Ahn, J. H. et al. Heterogeneous three-dimensional electronics by use of printed semiconductor nanomaterials. Science 314, 1754-1757 (2006).

Buck, R. P.; Cosofret, V. V.; Lindner, E.; Ufer, S.; Mudaras, M. B.; Johnson, T. A.; Ash, R. B.; Neumun, M. R., Microfabrication technology of flexible membrane based sensors for in vivo applications. *Electroanalysis* 1995, 7 (9), 846-851.

Burk et al. Electrodeposition of Pt Nanoparticle Catalysts from H$_2$Pt(OH)$_6$ and Their Application in PEM Fuel Cells. *J. Phys. Chem. C* 117, 18957 (2013).

Bühlmann, P. and Chen L. D. Ion-Selective Electrodes With Ionophore-Doped Sensing Membranes. Supramolecular Chemistry. Eds. Gale, P. A. and Steed, J. W. John Wiley and Sons, Ltd. 2012. ISBN: 978-0-470-74640-0

Chan, K. W. Y. et al. MRI-detectable pH nanosensors incorporated into hydrogels for in vivo sensing of transplanted-cell viability. Nat. Mater. 12, 268-275 (2013).

Chung, H.-J. et al. Stretchable, multiplexed pH sensors with demonstrations on rabbit and human hearts undergoing ischemia. Adv. Healthc. Mater., 3(1), 59-68 (2014), doi: 10.1002/adhm.201300124.

Dassault Systemes Abaqus analysis user's manual v.6.10. (Dassault Systèmes Simulia Corp., Rhode Island, 2010).

deVries, G., Hamilton, D. R., Ter Keurs, H. E. D. J., Beyar, R. & Tyberg, J. V. A novel technique for measurement of pericardial pressure. Am. J. Physiol. Heart. Circ. Physiol. 280, H2815-H2822 (2001).

D'hooge, J. et al. Regional strain and strain rate measurements by cardiac ultrasound: Principles, implementation and limitations. Eur. J. Echocardiogr. 1, 154-170 (2000).

Efimov, I. R., Nikolski, V. P. & Salama, G. Optical imaging of the heart. Circ. Res. 95, 21-33 (2004).

Farid, T. A. et al. Role of K-atp channels in the maintenance of ventricular fibrillation in cardiomyopathic human hearts. Circ. Res. 109, 1309-U1301 (2011).

Faris, O. P. et al. Novel technique for cardiac electromechanical mapping with magnetic resonance imaging tagging and an epicardial electrode sock. Ann. Biomed. Eng. 31, 430-440 (2003).

Gutbrod, S. R. et al. Patient-specific flexible and stretchable devices for cardiac diagnostics and therapy. Progress in Biophysics and Molecular Biology (2014).

Hancock, E. W. Subacute effusive-constrictive pericarditis. Circulation 43, 183-192 (1971).

Harrison, L. et al. The sock electrode array—a tool for determining global epicardial activation during unstable arrhythmias. Pacing Clin. Electrophysiol. 3, 531-540 (1980).

Holt, J. P., Rhode, E. A. & Kines, H. Pericardial and ventricular pressure. Circ. Res. 8, 1171-1181 (1960).

Janardhan, A. H. et al. Multistage Electrotherapy Delivered Through Chronically-Implanted Leads Terminates Atrial Fibrillation With Lower Energy Than a Single Biphasic Shock. J. Am. Coll. Cardiol, 63(1), 40-48 (2014).

Kim, D. H. et al. Electronic sensor and actuator webs for large-area complex geometry cardiac mapping and therapy. Proc. Natl. Acad. Sci. USA 109, 19910-19915 (2012).

Kim, H. S. et al. Unusual strategies for using indium gallium nitride grown on silicon (111) for solid-state lighting. Proc. Natl. Acad. Sci. USA 108, 10072-10077 (2011).

Kim, R. H. et al. Waterproof AlInGaP optoelectronics on stretchable substrates with applications in biomedicine and robotics. Nat. Mater. 9, 929-937 (2010).

Kim, R. H. et al. Flexible vertical light emitting diodes. Small 8, 3123-3128 (2012).

Lou, Q., Li, W. W. & Efimov, I. R. The role of dynamic instability and wavelength in arrhythmia maintenance as revealed by panoramic imaging with blebbistatin vs. 2,3-butanedione monoxime. Am. J. Physiol. Heart. Circ. Physiol. 302, H262-H269 (2012).

Laughner, J. I., Ng, F. S., Sulkin, M. S., Arthur, R. M. & Efimov, I. R. Processing and analysis of cardiac optical mapping data obtained with potentiometric dyes. Am. J. Physiol. Heart. Circ. Physiol. 303, H753-H765 (2012).

Moore, C. C., Lugo-Olivieri, C. H., McVeigh, E. R. & Zerhouni, E. A. Three-dimensional systolic strain patterns in the normal human left ventricle: Characterization with tagged MR imaging. Radiology 214, 453-466 (2000).

Neely, J. R., Lieberme. H, Battersb. Ej & Morgan, H. E. Effect of pressure development on oxygen consumption by isolated rat heart. Am. J. Physiol. 212, 804-814 (1967).

Rieke, V. & Pauly, K. B. MR thermometry. J. Magn. Reson. Imaging 27, 376-390 (2008).

Shabetai, R. Pericardial effusion: Haemodynamic spectrum. Heart 90, 255-256 (2004).

Smiseth, O. A., Frais, M. A., Kingma, I., Smith, E. R. & Tyberg, J. V. Assessment of pericardial constraint in dogs. Circulation 71, 158-164 (1985).

Timoshenko, S., Woinowsky-Krieger, S., Theory of Plates and Shells. (McGraw-Hill, Kogakusha, 1959).

Tyberg, J. V. et al. The relationship between pericardial pressure and right atrial pressure—an intraoperative study. Circulation 73, 428-432 (1986).

Webb, R. C. et al. Ultrathin conformal devices for precise and continuous thermal characterization of human skin. Nat. Mater. 12, 938-944 (2013).

Worley, S. J. et al. A new sock electrode for recording epicardial activation from the human heart—one size fits all. Pacing Clin. Electrophysiol. 10, 21-31 (1987).

STATEMENTS REGARDING INCORPORATION BY REFERENCE AND VARIATIONS

All references throughout this application, for example patent documents including issued or granted patents or equivalents; patent application publications; and non-patent literature documents or other source material, are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, and methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomer and enantiomer of the compound described individually or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by optional features and preferred embodiments, modification and variation of the concepts herein disclosed may be resorted to by those skilled in the art, and that such modifications and variations are considered to be within the scope of this invention as defined by the appended claims.

The following references relate generally to fabrication methods, structures and systems for making electronic devices, and are hereby incorporated by reference to the extent not inconsistent with the disclosure in this application.

TABLE R1

| Attorney Docket No. | Application No. | Filing Date | Publication No. | Publication Date | Patent No. | Issue Date |
|---|---|---|---|---|---|---|
| 145-03 US | 11/001,689 | Dec. 1, 2004 | 2006/0286488 | Dec. 21, 2006 | 7,704,684 | Apr. 27, 2010 |
| 18-04 US | 11/115,954 | Apr. 27, 2005 | 2005/0238967 | Oct. 27, 2005 | 7,195,733 | Mar. 27, 2007 |
| 38-04A US | 11/145,574 | Jun. 2, 2005 | 2009/0294803 | Dec. 3, 2009 | 7,622,367 | Nov. 24, 2009 |
| 38-04B US | 11/145,542 | Jun. 2, 2005 | 2006/0038182 | Feb. 23, 2006 | 7,557,367 | Jul. 7, 2009 |
| 43-06 US | 11/421,654 | Jun. 1, 2006 | 2007/0032089 | Feb. 8, 2007 | 7,799,699 | Sep. 21, 2010 |
| 38-04C US | 11/423,287 | Jun. 9, 2006 | 2006/0286785 | Dec. 21, 2006 | 7,521,292 | Apr. 21, 2009 |
| 41-06 US | 11/423,192 | Jun. 9, 2006 | 2009/0199960 | Aug. 13, 2009 | 7,943,491 | May 17, 2011 |
| 25-06 US | 11/465,317 | Aug. 17, 2006 | — | — | — | — |
| 137-05 US | 11/675,659 | Feb. 16, 2007 | 2008/0055581 | Mar. 6, 2008 | — | — |
| 90-06 US | 11/782,799 | Jul. 25, 2007 | 2008/0212102 | Sep. 4, 2008 | 7,705,280 | Apr. 27, 2010 |
| 134-06 US | 11/851,182 | Sep. 6, 2007 | 2008/0157235 | Jul. 3, 2008 | 8,217,381 | Jul. 10, 2012 |
| 151-06 US | 11/585,788 | Sep. 20, 2007 | 2008/0108171 | May 8, 2008 | 7,932,123 | Apr. 26, 2011 |
| 216-06 US | 11/981,380 | Oct. 31, 2007 | 2010/0283069 | Nov. 11, 2010 | 7,972,875 | Jul. 5, 2011 |
| 116-07 US | 12/372,605 | Feb. 17, 2009 | — | — | — | — |
| 213-07 US | 12/398,811 | Mar. 5, 2009 | 2010/0002402 | Jan. 7, 2010 | 8,552,299 | Oct. 8, 2013 |
| 38-04D US | 12/405,475 | Mar. 17, 2009 | 2010/0059863 | Mar. 11, 2010 | 8,198,621 | Jun. 12, 2012 |
| 170-07 US | 12/418,071 | Apr. 3, 2009 | 2010/0052112 | Mar. 4, 2010 | 8,470,701 | Jun. 25, 2013 |
| 216-06A US | 12/522,582 | Jul. 9, 2009 | — | — | — | — |
| 38-04A1 US | 12/564,566 | Sep. 22, 2009 | 2010/0072577 | Mar. 25, 2010 | 7,982,296 | Jul. 19, 2011 |
| 71-07 US | 12/669,287 | Jan. 15, 2010 | 2011/0187798 | Aug. 4, 2011 | — | — |
| 60-09 US | 12/778,588 | May 12, 2010 | 2010/0317132 | Dec. 16, 2010 | — | — |
| 43-06A US | 12/844,492 | Jul. 27, 2010 | 2010/0289124 | Nov. 18, 2010 | 8,039,847 | Oct. 18, 2011 |
| 15-10 US | 12/892,001 | Sep. 28, 2010 | 2011/0230747 | Sep. 22, 2011 | 8,666,471 | Mar. 4, 2014 |
| 15-10A | 14/140,299 | Dec. 24, 2013 | — | — | — | — |

TABLE R1-continued

| Attorney Docket No. | Application No. | Filing Date | Publication No. | Publication Date | Patent No. | Issue Date |
|---|---|---|---|---|---|---|
| 19-10 US | 12/916,934 | Nov. 1, 2010 | 2012/0105528 | May 3, 2012 | 8,562,095 | Oct. 22, 2013 |
| 3-10 US | 12/947,120 | Nov. 16, 2010 | 2011/0170225 | Jul. 14, 2011 | — | — |
| 118-08 US | 12/996,924 | Dec. 8, 2010 | 2011/0147715 | Jun. 23, 2011 | — | — |
| 126-09 US | 12/968,637 | Dec. 15, 2010 | 2012/0157804 | Jun. 21, 2012 | — | — |
| 50-10 US | 13/046,191 | Mar. 11, 2011 | 2012/0165759 | Jun. 28, 2012 | — | — |
| 151-06A US | 13/071,027 | Mar. 24, 2011 | 2011/0171813 | Jul. 14, 2011 | — | — |
| 137-05A US | 13/095,502 | Apr. 27, 2011 | — | — | — | — |
| 216-06B US | 13/100,774 | May 4, 2011 | 2011/0266561 | Nov. 3, 2011 | — | — |
| 38-04A2 US | 13/113,504 | May 23, 2011 | 2011/0220890 | Sep. 15, 2011 | 8,440,546 | May 14, 2013 |
| 136-08 US | 13/120,486 | Aug. 4, 2011 | 2011/0277813 | Nov. 17, 2011 | — | — |
| 151-06B US | 13/228,041 | Sep. 8, 2011 | 2011/0316120 | Dec. 29, 2011 | — | — |
| 43-06B US | 13/270,954 | Oct. 11, 2011 | 2012/0083099 | Apr. 5, 2012 | 8,394,706 | Mar. 12, 2013 |
| 3-11 US | 13/349,336 | Jan. 12, 2012 | 2012/0261551 | Oct. 18, 2012 | — | — |
| 38-04E US | 13/441,618 | Apr. 6, 2012 | 2013/0100618 | Apr. 25, 2013 | — | — |
| 134-06B US | 13/441,598 | Apr. 6, 2012 | 2012/0327608 | Dec. 27, 2012 | — | — |
| 28-11 US | 13/472,165 | May 15, 2012 | 2012/0320581 | Dec. 20, 2012 | — | — |
| 7-11 US | 13/486,726 | Jun. 1, 2012 | 2013/0072775 | Mar. 21, 2013 | — | — |
| 29-11 US | 13/492,636 | Jun. 8, 2012 | 2013/0041235 | Feb. 14, 2013 | — | — |
| 84-11 US | 13/549,291 | Jul. 13, 2012 | 2013/0036928 | Feb. 14, 2013 | — | — |
| 25-06A US | 13/596,343 | Aug. 28, 2012 | 2012/0321785 | Dec. 20, 2012 | 8,367,035 | Feb. 5, 2013 |
| 150-11 US | 13/624,096 | Sep. 21, 2012 | 2013/0140649 | Jun. 6, 2013 | — | — |
| 38-04A3 US | 13/801,868 | Mar. 13, 2013 | 2013/0320503 | Dec. 5, 2013 | 8,664,699 | Mar. 4, 2014 |
| 125-12 US | 13/835,284 | Mar. 15, 2013 | — | — | — | — |
| 30-13 US | 13/853,770 | Mar. 29, 2013 | 2013/0333094 | Dec. 19, 2013 | — | — |
| 19-10A US | 14/033,765 | Sep. 23, 2013 | 2014/0092158 | Apr. 3, 2014 | — | — |
| 38-04A4 US | 14/155,010 | Jan. 14, 2014 | — | — | — | — |
| 134-06C US | 14/220,910 | Mar. 20, 2014 | — | — | — | — |
| 38-04F US | 14/220,923 | Mar. 20, 2014 | — | — | — | — |
| 151-06C US | 14/246,962 | Apr. 7, 2014 | — | — | — | — |
| 62-13 US | 14/250,671 | Apr. 11, 2014 | — | — | — | — |
| 56-13 US | 14/251,259 | Apr. 11, 2014 | — | — | — | — |

We claim:

1. A device for interfacing with an internal biological tissue, the device comprising:
a flexible and stretchable substrate having an inner surface and an external surface, wherein the inner surface defines an enclosure to enclose the internal biological tissue;
a flexible and stretchable electronic device or device component comprising three or more different types of sensors, supported by the inner surface of the flexible and stretchable substrate, wherein the sensors are configured for multiparametric mapping of a plurality of parameters comprising electric potential and one or more additional parameters selected from the group consisting of temperature, pH, ion concentration, intrinsic fluorescence, spatial position, force and pressure;
the sensors comprising one or more inorganic semiconductor components, one or more metallic components, or one or more inorganic semiconductor components and one or more metallic components; wherein at least a portion of the inorganic semiconductor components, the metallic components or both have a thickness less than or equal to 500 microns;
wherein the flexible and stretchable substrate and the electronic device or device component provide a net bending stiffness of the device low enough such that the inner surface of the substrate is capable of establishing conformal contact with at least 70% of an outer surface of the internal biological tissue; and
wherein the flexible and stretchable substrate and the electronic device or device component generates a contact force generated by an elastic force of the enclosure in an expanded state, wherein the contact force corresponds to a contact pressure that is sufficiently low to avoid an adverse physiological response from the internal biological tissue and remains sufficiently high to maintain said conformal contact;
wherein the contact pressure is greater than or equal to 10 Pa and less than or equal to 1 kPa and is substantially uniformly distributed over an outer surface of the internal biological tissue in conformal contact with the flexible and stretchable substrate and a peak pressure is less than or equal to 3 times the contact pressure averaged over the outer surface of the internal biological tissue in conformal contact with the flexible and stretchable substrate.

2. The device of claim 1, wherein the expanded state is an increase in a volume of the enclosure of between 1% and 100% to accommodate the internal biological tissue within the enclosure.

3. The device of claim 1, wherein said conformal contact is maintained during deformation of the internal biological tissue within the enclosure.

4. The device of claim 1, wherein the enclosure has a shape complementary to an outer surface shape of a heart.

5. The device of claim 1, wherein the enclosure has an enclosure volume that is selected from a range that is greater than or equal to 0.1 cm$^3$ and less than or equal to 2,000 cm$^3$.

6. The device of claim 5, wherein the enclosure volume varies to accommodate volume or surface shape changes in the internal biological tissue over time and the contact force remains sufficiently high to maintain said conformal contact and sufficiently low to avoid an adverse physiological response.

7. The device of claim 1, wherein the device has an enclosure surface area that is selected from a range that is greater than or equal to 100 µm$^2$ and less than or equal to 800 cm$^2$.

8. The device of claim 1, wherein the internal biological tissue is selected from the group consisting of: an organ, a blood vessel, a bone, any combinations thereof, and any portions thereof.

9. The device of claim 1, wherein the internal biological tissue comprises a heart having an outer surface corresponding to heart epicardium.

10. The device of claim 1, wherein the enclosure completely envelops the internal biological tissue.

11. The device of claim 1, wherein the device in conformal contact with the internal biological tissue is immersed in a fluid.

12. The device of claim 1, wherein the flexible and stretchable electronic device or device component further comprises an array of actuators.

13. The device of claim 12, wherein the array of actuators is selected from the group consisting of an electrode, a heat source, a piezoelectric element, an acoustic element, a source of RF energy, a magnetic actuator, a source of electromagnetic radiation, a laser, a light emitting diode and combinations thereof.

14. The device of claim 12 wherein at least one sensor is selected from the group consisting of a strain sensor, a capacitance sensor, a chemical sensor, a capacitive sensor, an optical sensor, a photodetector, an imaging system and any arrays and combinations thereof.

15. The device of claim 14, wherein the sensors comprise an array of temperature sensors to monitor a spatial distribution of temperature.

16. The device of claim 15, wherein each temperature sensor in the array of temperature sensors independently comprises:
a serpentine electrically conductive nanowire having an electrical resistance that varies with changes in temperature.

17. The device of claim 15, further comprising one or more thermal actuators for spatially controlled heating of the internal biological tissue which is independently monitored by the array of temperature sensors.

18. The device of claim 12, wherein the sensors, actuators or both the sensors and the actuators move synchronously with internal biological tissue that underlays the sensors, the actuators or both the sensors and the actuators.

19. The device of claim 12, wherein the sensors comprise an array of electrodes for mapping internal biological tissue electrical activity, wherein the electrodes are positioned in an array and spaced between 1 µm and 5 mm apart from each other, and wherein the electrodes are distributed over a surface area that is greater than or equal to 0.1 mm$^2$ and less than or equal to 1000 mm$^2$.

20. The device of claim 19, wherein the electrodes comprise an array distributed over the flexible and stretchable substrate to monitor electrical activity on both an anterior and posterior surface of a heart.

21. The device of claim 12, wherein the sensors comprise an array of pH sensors and/or potassium ion sensors to provide an indication of metabolic state of internal biological tissue underlying the sensors.

22. The device of claim 21, wherein the pH sensors provide for measurement of pH, transmembrane potential, calcium transient signals or any combination of these.

23. The device of claim 21, wherein the potassium ion sensors provide for measurement of extracellular potassium ion concentration, open cell voltage or any combination of these.

24. The device of claim 1, wherein the flexible and stretchable electronic device or device component is multifunctional.

25. The device of claim 1, wherein at least one of the three or more sensors comprise a strain sensor.

26. The device of claim 1, wherein the electronic device or device component comprises a plurality of optical sources.

27. The device of claim 26, wherein the optical sources comprise one or more light emitting diodes (LEDs), wherein the LEDs each independently have a thickness less than 10 µm and a surface area that is less than 0.25 mm$^2$.

28. The device of claim 1, comprising an optically transparent device that is transparent for at least a portion of wavelengths in the visible region of the electromagnetic spectrum.

29. The device of claim 1, wherein said inner surface of the substrate establishes a continuous physical contact with an area of said outer surface of the internal biological tissue selected from the range of 100 µm$^2$ to 800 cm$^2$.

30. The device of claim 1, wherein the flexible and stretchable substrate and the electronic device or device component provide a net flexural rigidity of the device less than or equal to $1 \times 10^{-4}$.

31. The device of claim 1, wherein the electronic device or device component comprises up to 10,000 of the sensors.

32. The device of claim 1, wherein the sensors are electrically connected via a network of serpentine electrical interconnects.

33. The device of claim 1, wherein the sensors are provided in an open mesh geometry.

34. The device of claim 1, wherein the sensors have a spatial density of between about 1 cm$^{-2}$ to 1 mm$^{-2}$.

35. The device of claim 1, wherein the flexible and stretchable substrate has a thickness that is less than or equal to 1 mm.

36. The device of claim 1, wherein the flexible and stretchable substrate has an average modulus less than or equal to 500 kPa.

37. The device of claim 1, wherein the flexible and stretchable substrate has an average modulus equal to or less than 50 times the average modulus of the internal biological tissue at the interface with the inner surface of the flexible and stretchable substrate.

38. The device of claim 1, wherein the flexible and stretchable substrate forms a closed surface over the internal biological tissue.

39. The device of claim 1, wherein the flexible and stretchable substrate comprises a low modulus elastomer.

40. A method of making a device for interfacing with an internal biological tissue, the method comprising the steps of:
transferring a flexible and stretchable electronic device or device component to a flexible and stretchable substrate, wherein the flexible and stretchable electronic device or device component comprises three or more different types of sensors supported by an inner surface of the flexible and stretchable substrate; wherein the sensors are configured for multiparametric mapping of a plurality of parameters comprising electric potential and one or more additional parameters selected from the group consisting of temperature, pH, ion concentration, intrinsic fluorescence, spatial position, force and pressure;
wherein the sensors comprise one or more inorganic semiconductor components, one or more metallic components, or both one or more inorganic semiconductor components and one or more metallic components; wherein at least a portion of the inorganic semiconductor components, metallic components or both has a thickness less than or equal to 500 microns; and shaping the flexible and stretchable substrate to be complementary to a three-dimensional surface shape of the internal biological tissue, thereby making an enclosure for receiving and enclosing at least 70% of an outer surface of the internal biological tissue wherein the flexible and stretchable substrate and the electronic device or device component is configured to generate a contact force generated by an elastic force of the enclosure in an expanded state, wherein the contact force corresponds to a contact pressure that is sufficiently low to avoid an adverse physiological response from the internal biological tissue and remains sufficiently high to maintain a conformal contact;

wherein the contact pressure is greater than or equal to 10 Pa and less than or equal to 1 kPa and is substantially uniformly distributed over an outer surface of the internal biological tissue in conformal contact with the flexible and stretchable substrate and a peak pressure is less than or equal to 3 times the contact pressure averaged over the outer surface of the internal biological tissue in conformal contact with the flexible and stretchable substrate.

41. The method of claim 40, wherein the sensors are positioned on an enclosure-forming surface of the flexible and stretchable substrate.

42. The method of claim 40, further comprising:
applying the flexible and stretchable electronic device or device component to an outer surface of the biological tissue; and
casting a flexible and stretchable layer against the flexible and stretchable electronic device or device component applied to the outer surface of the biological tissue.

43. The method of claim 40, wherein the enclosure has a dimension that is less than a dimension of the internal biological tissue to be enclosed by the enclosure, thereby generating a contact force between the device and the internal biological tissue to maintain conformal contact during use due to an elasticity of the flexible and stretchable substrate when in an expanded state.

44. A method of interfacing with an internal biological tissue, the method comprising the steps of:

providing a device comprising a flexible and stretchable electronic device or device component comprising three or more different types of sensors supported by an inner surface of a flexible and stretchable substrate, wherein the sensors are configured for multiparametric mapping of a plurality of parameters comprising electric potential and one or more additional parameters selected from the group consisting of temperature, pH, ion concentration, intrinsic fluorescence, spatial position, force and pressure;

the sensors comprising one or more inorganic semiconductor components, one or more metallic components, or both one or more inorganic semiconductor components and one or more metallic components;

wherein at least a portion of the inorganic semiconductor components, the metallic components or both has a thickness less than or equal to 500 microns; and wherein the inner surface of the flexible or stretchable substrate defines an enclosure;

expanding the enclosure to an expanded state; and enclosing the internal biological tissue within the enclosure in the expanded state, thereby generating an elastic contact force to conformally mount and enclose the internal biological tissue to the device and interface with the internal biological tissue, wherein the device encloses at least 70% of an outer surface of the internal biological tissue;

wherein the flexible and stretchable substrate and the electronic device or device component generates a contact force generated by an elastic force of the enclosure in an expanded state, wherein the contact force corresponds to a contact pressure that is sufficiently low to avoid an adverse physiological response from the internal biological tissue and remains sufficiently high to maintain a conformal contact;

wherein the contact pressure is greater than or equal to 10 Pa and less than or equal to 1 kPa and is substantially uniformly distributed over an outer surface of the internal biological tissue in conformal contact with the flexible and stretchable substrate and a peak pressure is less than or equal to 3 times the contact pressure averaged over the outer surface of the internal biological tissue in conformal contact with the flexible and stretchable substrate.

* * * * *